US010233249B2

(12) United States Patent
Qian et al.

(10) Patent No.: US 10,233,249 B2
(45) Date of Patent: Mar. 19, 2019

(54) ANTIBODIES AND METHODS FOR TREATING ESTROGEN RECEPTOR-ASSOCIATED DISEASES

(71) Applicant: BEIJING SHENOGEN PHARMA GROUP LTD., Beijing (CN)

(72) Inventors: Xueming Qian, Beijing (CN); Kun Meng, Beijing (CN); Feng Chen, Beijing (CN); Xiao Shang, Beijing (CN); Jing Wang, Beijing (CN); Lu Li, Beijing (CN); Congya Zhou, Beijing (CN)

(73) Assignee: BEIJING SHENOGEN PHARMA GROUP LTD., Beijing (CN)

( * ) Notice: Subject to any disclaimer, the term of this patent is extended or adjusted under 35 U.S.C. 154(b) by 488 days.

(21) Appl. No.: 14/778,686

(22) PCT Filed: Mar. 19, 2014

(86) PCT No.: PCT/CN2014/073673
§ 371 (c)(1),
(2) Date: Sep. 21, 2015

(87) PCT Pub. No.: WO2014/146575
PCT Pub. Date: Sep. 25, 2014

(65) Prior Publication Data
US 2016/0046721 A1    Feb. 18, 2016

(30) Foreign Application Priority Data

Mar. 19, 2013  (WO) ............... PCT/CN2013/072844

(51) Int. Cl.
*A61K 39/395* (2006.01)
*C07K 16/28* (2006.01)
*G01N 33/74* (2006.01)
*A61K 45/06* (2006.01)
*A61K 47/68* (2017.01)
*A61K 39/00* (2006.01)

(52) U.S. Cl.
CPC ...... *C07K 16/2869* (2013.01); *A61K 39/3955* (2013.01); *A61K 45/06* (2013.01); *A61K 47/6803* (2017.08); *A61K 47/6811* (2017.08); *A61K 47/6847* (2017.08); *A61K 47/6849* (2017.08); *A61K 47/6889* (2017.08); *G01N 33/743* (2013.01); *A61K 2039/505* (2013.01); *C07K 2317/24* (2013.01); *C07K 2317/34* (2013.01); *C07K 2317/56* (2013.01); *C07K 2317/565* (2013.01); *C07K 2317/73* (2013.01); *C07K 2317/76* (2013.01); *C07K 2317/92* (2013.01); *C07K 2319/02* (2013.01); *G01N 2333/723* (2013.01)

(58) Field of Classification Search
None
See application file for complete search history.

(56) References Cited

FOREIGN PATENT DOCUMENTS

| EP | 2 534 256 A1 | 12/2012 |
|---|---|---|
| JP | 2007-528406 A | 10/2007 |
| WO | WO 96/39518 A1 | 12/1996 |
| WO | WO 2005/087811 A2 | 9/2005 |
| WO | WO 2005/102387 A2 | 11/2005 |
| WO | WO 2008/052005 A2 | 5/2008 |
| WO | WO 2010091637 A1 | 8/2010 |
| WO | WO 2015/014284 A1 | 2/2015 |

OTHER PUBLICATIONS

Paul (1993) Fundamental Immunology, #rd edition, pp. 292-295.*
Bendig (1995) Methods: a companion. Methods in Enzymology *: 83-93.*
MacCallum et al. (1996) J. Mol. Biol. 262: 732-745.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
International Preliminary Report on Patentability dated Sep. 22, 2015 received from International Application No. PCT/CN2014/073673.
Gu Y. et al., "The Therapeutic Target of Estrogen Receptor-Alpha36 in Estrogen-Dependent Tumors" *Journal of Translational Medicine* 12(16):1-12 (2014).
Jiang L. et al., "Crosstalk Between Estrogen Receptor Alpha 36, a Dominant Extra-Nuclear ER, and HER2 Promotes Tumor Cell Survival in Breast Cancer", *Cell Survival in Breast Cancer* 69(24 Suppl) (3 pages) (Dec. 15, 2009).
Wang Z Y et al., "A Variant of Estrogen Receptor-α, hER-α36: Transduction of Estrogen- and Antiestrogen-Dependent Membrane-Initiated Mitogenic Signaling", *PNAS* 103(24):9063-9068 (Jun. 13, 2006).
Partial Supplementary European Search Report dated Nov. 16, 2016 received in European Application No. 14 77 0917.4.
Supplementary European Search Report dated Nov. 9, 2016 received in European Application No. 14 77 0917.4.
Partial Supplementary European Search Report dated Sep. 23, 2016 received in European Application No. 14 77 0917.4.
European Search Opinion dated May 27, 2016 received in European Application No. 14 77 0917.4.
Japanese Office Action dated Jan. 9, 2018 issued in JP 2016-503529, toghether with an English translation.
Panka, D.J. et al., "Variable region framework differences result in decreased or increased affinity of variant anti-digoxin antibodies", Proc. Natl. Acad. Sci. USA, (May 1988), vol. 85, pp. 3080-3084.

(Continued)

Primary Examiner — Michael D Pak
(74) Attorney, Agent, or Firm — Scully Scott Murphy & Presser

(57) ABSTRACT

Provided herein in certain embodiments are antibodies, antibody fragments, pharmaceutical compositions, methods for modulating the functions of estrogen receptor alpha 36, and methods for preventing and/or treating diseases mediated by estrogen receptor alpha 36.

14 Claims, 30 Drawing Sheets

Specification includes a Sequence Listing.

(56) References Cited

OTHER PUBLICATIONS

Casadevall. A. et al., "Immunoglobulin isotype influences affinity and specificity", PNAS, (Jul. 31, 2012), vol. 109, No. 31, 2 pages.
Rudnick, S.I. et al., "Affinity and Avidity in Antibody-Based Tumor Targeting", Cancer Biotherapy and Radiopharmaceuticals, (2009), vol. 24, No. 2, pp. 155-161.
European Office Action dated Nov. 24, 2017 issued in EP 14 770 917.4.

* cited by examiner

```
MTMTLHTKAS GMALLHQIQG NELEPLNRPQ LKIPLERPLG EVYLDSSKPA
VYNYPEGAAY EFNAAAAANA QVYGQTGLPY GPGSEAAAFG SNGLGGFPPL
NSVSPSPLML LHPPPQLSPF LQPHGQQVPY YLENEPSGYT VREAGPPAFY
RPNSDNRRQG GRERLASTND KGSMAMESAK ETRYCAVCND YASGYHYGVW
SCEGCKAFFK RSIQGHNDYM CPATNQCTID KNRRKSCQAC RLRKCYEVGM
MKGGIRKDRR GGRMLKHKRQ RDDGEGRGEV GSAGDMRAAN LWPSPLMIKR
SKKNSLALSL TADQMVSALL DAEPPILYSE YDPTRPFSEA SMMGLLTNLA
DRELVHMINW AKRVPGFVDL TLHDQVHLLE CAWLEILMIG LVWRSMEHPG
KLLFAPNLLL DRNQGKCVEG MVEIFDMLLA TSSRFRMMNL QGEEFVCLKS
IILLNSGVYT FLSSTLKSLE EKDHIHRVLD KITDTLIHLM AKAGLTLQQQ
HQRLAQLLLI LSHIRHMSNK GMEHLYSMKC KNVVPLYDLL LEMLDAHRLH
APTSRGGASV EETDQSHLAT AGSTSSHSLQ KYYITGEAEG FPATV
```

1a

```
MAMESAKETR YCAVCNDYAS GYHYGVWSCE GCKAFFKRSI QGHNDYMCPA
TNQCTIDKNR RKSCQACRLR KCYEVGMMKG GIRKDRRGGR MLKHKRQRDD
GEGRGEVGSA GDMRAANLWP SPLMIKRSKK NSLALSLTAD QMVSALLDAE
PPILYSEYDP TRPFSEASMM GLLTNLADRE LVHMINWAKR VPGFVDLTLH
DQVHLLECAW LEILMIGLVW RSMEHPGKLL FAPNLLLDRN QGKCVEGMVE
IFDMLLATSS RFRMMNLQGE EFVCLKSIIL LNSGVYTFLS STLKSLEEKD
HIHRVLDKIT DTLIHLMAKA GLTLQQQHQR LAQLLLILSH IRHMSNKGME
HLYSMKCKNV VPLYDLLLEM LDAHRLHAPT SRGGASVEET DQSHLATAGS
TSSHSLQKYY ITGEAEGFPA TV
```

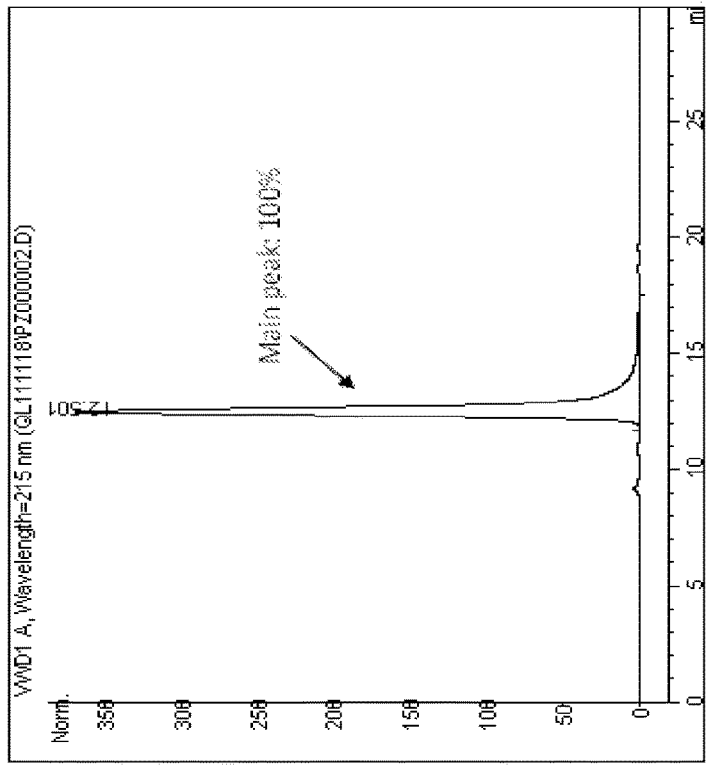
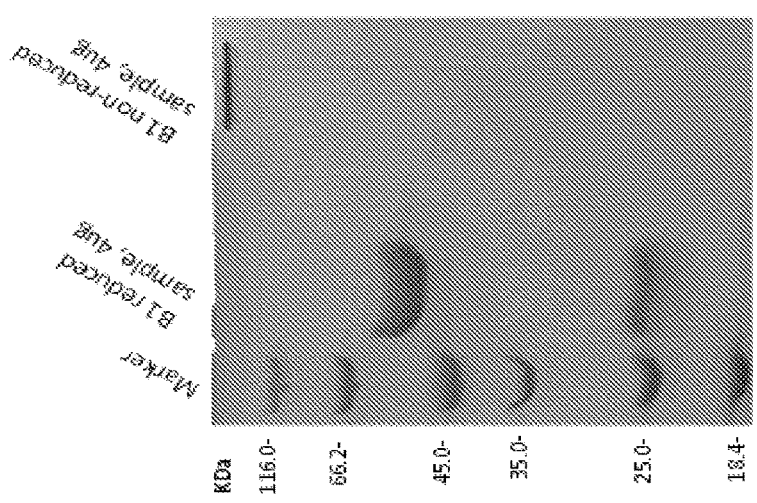
Figure 2

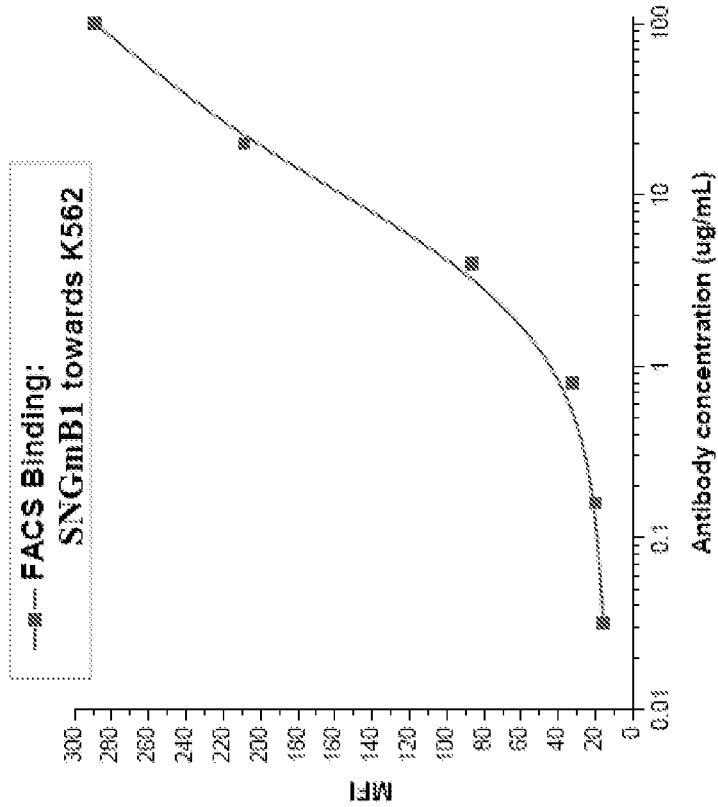
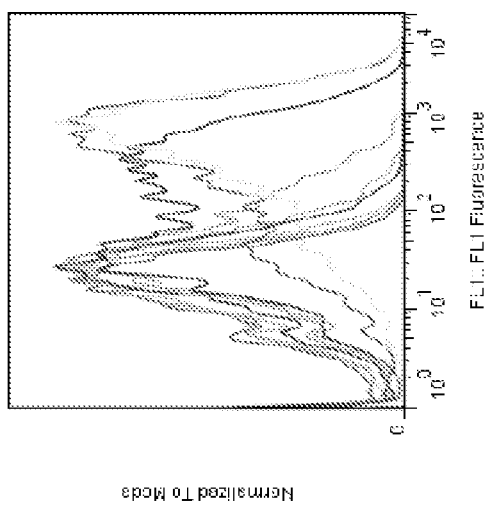
Figure 5A

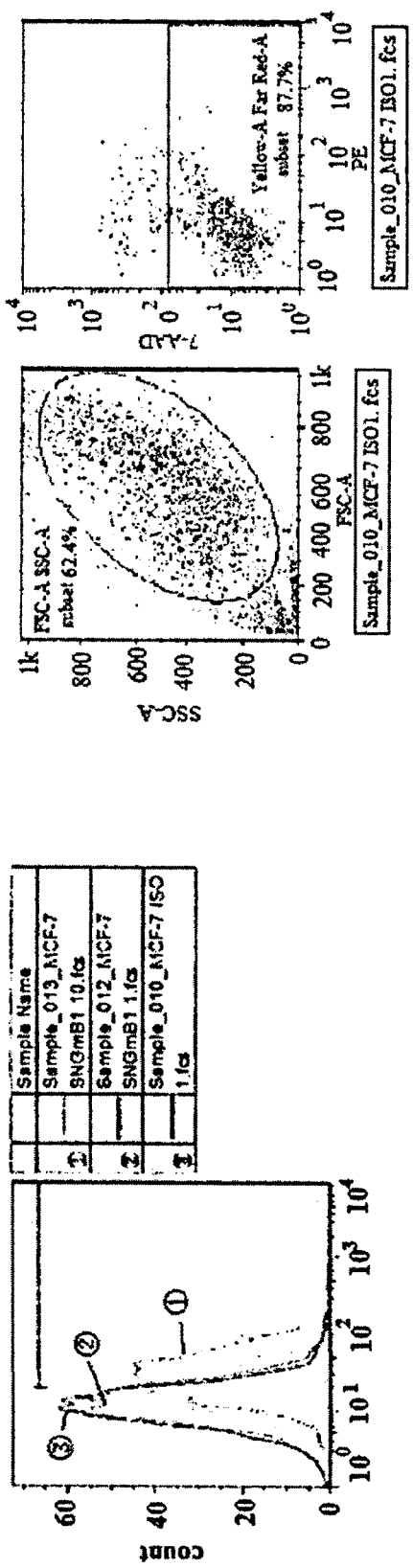
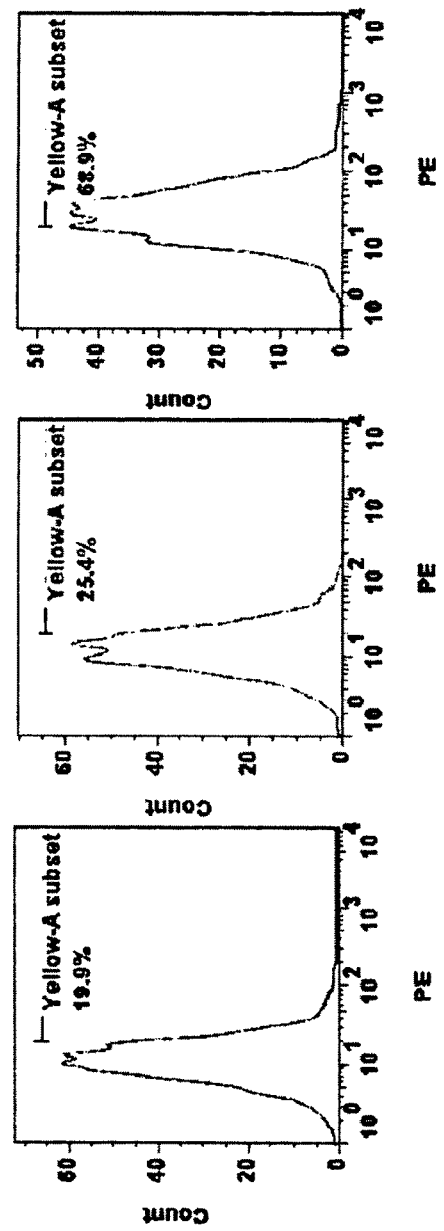
Figure 5B

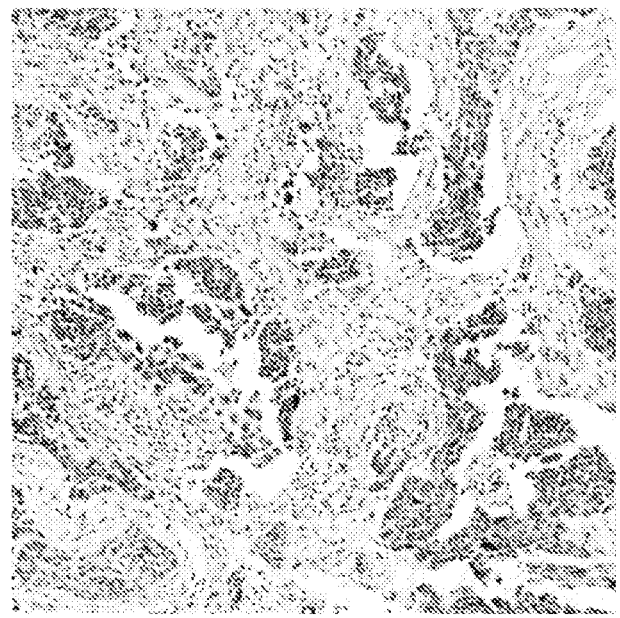
(A)
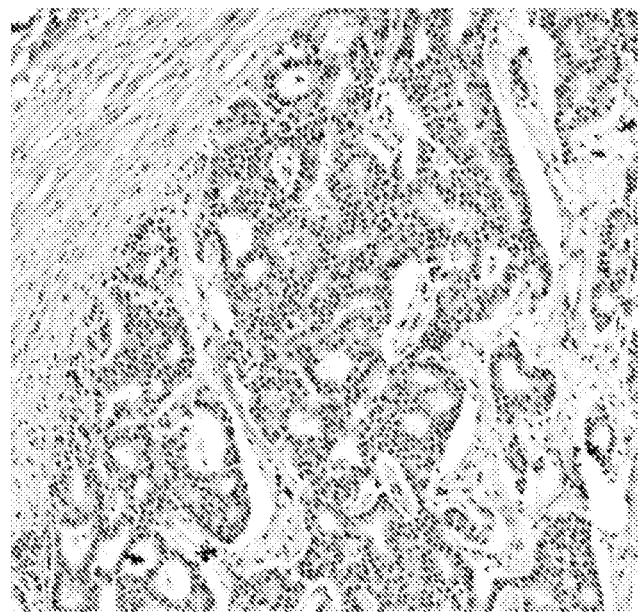
(B)
Figure 11

ANTIBODIES AND METHODS FOR TREATING ESTROGEN RECEPTOR-ASSOCIATED DISEASES

CROSS-REFERENCE TO RELATED APPLICATIONS

The present application is the national phase of International Application No. PCT/CN2014/073673, filed Mar. 19, 2014, which claims priority from PCT Patent Application Number PCT/CN2013/072844, filed on Mar. 19, 2013, the contents of which are incorporated herein by reference in its entirety.

FIELD OF THE INVENTION

The present invention relates to antibodies, pharmaceutical compositions and methods thereof for preventing, treating and/or diagnosing estrogen receptor-associated diseases.

BACKGROUND

Estrogens are a group of hormones that are involved in many critical physiological functions in the human body. Estrogen functions include developing the female sex organs, preparing the breast and uterus for pregnancy and breast feeding after childbirth. Estrogens also play important roles in maintaining proper cardiovascular function and bone density. Estrogens are known to stimulate cell proliferation and may increase a woman's risk of developing cancers, especially breast cancer and uterus cancer.

Estrogens bind to estrogen receptors in/or on target cells to regulate cell functions. Two types of estrogen receptors were discovered in human cells (hERs), hER-α and hER-β. They share common protein structures, each possessing three independent but interacting functional domains: the N-terminal domain (A/B domain), the central DNA-binding domain (C domain), and the C-terminal ligand-binding domain (D/E/F domain). The N-terminal domain has a ligand-independent activation function (AF-1), which is involved in interaction with co-activators and transcriptional activation of target genes in the absence of ligands. The DNA binding-domain plays important roles in receptor dimerization and binding to specific DNA sequences. The C-terminal ligand binding-domain mediates ligand binding and has a ligand-dependent transactivation function (AF-2), activating gene transcription in the presence of ligands.

The full-length hER-α was identified as a 66 kDa protein and referred to as hER-α66. hER-α66 contains all three functional domains. A splice variant of hER-α66 was later discovered and named hER-α46. hER-α46 has a molecular weight of about 46 KDa and lacks the N-terminal AF-1 domain of hER-α66. Recently, a novel 36 kDa hER-α variant, hER-α36, was identified. It lacks the N-terminal AF-1 domain and the C-terminal AF-2 domain of hER-α66 (Wang et al., *Biochem. Biophys. Res. Commun.* 336, 1023-1027 (2005)).

hER-α66 is believed to mediate estrogen-stimulated cell proliferation via transcriptional activation of its target genes. Binding of estrogen to hER-α66 activates the transactivation domain of hER-α66 and thus stimulates the expression of downstream target genes and eventually leads to cell proliferation. hER-α46 was found to mediate membrane-initiated and estrogen-stimulated rapid NO synthesis (Li et al., *Proc. Natl. Acad. Sci. USA* 100: 4807-4812 (2003)). It was also shown that hER-α46, that lacks the AF-1 domain, inhibits the AF-1 activity of hER-α66 (Flouriot, G., EMBO, 19, 4688-4700, (2000)). Since hER-α36 lacks both the AF-1 and AF-2 transcriptional activation domains, it functions as a dominant-negative inhibitor of hER-α66 and hER-13 to inhibit both AF-1 and AF-2 functions of hER-α and hER-13. In addition, hER-α36 is localized primarily on the plasma membrane and mediates membrane-initiated mitogenic estrogen signaling that stimulates cell proliferation. (Wang et al., *Biochem. Biophys. Res. Commun.* 336, 1023-1027 (2005); Wang et al., *Proc. Natl. Acad. Sci. U.S.A.* 103: 9063-9068 (2006)).

Extensive studies have shown that estrogen signaling is mediated via the classic nuclear transcriptional activation pathways as well as the non-classic membrane-initiated signaling pathways. It seems that hER-α66 and hER-α46 function primarily in the nucleus while hER-α36 functions mainly through outside of the nucleus.

It was also shown that hER-α36 lacks Helix 8-12 of the ligand-binding domain of the original hER-α66, which totally changes the ligand binding specificity of hER-α36. Thus, hER-α36 may bind to different ligands from hER-α66 and hER-13.

As estrogen and estrogen receptor related diseases continue to affect many individuals, there remains an urgent need to discover novel approaches such as novel antibodies and methods useful to prevent, treat and/or diagnose such diseases.

Antibody drug conjugates (ADC) in general have been in research and development for a long time. Compared to the antibodies and the toxins alone by themselves, ADC improve the delivery of drugs and other agents to target cells, tissues and tumors to achieve higher efficacy and lower toxicity. The conjugates of mc-vc-PAB-MMAE and mc-MMAF were disclosed in US2012148610. Conjugate of MB-vc-duocarmycin was disclosed in WO2007038658. Conjugates of SMCC-DM1 and SPDB-DM4 were disclosed in US2005169933. All of the above patents are incorporated herein for reference.

SUMMARY

Provided herein are antibodies and antigen-binding fragments and the modification thereof, and pharmaceutical compositions and methods of use for treating/preventing/diagnosing conditions associated with estrogen receptor ER-α36 (SEQ ID NO. 1, Gene Accession Number BX640939).

In certain embodiments, an antibody or antigen-binding fragment provided herein specifically binds to ER-α36 but not to ER-α66 (FIG. 1(a) for ER-α66 amino acid sequence) or ER-α46 (FIG. 1(b) for ER-α46 amino acid sequence). In certain embodiments, the antibody or the antigen-binding fragment specifically binds to amino acids residues from 284 to 310 of SEQ. ID. NO: 1 from N terminal, or amino acid residues from 1 to 27 of SEQ. ID NO: 2.

In certain embodiments, an antibody or antigen-binding fragment thereof is provided that comprises a CDR selected from the group consisting of SEQ ID NO: 3, SEQ ID NO: 4, SEQ ID NO: 5, SEQ ID NO: 6, SEQ ID NO: 7, and SEQ ID NO: 8.

In certain embodiments, the antibody or antigen binding fragment thereof comprises a heavy chain variable region comprising SEQ ID NO: 6, and a light chain variable region comprising SEQ ID NO: 5.

In certain embodiments, antibody or antigen-binding fragment thereof is provided that comprises a light chain variable region comprising a member selected from the group consisting of SEQ ID NO: 3, SEQ ID NO: 4, and SEQ ID NO: 5.

In certain embodiments, the antibody or antigen binding fragment thereof comprises a light chain variable region comprising SEQ ID NO: 3, SEQ ID NO: 4, and SEQ ID NO: 5.

In certain embodiments, the light chain variable region is selected from the group consisting of:
a) the light chain variable region comprising SEQ ID NO: 9;
b) the light chain variable region comprising SEQ ID NO: 11;
c) the light chain variable region comprising SEQ ID NO: 12; and
d) the light chain variable region comprising SEQ ID NO: 13.

In certain embodiments, an antibody or antigen binding fragment thereof is provided that comprises a heavy chain variable region comprising a member selected from the group consisting of SEQ ID NO: 6, SEQ ID NO: 7, and SEQ ID NO: 8.

In certain embodiments, the antibody or antigen binding fragment thereof comprises a heavy chain variable region comprising SEQ ID NO: 6, SEQ ID NO: 7, and SEQ ID NO: 8.

In certain embodiments, the heavy chain variable region is selected from the group consisting of:
a) the light chain variable region comprising SEQ ID NO: 10;
b) the light chain variable region comprising SEQ ID NO: 14; and
c) the light chain variable region comprising SEQ ID NO: 15.

In certain embodiments, the antibody or antigen binding fragment thereof further comprises a light chain variable region comprising a LCDR selected from the group consisting of SEQ ID NO: 3, SEQ ID NO: 4, and SEQ ID NO: 5.

In certain embodiments, the light chain variable region comprises SEQ ID NO: 3, SEQ ID NO: 4, and SEQ ID NO: 5.

In certain embodiments, the light chain variable region is selected from the group consisting of:
a) the light chain variable region comprising SEQ ID NO: 9;
b) the light chain variable region comprising SEQ ID NO: 11;
c) the light chain variable region comprising SEQ ID NO: 12; and
d) the light chain variable region comprising SEQ ID NO: 13.

In certain embodiments, the antibody or antigen binding fragment thereof comprises a light chain comprising SEQ ID NO: 16, and a heavy chain of SEQ ID NO: 18.

In certain embodiments, the antibody or antigen binding fragment thereof comprises a light chain comprising SEQ ID NO: 20, and a heavy chain of SEQ ID NO: 22.

In certain embodiments, the antibody or antigen binding fragment thereof comprises a light chain selected from the group consisting of SEQ ID NO: 24, SEQ ID NO: 26, and SEQ ID NO: 28, and a heavy chain selected from the group consisting of SEQ ID NO: 30, and SEQ ID NO: 32.

In certain embodiments, an antibody or antigen-binding fragment thereof is provided which substantially binds to the same epitope to which the antibody or antigen binding fragment thereof which comprises a light chain comprising SEQ ID NO: 16, and a heavy chain of SEQ ID NO: 18, or comprises a light chain comprising SEQ ID NO: 20, and a heavy chain of SEQ ID NO: 22, specifically binds.

In certain embodiments, the epitope comprises S3, K8, R10, P16, K17, G20, N21, K22, W23, and/or F24 of SEQ ID NO: 2.

In certain embodiments, the epitope comprises G20, N21, K22, W23, and/or F24 of SEQ ID NO: 2.

In certain of the above embodiments, the antibody or antigen-binding fragment thereof is a monoclonal antibody, a polyclonal antibody, a bispecific antibody, a chimeric antibody, a humanized antibody, a recombinant antibody, a human antibody, a murine antibody, a labeled antibody, a bivalent antibody, or an anti-idiotypic antibody.

In certain of the above embodiments, the antibody or antigen-binding fragment thereof is a camelized single domain antibody, a diabody, a scFv, an scFv dimer, a BsFv, a dsFv, a (dsFv)$_2$, a dsFv-dsFv', an Fv fragment, a Fab, a Fab', a F(ab')$_2$, a ds diabody, a nanobody, a domain antibody, or a bivalent domain antibody.

In certain of the above embodiments, the antibody or antigen-binding fragment thereof further comprises an immunoglobulin constant region.

In certain embodiments, the immunoglobulin constant region is a λ light chain, κ light chain, γ1 heavy chain, γ2 heavy chain, γ3 heavy chain, or γ4 heavy chain constant region.

In certain of the above embodiments, a complex comprising an antibody or antigen-binding fragment thereof binding to hER-α36 as set forth in SEQ ID NO:1 or a fragment of hER-α36 comprising SEQ ID NO: 2.

In certain embodiments, an antibody or antigen-binding fragment is provided that specifically binds ER-α36 and/or modulates the activities of ER-α36. In certain embodiments, the antibody or antigen-binding fragment disclosed herein treats, inhibits, reduces or prevents diseases associated with ER-α36. For example, the antibody or antigen-binding fragment disclosed herein inhibits tumor growth as a function of percent tumor growth inhibition; reduces tumor size, or delays tumor growth to a specified size.

In certain embodiments, the antibodies or antigen-binding fragments bind ER-α36 with a $K_D$ of ≤1000 pM. In certain of these embodiments, the antibodies or antigen-binding fragments bind ER-α36 with a $K_D$ of ≤500 pM, in other embodiments 200 pM, ≤100 pM, ≤50 pM, ≤20 pM, ≤10 pM, or ≤1 pM.

In certain embodiments, methods are provided for inhibiting, treating, reducing or preventing diseases associated with ER-α36 in a subject in need thereof by administering to said subject a therapeutically effective amount of one or more antibodies or antigen-binding fragments disclosed herein. In certain embodiments, the antibody or antigen-binding fragment is administered at a dosage of about 0.01 mg/kg to about 100 mg/kg (e.g., about 10 mg/kg or about 5 mg/kg or less) per administration. In certain of these embodiments, the antibody or antigen-binding fragment is administered at a dosage of about 1 mg/kg or less per administration, in other embodiments about 0.5 mg/kg or less, and in still other embodiments about 0.1 mg/kg or less.

In certain embodiments, diagnostic methods are provided for determining the presence of ER-α36 protein or the progress/recession of a disease associated with ER-α36 by exposing a sample to the antibodies or antigen-binding fragments provided herein and determining the binding of the antibodies or antigen-binding fragments to the sample. For example, a kit is provided comprising one or more antibodies or antigen-binding fragments as disclosed herein.

In certain embodiments, the kit further comprises instructions for using the antibodies or antigen-binding fragments, and/or for utilizing other components of the kit.

In certain embodiments, polynucleotides are provided that encode the amino acid sequences of the antibodies or antigen-binding fragments disclosed herein. In certain other embodiments, vectors are provided that comprise these polynucleotides, and in certain other embodiments, host cells are provided that comprises these vectors. In certain embodiments, methods are provided for expressing one or more of the antibodies or antigen-binding fragments disclosed herein by culturing these host cells under conditions in which the antibodies or antigen-binding fragments encoded by the polynucleotides are expressed from a vector. In certain embodiments, the polynucleotides provided herein are operably associated with a promoter such as a CMV promoter in a vector. In certain embodiments, host cells comprising the vectors provided herein are Chinese hamster ovary cell.

In certain embodiments, pharmaceutical compositions are provided that comprise one or more antibodies or antigen-binding fragments as disclosed herein. In certain of these embodiments, the composition further comprises one or more pharmaceutical carriers. In certain of these embodiments, the one or more pharmaceutical carriers may be one or more pharmaceutically acceptable carriers including for example, diluents, antioxidants, adjuvants, excipients, or non-toxic auxiliary substances.

In certain embodiments, the use of one or more antibodies or antigen-binding fragments as provided herein in the manufacture of a medicament for treating a disease associated with ER-α36.

In certain embodiments, a method of determining the status of a condition associated with ER-α36 in a subject is provided that comprises measuring the level of ER-α36 using the antibody or antigen-binding fragment thereof.

BRIEF DESCRIPTION OF THE FIGURES

FIG. 1 shows amino acid sequences of human ERs. FIG. 1(a) shows the amino acid sequence of human ER-α66. FIG. 1(b) shows the amino acid sequence of human ER-α46.

FIG. 2 shows QC result of purified SNGmB1 antibody. Monoclonal antibody SNGmB1 (mIgG2b) was generated using hybridoma technology with recombinant ER-α36 protein as immunogen. The hybridoma was subcloned three times before its gene was cloned.

FIG. 6 illustrates immunofluorescence analysis of SNGmB1 binding to MCF7 derived mammosphere and its effect on MCF7 mammosphere formation.

FIG. 11 shows expression of ER-α36 in invasion front (A) and lymphatic metastases (B) in human tissue samples, as detected using Immunohistochemistry assay with the SNGmB1 antibody.

DETAILED DESCRIPTION

Figure 3:
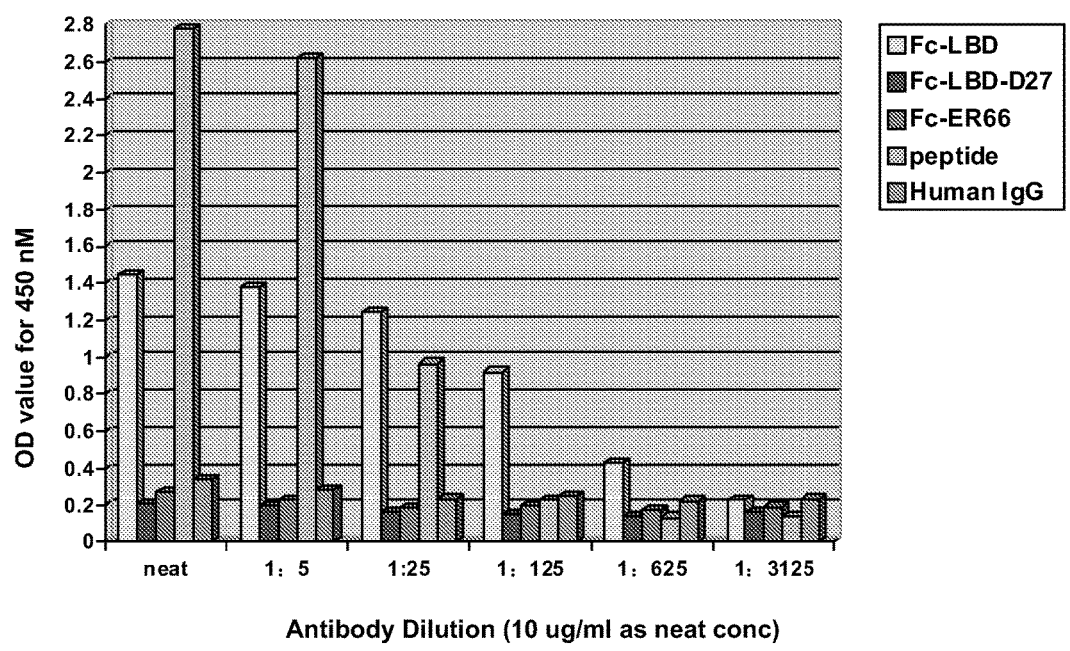
FIG. 3 shows binding specificity of SNGmB1. "Fc-LBD" represents fusion protein of Fc and ER-α36 ligand binding domain including the C-terminal 27 amino acids; "Fc-LBD-D27" represents Fc-LBD with the C-terminal 27 amino acids deleted; "Fc-ER66" represents fusion protein of Fc and ER-α66 ligand binding domain; "peptide" represents the C-terminal 27 amino acids derived from the F domain of ER-α36; "Human IgG" represents control human IgG protein; Neat=10 μg/ml.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein, including publications, patents and patent applications are incorporated herein by reference in their entirety.

The term "antibody" as used herein includes any monoclonal antibody, polyclonal antibody, multispecific antibody, or bispecific (bivalent) antibody that binds to a specific antigen. A complete antibody comprises two heavy chains and two light chains. Each heavy chain consists of a variable region and a first, second, and third constant region, while each light chain consists of a variable region and a constant region. Mammalian heavy chains are classified as $\alpha$, $\delta$, $\epsilon$, $\gamma$, and $\mu$, and mammalian light chains are classified as $\lambda$ or $\kappa$. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variables region in both chains generally contain three highly variable loops called the complementarity determining regions (CDRs) (light (L) chain CDRs including LCDR1, LCDR2, and LCDR3, heavy (H) chain CDRs including HCDR1, HCDR2, HCDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of $\alpha$, $\delta$, $\epsilon$, $\gamma$, and $\mu$ heavy chains, respectively. Several of the major antibody classes are divided into subclasses such as IgG1 ($\gamma$1 heavy chain), IgG2 ($\gamma$2 heavy chain), IgG3 ($\gamma$3 heavy chain), IgG4 ($\gamma$4 heavy chain), IgA1 ($\alpha$1 heavy chain), or IgA2 ($\alpha$2 heavy chain).

An antibody or antigen-binding fragment thereof that is "bivalent" comprises two antigen-binding sites. The two antigen binding sites may bind to the same antigen, or they may each bind to a different antigen, in which case the antibody or antigen-binding fragment is characterized as "bispecific."

The term "antigen-binding fragment" as used herein refers to an antibody fragment such as for example a diabody, a Fab, a Fab', a F(ab')$_2$, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment (e.g., a parent scFv) binds. In certain embodiments, an antigen-binding fragment may comprise one or more CDRs from a particular human antibody grafted to a framework region from one or more different human antibodies.

"Fab" with regard to an antibody refers to that portion of the antibody consisting of a single light chain (both variable and constant regions) bound to the variable region and first constant region of a single heavy chain by a disulfide bond.

"Fab'" refers to a Fab fragment that includes a portion of the hinge region.

"F(ab')$_2$" refers to a dimer of Fab'.

"Fc" with regard to an antibody refers to that portion of the antibody consisting of the second and third constant regions of a first heavy chain bound to the second and third constant regions of a second heavy chain via disulfide bonding. The Fc portion of the antibody is responsible for various effector functions such as ADCC, and CDC, but does not function in antigen binding.

"Fv" with regard to an antibody refers to the smallest fragment of the antibody to bear the complete antigen binding site. An Fv fragment consists of the variable region of a single light chain bound to the variable region of a single heavy chain.

"Single-chain Fv antibody" or "scFv" refers to an engineered antibody consisting of a light chain variable region and a heavy chain variable region connected to one another directly or via a peptide linker sequence (Houston 1988).

"Single-chain Fv-Fc antibody" or "scFv-Fc" refers to an engineered antibody consisting of a scFv connected to the Fc region of an antibody.

"Camelized single domain antibody," "heavy chain antibody," or "HCAb" refers to an antibody that contains two $V_H$ domains and no light chains (Riechmann 1999; Muyldermans 2001; WO94/04678; WO94/25591; U.S. Pat. No.

6,005,079). Heavy chain antibodies were originally derived from Camelidae (camels, dromedaries, and llamas). Although devoid of light chains, camelized antibodies have an authentic antigen-binding repertoire (Hamers-Casterman 1993; Nguyen 2002; Nguyen 2003). The variable domain of a heavy chain antibody (VHH domain) represents the smallest known antigen-binding unit generated by adaptive immune responses (Koch-Nolte 2007).

A "nanobody" refers to an antibody fragment that consists of a VHH domain from a heavy chain antibody and two constant domains, CH2 and CH3.

"Diabodies" include small antibody fragments with two antigen-binding sites, wherein the fragments comprise a $V_H$ domain connected to a $V_L$ domain in the same polypeptide chain ($V_H$-$V_L$ or $V_H$-$V_L$) (see, e.g., Holliger 1993; EP404097; WO93/11161). By using a linker that is too short to allow pairing between the two domains on the same chain, the domains are forced to pair with the complementary domains of another chain, thereby creating two antigen-binding sites. The antigen-binding sites may target the same of different antigens (or epitopes).

A "domain antibody" refers to an antibody fragment containing only the variable region of a heavy chain or the variable region of a light chain. In certain instances, two or more $V_H$ domains are covalently joined with a peptide linker to create a bivalent or multivalent domain antibody. The two $V_H$ domains of a bivalent domain antibody may target the same or different antigens.

In certain embodiments, a "(dsFv)$_2$" comprises three peptide chains: two $V_H$ moieties linked by a peptide linker and bound by disulfide bridges to two $V_L$ moieties.

In certain embodiments, a "bispecific ds diabody" comprises $V_{H1}$-$V_{L2}$ (linked by a peptide linker) bound to $V_{L1}$-$V_{H2}$ (also linked by a peptide linker) via a disulfide bridge between $V_{H1}$ and $V_{L1}$.

In certain embodiments, a "bispecific dsFv" or dsFv-dsFv'" comprises three peptide chains: a $V_{H1}$-$V_{H2}$ moiety wherein the heavy chains are linked by a peptide linker (e.g., a long flexible linker) and bound to $V_{L1}$ and $V_{L2}$ moieties, respectively, via disulfide bridges, wherein each disulfide paired heavy and light chain has a different antigen specificity.

In certain embodiments, an "scFv dimer" is a bivalent diabody or bivalent ScFv (BsFv) comprising $V_H$-$V_L$ (linked by a peptide linker) dimerized with another $V_H$-$V_L$ moiety such that $V_H$'s of one moiety coordinate with the $V_L$'s of the other moiety and form two binding sites which can target the same antigens (or eptipoes) or different antigens (or eptipoes). In other embodiments, an "scFv dimer" is a bispecific diabody comprising $V_{H1}$-$V_{L2}$ (linked by a peptide linker) associated with $V_{L1}$-$V_{H2}$ (also linked by a peptide linker) such that $V_{H1}$ and $V_{L1}$ coordinate and $V_{H2}$ and $V_{L2}$ coordinate and each coordinated pair has a different antigen specificity.

The term "epitope" as used herein refers to the specific group of atoms or amino acids on an antigen to which an antibody binds. Two antibodies may bind the same epitope within an antigen if they exhibit competitive binding for the antigen. For example, if an antibody or antigen-binding fragment as disclosed herein competes with SNGmB1 for ER-α36 binding, the antibody may be, but is not necessarily, considered to bind the same epitope as SNGmB1.

"ER" as used herein refers to one of several known estrogen receptors, ER-α66, ER-α46, or ER-α36. The full-length human ER-α identified as a 66 kDa protein having 595 amino acids is referred as hER-α66 (FIG. 1(a)) hER-α66 is composed of three independent but interacting functional domains: the N-terminal A/B domain, the C or DNA-binding domain, and the D/E/F or ligand-binding domain (See U.S. application Ser. No. 10/591,199 which is incorporated by reference herein). The N-terminal domain of ER α66 encodes a ligand-independent activation function (AF-1), a region involved in interaction with co-activators, and transcriptional activation of target genes. The DNA-binding domain or C domain contains a two zinc-finger structure, which plays an important role in receptor dimerization and binding to specific DNA sequences. The C-terminal D/E/F domain is a ligand-binding domain that mediates ligand binding, receptor dimerization, nuclear translocation, and a ligand-dependent transactivation function (AF-2). The relative contributions that both AF-1 and AF-2 exert on transcriptional control vary in a cell-specific and DNA promoter-specific manner (Berry et. al., EMBO J., 9:2811 (1990) and Tzukerman et. al., Mol. Endocrin., 8:21 (1994)). Human ER-α46 (hER-α46, FIG. 1(b)) is a splice variant of hER-α66, has a molecular weight of about 46 KDa containing 412 amino acids, and lacks the N-terminal AF-1 domain of hER-α66. Human ER-α36 (hER-α36 as set forth in SEQ ID NO:1) is a 36 kDa hER-α variant which lacks the N-terminal AF-1 domain and the C-terminal AF-2 domain of hER-α66 (Wang et al., Biochem. Biophys. Res. Commun. 336, 1023-1027 (2005), U.S. application Ser. No. 10/591,199, WO2005/087811). However, hER-α36 has a unique addition of 27 amino acid residues to its C-terminus when compared to hER-α66 or hER-α46. The 27 amino acid residues are amino acids residues from 284 to 310 of SEQ. ID. NO. 1, or amino acid residues from 1 to 27 of SEQ. ID NO. 2.

"ER activities" as used herein includes intracellular events induced by ER (e.g., hER-α36), such as receptor phosphorylation (e.g., tyrosine phosphorylation), binding of intracellular signaling molecules to the receptor or to other intracellular signaling molecules, the initiation of a signaling cascade, and/or the initiation of a biological response (e.g., induction of gene expression and changes in the physiology or development (e.g., proliferation) of the cell having the ER (e.g., hER-α36)).

"Cancer" or "cancerous condition" as used herein refers to any medical condition mediated by neoplastic or malignant cell growth, proliferation, or metastasis, and includes both solid cancers and non-solid cancers such as leukemia. "Tumor" as used herein refers to a solid mass of neoplastic and/or malignant cells.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof. With regard to cancer, "treating" or "treatment" may refer to inhibiting or slowing neoplastic or malignant cell growth, proliferation, or metastasis, preventing or delaying the development of neoplastic or malignant cell growth, proliferation, or metastasis, or some combination thereof. With regard to a tumor, "treating" or "treatment" includes eradicating all or part of a tumor, inhibiting or slowing tumor growth and metastasis, preventing or delaying the development of a tumor, or some combination thereof.

The term "specifically binds" as used herein refers to a non-random binding reaction between two molecules, such as for example between an antibody and an antigen. In certain embodiments, an antibody or antigen-binding fragment that specifically binds an antigen binds the antigen with a binding affinity ($K_D$) of $\leq 10^{-6}$ M (e.g., $\leq 5 \times 10^{-7}$ M, $\leq 2 \times 10^{-7}$ M, $\leq 10^{-7}$ M, $\leq 5 \times 10^{-8}$ M, $\leq 2 \times 10^{-8}$ M, $\leq 10^{-8}$ M, $\leq 5 \times 10^{-9}$ M, $\leq 2 \times 10^{-9}$ M, $\leq 10^{-9}$ M, $10^{-10}$ M). $K_D$ as used herein refers to the ratio of the dissociation rate to the association rate ($k_{off}/k_{on}$), may be determined using methods known in the art (e.g., using Biacore or Kinexa techniques).

An "isolated" substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state.

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating.

The phrase "host cell" as used herein refers to a cell into which an exogenous polynucleotide and/or a vector has been introduced. A host cell may be selected from a variety of cell types, including for example bacterial cells such as *E. coli* or *B. subtilis* cells, fungal cells such as yeast cells or *Aspergillus* cells, insect cells such as *Drosophila* S2 or *Spodoptera* Sf9 cells, or animal cells such as fibroblasts, CHO cells, COS cells, NSO cells, HeLa cells, BHK cells, HEK 293 cells, or human cells.

A "disease associated with or related to ER or ER-α36" as used herein refers to any condition that is caused by, exacerbated by, or otherwise linked to increased or decreased activities of ER (e.g., ER-α36). Such conditions include cancers mediated by cells that are dependent on of ER (e.g., ER-α36) for growth, proliferation, or metastasis, diseases of the bone such as bone loss, bone fractures or osteoporosis, and inflammatory conditions such as for example rheumatoid arthritis, psoriasis, scleroderma, chronic obstructive pulmonary disease or asthma.

The ability to "block binding" or "compete for binding" as used herein refers to the ability of an antibody or antigen-binding fragment to inhibit the binding interaction between two molecules to any detectable agree. In certain embodiments, an antibody or antigen-binding fragment that blocks binding between two molecules inhibits the binding interaction between the two molecules by at least 50%. In certain embodiments, this inhibition may be greater than 60%, in certain embodiments greater than 70%, in certain embodiments greater than 80%, and in certain embodiments greater than 90%. In certain embodiments, the binding interaction being inhibited may be that of SNGmB1 to hER-α36.

The term "therapeutically effective amount" or "effective dosage" as used herein refers to the dosage or concentration of a drug effective to treat a disease or condition associated with hER-α36. For example, with regard to the use of the antibodies or antigen-binding fragments disclosed herein to treat cancer, a therapeutically effective amount is the dosage or concentration of the antibody or antigen-binding fragment capable of eradicating all or part of a tumor, inhibiting or slowing tumor growth, inhibiting growth or proliferation of cells mediating a cancerous condition, inhibiting tumor cell metastasis, ameliorating any symptom or marker associated with a tumor or cancerous condition, preventing or delaying the development of a tumor or cancerous condition, or some combination thereof.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

Anti-hER-α36 Antibody

In one aspect, the present disclosure provides anti-hER-α36 antibodies and the antigen-binding fragments thereof that specifically bind to the amino acid residues 284-310 of SEQ ID NO: 1, i.e. the 27 amino acid fragment shown in SEQ ID NO: 2.

The amino acids sequences of SEQ ID NO: 1, and SEQ ID NO: 2 are listed below.

```
The amino acid sequence of SEQ ID NO: 1:
Met Ala Met Glu Ser Ala Lys Glu Thr Arg Tyr Cys Ala Val Cys Asn Asp Tyr Ala Ser Gly Tyr His Tyr Gly Val Trp Ser Cys Glu Gly Cys Lys Ala Phe Phe Lys Arg Ser Ile Gln Gly His Asn Asp Tyr Met Cys Pro Ala Thr Asn Gln Cys Thr Ile Asp Lys Asn Arg Arg Lys Ser Cys Gln Ala Cys Arg Leu Arg Lys Cys Tyr Glu Val Gly Met Met Lys Gly Gly Ile Arg Lys Asp Arg Arg Gly Gly Arg Met Leu Lys His Lys Arg Gln Arg Asp Asp Gly Glu Gly Arg Gly Glu Val Gly Ser Ala Gly Asp Met Arg Ala Ala Asn Leu Trp Pro Ser Pro Leu Met Ile Lys Arg Ser Lys Lys Asn Ser Leu Ala Leu Ser Leu Thr Ala Asp Gln Met Val Ser Ala Leu Leu Asp Ala Glu Pro Pro Ile Leu Tyr Ser Glu Tyr Asp Pro Thr Arg Pro Phe Ser Glu Ala Ser Met Met Gly Leu Leu Thr Asn Leu Ala Asp Arg Glu Leu Val His Met Ile Asn Trp Ala Lys Arg Val Pro Gly Phe Val Asp Leu Thr Leu His Asp Gln Val His Leu Leu Glu Cys Ala Trp Leu Glu Ile Leu Met Ile Gly Leu Val Trp Arg Ser Met Glu His Pro Gly Lys Leu Leu Phe Ala Pro Asn Leu Leu Leu Asp Arg Asn Gln Gly Lys Cys Val Glu Gly Met Val Glu Ile Phe
```

-continued

Asp Met Leu Leu Ala Thr Ser Ser Arg Phe Arg Met

Met Asn Leu Gln Gly Glu Glu Phe Val Cys Leu Lys

Ser Ile Leu Leu Leu Asn Ser Gly Ile Ser His Val

Glu Ala Lys Lys Arg Ile Leu Asn Leu His Pro Lys

Ile Phe Gly Asn Lys Trp Phe Pro Arg Val

The amino acid sequence of SEQ ID NO: 2
Gly Ile Ser His Val Glu Ala Lys Lys Arg Ile Leu Asn Leu His Pro Lys Ile Phe Gly Asn Lys Trp Phe Pro Arg Val An "anti-hER-α36" antibody as used herein refers to an antibody that blocks binding of hER-α36 receptor with its ligand, or that competes with the ligand for binding with hER-α36 receptor.

In certain embodiments, the anti-hER-α36 antibodies and the antigen-binding fragments thereof specifically binds hER-α36 (i.e. SEQ ID NO: 1) or an hER-α36 fragment comprising SEQ ID NO: 2, with a binding affinity ($K_D$) of $\leq 10^{-6}$ M (e.g., $\leq 5\times 10^{-7}$ M, $\leq 2\times 10^{-7}$ M, $\leq 10^{-7}$ M, $\leq 5\times 10^{-8}$ M, $\leq 2\times 10^{-8}$ M, $\leq 10^{-8}$ M, $\leq 5\times 10^{-9}$ M, $\leq 2\times 10^{-9}$ M, $\leq 10^{-9}$ M, $\leq 5\times 10^{-10}$ M, $\leq 2\times 10^{-10}$ M, $\leq 5\times 10^{-11}$ M, $\leq 5\times 10^{-11}$ M, or $\leq 10^{-11}$ M). In certain embodiments, the binding affinity ranges from $10^{-11}$ M to $10^{-8}$ M, $10^{-11}$ M to $10^{-9}$ M, $10^{-11}$ M to $10^{-8}$ M, $10^{-11}$ M to $10^{-7}$ M, $10^{-11}$ M to $10^{-6}$ M, $10^{-10}$ M to $10^{-8}$ M, $10^{-10}$ M to $10^{-9}$ M, $10^{-10}$ M to $10^{-8}$ M, $10^{-10}$ M to $10^{-7}$ M, or $10^{-10}$ M to $10^{-6}$ M.

The binding affinity can be represented by $K_D$ value, which is calculated as the ratio of dissociation rate to association rate ($k_{off}/k_{on}$) when the binding between the antigen and the antigen-binding molecule reaches equilibrium. The dissociation rate ($k_{off}$) measured at the binding equilibrium may also be used when measurement of $k_{on}$ is difficult to obtain, for example, due to aggregation of antigens. The antigen-binding affinity (e.g. $K_D$ or $k_{off}$) can be appropriately determined using suitable methods known in the art, including, for example, Biacore (see, for example, Murphy, M. et al, Current protocols in protein science, Chapter 19, unit 19.14, 2006) and Kinexa techniques (see, for example, Darling, R. J., et al, Assay Drug Dev. Technol., 2(6): 647-657 (2004)).

In certain embodiments, the antibodies and the fragments thereof provided herein antagonize one or more of the ER activities of hER-α36. Such antibodies and the fragments thereof do not stimulate one or more ER activities when bound to hER-α36, and/or they can compete with ER ligands or agonists for receptor binding such that the stimulation of ER activity by the ER ligands or agonists can be inhibited or antagonized. The activity of the antibodies and the fragments thereof on the ER activities can be measured using assays well-known in the art, for example, by detecting receptor phosphorylation, by detecting inhibition of binding of an ER ligand or agonist, by detecting one or more biological responses of the hER-α36 receptor. Exemplary methods or assays are described in detail in WO05/087811, which are incorporated herein in its entirety.

In certain embodiments, the anti-hER-α36 antibodies and its antigen-binding fragments thereof can be internalized to a cell expressing hER-α36. The internalization of the antibodies can be measured by, for example, incubating cells expressing hER-α36 with a labeled anti-hER-α36 antibody for a certain period of time and detect the presence of the labeled antibody inside the cells (e.g. with a fluorescent microscope, or FACS analysis).

In certain embodiments, the anti-hER-α36 antibodies and the antigen-binding fragments thereof possess anti-tumor activity in vitro and/or in vivo. The antibodies and the fragments thereof can inhibit tumor cell growth and/or induce tumor cell apoptosis. The anti-tumor activity can be detected in vitro using a tumor cell culture, or in vivo using an animal model.

Antibodies derived from SNGmB1

Provided herein are anti-hER-α36 antibodies and the antigen-binding fragments thereof, comprising at least one (e.g. at least 2, 3, 4, 5 or all 6) of the CDRs of SNGmB1 antibody.

"SNGmB1 antibody" as used herein, refers to a mouse monoclonal antibody comprising a light chain having an amino acid sequence of SEQ ID NO: 16, and a heavy chain having an amino acid sequence of SEQ ID NO: 18. The nucleotide sequences encoding for the light chain and the heavy chain of the SNGmB1 antibody are also provided below as SEQ ID NO: 17 and SEQ ID NO: 19. The amino acid sequences for the light chain and the heavy chain are set forth below, in which the CDR regions are bold and underlined, and the constant regions are bold and italic.

The amino acid sequence of light chain of SNGmB1 (SEQ ID NO: 16):

ETTVTQSPASLSMTIGEKVTIRCITSTDIDDDMNWY
RKKPGQPPKLLIS
                                                         LCDR1

EGNTLRPGVPSRFSSSGYGTDFVFTIENMLSEDVADYYCLQSDNLPLTFGA
GTKLELK*RADAAPTVSIF*
LCDR2                                                     LCDR3

*PPSSEQLTSGGASVVCFLNNFYPKDINVKWKIDGSERQNGVLNSWTDQDSK*

*DSTYSMSSTLTLTKDEYERHNSYTCEATHKTSTSPIVKSFNRNEC*

The amino acid sequence of heavy chain of SNGmB1 (SEQ ID NO:18):

QAYLQQSGAELVRPGASVKMSCKASGYTFTSHNMHW
IKQTPRQGLEWIG
                                                    HCDR1

AIHPVNGDTAYNQKFKGKATLTVDKSSSTAYLQLSSLTSEESAVYFCAREG
YGSVDYWGQGTTLTVSS*A*
HCDR2
HCDR3

*KTTPPSVYPLAPGCGDTTGSSVTLGCLVKGYFPESVTVTWNSGSLSSSVHT*

*FPALLQSGLYTMSSSVTVPSSTWPSQTVTCSVAHPASSTTVDKKLEPSGPI*

*STINPCPPCKECHKCPAPNLEGGPSVFIFPPNIKDVLMISLTPKVTCVVVD*

*VSEDDPDVQISWFVNNVEVHTAQTQTHREDYNSTIRVVSTLPIQHQDWMSG*

*KEFKCKVNNKDLPSPIERTISKIKGLVRAPQVYILPPPAEQLSRKDVSLTC*

*LVVGFNPGDISVEWTSNGHTEENYKDTAPVLDSDGSYFIYSKLNMKTSKWE*

*KTDSFSCNVRHEGLKNYYLKKTISRSPGK*

The nucleotide sequence encoding light chain of the mouse antibody SNGmB1 (SEQ ID NO:17):

5'-GAGACCACAGTGACCCAGAGCCCCGCCAGCCTCAGCATGACAAT

CGGCGAGAAGGTGACCATCAGGTGCATCACATCCACCGACATCGACG

ACGACATGAACTGGTACAGGAAGAAGCCCGGCCAACCCCCCAAACTC

CTCATCAGCGAGGGCAACACACTCAGGCCTGGCGTCCCCTCCAGATT

CTCCAGCAGCGGCTACGGCACCGACTTCGTCTTCACCATCGAGAACA

TGCTGTCCGAGGACGTGGCCGACTACTACTGCCTGCAGTCCGATAAC

CTGCCCCTGACATTCGGCGCCGGCACCAAGCTCGAGCTGAAAAGGGC

CGACGCCGCCCCTACCGTCAGCATTTTCCCCCCTTCCAGCGAGCAAC

TGACAAGCGGAGGCGCCAGCGTGGTGTGCTTCCTCAACAACTTCTAC

CCCAAGGACATCAACGTGAAGTGGAAGATCGACGGCAGCGAGAGACA

AAACGGAGTGCTGAACAGCTGGACCGATCAGGACAGCAAGGACAGCA

CCTACAGCATGAGCTCCACCCTCACACTGACCAAGGACGAATACGAG

AGGCACAACTCCTACACCTGCGAGGCCACACACAAGACAAGCACCTC

CCCCATCGTCAAGAGCTTCAACAGGAACGAGTGCTGA-3'

The nucleotide sequence encoding heavy chain of the mouse antibody SNGmB1 (SEQ ID NO:19)

5'-CAGGCCTACCTGCAACAAAGCGGCGCTGAGCTCGTCAGGCCTGG

AGCTAGCGTGAAGATGTCCTGTAAGGCCAGCGGCTACACCTTTACCA

GCCACAACATGCACTGGATCAAGCAGACCCCTAGGCAGGGACTGGAA

TGGATCGGAGCCATTCACCCCGTGAACGGAGATACCGCTTATAACCA

GAAGTTCAAGGGCAAGGCTACCCTGACCGTCGACAAGTCCTCCTCCA

CAGCCTATCTGCAGCTCAGCTCCCTGACCAGCGAAGAGAGCGCCGTC

TACTTTTGCGCCAGAGAAGGCTACGGCAGCGTGGATTACTGGGGCCA

GGGAACCACCCTCACCGTGAGCTCGGCCAAGACCACCCCTCCTAGCG

TCTACCCTCTGGCTCCCGGCTGTGGAGACACCACCGGAAGCTCCGTC

ACCCTGGGATGTCTGGTCAAGGGCTACTTCCCTGAGTCCGTGACCGT

GACCTGGAACTCCGGCTCCCTGAGCAGCTCCGTGCACACCTTCCCCG

CTCTGCTGCAGTCCGGCCTGTACACCATGAGCTCCAGCGTCACAGTG

CCCTCCAGCACCTGGCCTTCCCAGACAGTGACCTGCAGCGTGGCCCA

CCCTGCTTCCAGCACCACAGTCGACAAAAAGCTGGAGCCTAGCGGCC

CTATTTCCACCATCAACCCCTGCCCCCCCTGCAAGGAGTGCCATAAG

TGTCCTGCCCCTAATCTCGAGGGCGGACCCAGCGTGTTCATCTTCCC

CCCCAACATCAAAGACGTCCTGATGATCTCCCTGACACCCAAGGTGA

CATGCGTCGTCGTCGACGTGAGCGAAGACGACCCCGACGTGCAAATC

TCCTGGTTCGTGAACAACGTGGAGGTGCACACAGCCCAGACCCAAAC

CCACAGAGAGGACTACAACAGCACCATTAGGGTGGTCAGCACACTCC

CCATCCAACACCAGGACTGGATGTCCGGCAAGGAGTTTAAGTGCAAG

GTCAACAACAAGGACCTGCCCAGCCCCATCGAGAGGACCATCTCCAA

GATTAAGGGCCTGGTGAGGGCTCCTCAGGTGTATATCCTCCCCCCCC

CTGCTGAACAGCTGTCCAGAAAAGACGTCAGCCTGACCTGCCTGGTC

GTCGGATTCAATCCCGGAGACATCTCCGTCGAATGGACCAGCAACGG

ACACACAGAGGAGAACTACAAGGACACAGCCCCTGTCCTGGACTCCG

ACGGCTCCTACTTCATCTACTCCAAGCTGAATATGAAGACCAGCAAG

TGGGAGAAGACCGACTCCTTCAGCTGTAACGTGAGGCACGAGGGCCT

CAAGAACTACTATCTGAAGAAGACAATCTCCAGGAGCCCCGGCAAGT

GA-3'

The CDR sequences of SNGmB1 antibody are set forth in Table 1.

TABLE 1

| CDR | Sequence | SEQ ID NO. |
| --- | --- | --- |
| LCDR1 | ITSTDIDDDMN | SEQ ID NO: 3 |
| LCDR2 | EGNTLRP | SEQ ID NO: 4 |
| LCDR3 | LQSDNLPLT | SEQ ID NO: 5 |
| HCDR1 | SHNMH | SEQ ID NO: 6 |
| HCDR2 | AIHPVNGDTAYNQKFKG | SEQ ID NO: 7 |
| HCDR3 | EGYGSVDY | SEQ ID NO: 8 |

In certain embodiments, the anti-hER-α36 antibodies and antigen-binding fragments provided herein comprises at least one CDR (or at least two, three, four, five or six) selected from SEQ ID NOs: 3-8. CDRs are known to be responsible for antigen binding, however, it has been found that not all of the 6 CDRs are indispensible for the antigen binding. In other words, it is possible to replace one or more CDRs in SNGmB1 antibody yet substantially retain the binding affinity to hER-α36.

In certain embodiments, the anti-hER-α36 antibodies and the antigen-binding fragments provided herein comprise SEQ ID NO: 8 (i.e. the heavy chain CDR3 sequence of SNGmB1 antibody). Heavy chain CDR3 regions are located at the center of the antigen-binding site, and therefore are believed to make the most contact with antigen and provide the most free energy to the affinity of antibody to antigen. It is also believed that the heavy chain CDR3 is by far the most diverse CDR of the antigen-binding site in terms of length, amino acid composition and conformation by multiple diversification mechanisms (Tonegawa S. Somatic generation of antibody diversity. Nature. 302:575-81). The diversity in the heavy chain CDR3 is sufficient to produce most antibody specificities (Xu J L, Davis M M. Diversity in the CDR3 region of V(H) is sufficient for most antibody specificities. Immunity. 13:37-45) as well as desirable antigen-binding affinity (Schier R, etc. Isolation of picomolar affinity anti-c-erbB-2 single-chain Fv by molecular evolution of the complementarity determining regions in the center of the antibody binding site. J Mol Biol. 263:551-67).

In certain embodiments, the anti-hER-α36 antibodies and antigen-binding fragments provided herein comprises a heavy chain variable region which comprises any of the 3 HCDRs of SNGmB1 antibody, i.e., comprising any of SEQ ID NOs: 6-8; and/or comprises a light chain variable region which comprises any of the 3 LCDRs of SNGmB1 antibody, i.e., comprising any of SEQ ID NOs: 3-5.

In certain embodiments, the anti-hER-α36 antibodies and antigen-binding fragments provided herein comprises a heavy chain variable region which comprises SEQ ID NOs:

6, 7 and 8; and/or comprises a light chain variable region which comprises SEQ ID NOs: 3, 4, and 5.

In certain embodiments, the anti-hER-α36 antibodies and antigen-binding fragments provided herein comprise a heavy chain variable region of SNGmB1 antibody, i.e., SEQ ID NO: 10, and/or comprises a light chain variable region of SNGmB1 antibody, i.e., SEQ ID NO: 9. In certain embodiments, the anti-hER-α36 antibody is SNGmB1 antibody, comprising a light chain of SEQ ID NO: 16, and a heavy chain of SEQ ID NO: 18.

The CDR regions, the light chain variable regions, and the heavy chain variable regions of the SNGmB1 antibody can be grafted to other framework regions or constant regions according to methods known in the art to render a camelized single domain antibody, a diabody, a BsFv, an scFv dimer, a dsFv, a (dsFv)$_2$, a dsFv-dsFv', an Fv fragment, a Fab, a Fab', a F(ab')$_2$, a ds diabody, a nanobody, a domain antibody, a bivalent domain antibody, or a full antibody. The antibodies disclosed herein can be a monoclonal antibody, a recombinant antibody, a bispecific antibody, a humanized antibody, a chimeric antibody, a labeled antibody, a bivalent antibody, an anti-idiotypic antibody, or a fully human antibody.

Chimeric and/or Humanized Antibody

In certain embodiments, the anti-hER-α36 antibodies and antigen-binding fragments are chimeric. "Chimeric" as used herein, refers to a molecule comprising at least two moieties derived from different species. For example, a chimeric antibody may have at least one non-human sequence and a human sequence. In certain embodiments, the chimeric antibodies and antigen-binding fragments thereof comprise at least one CDR from mouse, and at least one constant region and/or framework region from non-mouse species (e.g. human).

The chimeric antibodies and antigen-binding fragments retain the binding specificity to hER-α36, and preferably, retain the binding affinity to hER-α36 (e.g. no less than 60%, no less than 70%, no less than 80%, no less than 90%, or no less than 95% than that of the SNGmB1 antibody), and/or retain the biological activities on hER-α36 (e.g. antagonizing activity).

In certain embodiments, the chimeric antibodies and antigen-binding fragments thereof comprise at least one of SEQ ID Nos: 3-8 and a human derived antibody scaffold. In certain embodiments, the chimeric antibodies and antigen-binding fragments thereof comprise a heavy chain variable region which comprises all of SEQ ID NOs: 6-8; and/or comprises a light chain variable region which comprises all of SEQ ID NOs: 3-5, grafted on a human-derived antibody scaffold.

In certain embodiments, the chimeric antibodies and antigen-binding fragments thereof comprise a heavy chain variable region of SEQ ID NO: 10, and/or comprises a light chain variable region of SEQ ID NO: 9, grafted on a human-derived antibody scaffold.

In certain embodiments, the chimeric antibody comprises a light chain having an amino acid sequence of SEQ ID NO: 20, and a heavy chain having an amino acid sequence of SEQ ID NO: 22. In certain embodiments, the chimeric antibody comprises a light chain encoded by a polynucleotide sequence of SEQ ID NO: 21, and a heavy chain encoded by a polynucleotide sequence of SEQ ID NO: 23.

Chimeric antibodies and antigen-binding fragments can be produced using recombinant methods, for example, as described by Morrison et al, in U.S. Pat. No. 5,807,715; by Cabilly et al. in U.S. Pat. No. 4,816,567; by Boss et al. in U.S. Pat. No. 4,816,397; Morrison, Science 229 (4719): 1202-1207 (1985); Morrison, Proc. Natl. Acad. Sci. U.S.A. 81:6851-6855 (1984), which are all incorporated herein by reference. In general, a DNA molecule encoding for a variable region of one species are ligated in-frame with another DNA molecule encoding for a constant region of another species, and the resulting DNA encoding the chimeric antibody chain are transfected into a cell to allow the expression, and the light and the heavy chains are optionally assembled in the cell to produce the chimeric antibodies or antigen-binding fragments thereof.

The chimeric anti-hER-α36 antibodies and the antigen-binding fragments thereof can be humanized. By "humanized" is meant a non-human antibody is modified to increase the sequence homology to that of a human antibody, such that the antigen-binding properties are retained yet the immunogenicity to human is reduced.

In certain embodiments, the humanized antibodies and the antigen-binding fragments thereof comprise one or more antigen-binding sequence(s) derived from the SNGmB1 antibody, grafted to a human-derived antibody scaffold. "Human-derived" as used herein, means that the antibody scaffold is fully human, or substantially from human except for a few mutations or modifications, which are introduced for example to provide for improved binding affinity, provide for conjugation sites, formation of additional disulfide bonds or for any other suitable purposes. In certain embodiments, a human-derived antibody scaffold has reduced immunogenicity or no immunogenicity in a human, relative to a non-human derived antibody such as a murine antibody.

One or more of the CDRs and/or the variable regions of SNGmB1 antibody can be grafted to a human-derived antibody or the fragment thereof. For example, the CDR(s) of SNGmB1 antibody can be grafted to a human framework region in a human-derived antibody, such that the CDR from SNGmB1 locates in replacement of the corresponding CDR on the human-derived antibody. For another example, the variable region(s) of SNGmB1 antibody can be grafted to a corresponding constant region of a human-derived antibody.

In certain embodiments, the CDRs of the SNGmB1 antibody are grafted to human framework regions. Certain amino acid residues of the human framework regions can be substituted with the corresponding residues from the SNGmB1 antibody, such that the antigen-binding regions on the humanized antibody would more closely approximate the murine antibody structure. Examples of such amino acid residues include, without limitation, V4, P44, L46, S49, and/or S64 of the light chain, and T28, L81 of the heavy chain, of the humanized antibody variable region (see Table 2).

In certain embodiments, the humanized chimeric antibodies and antigen-binding fragments thereof comprise a heavy chain variable region selected from SEQ ID NOs: 14 and 15, and/or comprises a light chain variable region selected from SEQ ID NOs: 11, 12, and 13, grafted to human-derived constant regions. Sequences of the humanized variable regions are provided in the below Table 2, in which the substituted amino acid residues in human framework regions are shown in a larger size.

In certain embodiments, the humanized chimeric antibody comprises a light chain having an amino acid sequence selected from SEQ ID NO: 24, 26, and 28, and a heavy chain having an amino acid sequence selected from SEQ ID NO: 30 and 32. In certain embodiments, the chimeric antibody comprises a light chain encoded by a nucleotide sequence selected from SEQ ID NO: 25, 27, and 29, and a heavy chain encoded by a nucleotide sequence selected from SEQ ID NO: 31 and 33.

TABLE 2

Humanized antibody variable regions

| Antibody | Variable Region | Sequence |
|---|---|---|
| SNGHZDC01 | LCVR | ETTVTQSPAFMSATPGDKVNISCITSTDIDDDMNWYQQKPGEAPILIISEGNTLRPGIPPRFSSSGYGTDFILTINNIESEDAAYYFCLQSDNLPLTFGQGTKLEIK (SEQ ID NO: 11) |
| SNGHZDC02 | LCVR | ETTVTQSPAFMSATPGDKVNISCITSTDIDDDMNWYQQKPGEAPILIISEGNTLRPGIPPRFSSSGYGTDFTLTINNIESEDAAYYFCLQSDNLPLTFGQGTKLEIK (SEQ ID NO: 12) |
| SNGHZDC03 | LCVR | ETTVTQSPAFMSATPGDKVNISCITSTDIDDDMNWYQQKPGEAPILIISEGNTLRPGIPPRFSSGYGTDFTLTINNIESEDAAYYFCLQSDNLPLTFGQGTKLEIK (SEQ ID NO: 13) |
| SNGHZDC05 | HCVR | QVQLVQSGAEVKKPGASVKVSCKASGYTFTSHNMHWVRQAPGQGLEWIGAIHPVNGDTAYNQKFKGKATLTVDKSTSTAYLELSSLRSEDTAVYYCAREGYGSVDYWGQGTLVTVSS (SEQ ID NO: 14) |
| SNGHZDC06 | HCVR | QVQLVQSGAEVKKPGASVKVSCKASGYTFTSHNMHWVRQAPGQGLEWIGAIHPVNGDTAYNQKFKGKATLTVDKSTSTAYMELSSLRSEDTAVYYCAREGYGSVDYWGQGTLVTVSS (SEQ ID NO: 15) |

Various methods known in the art can be used for humanization of a non-human antibody, for example, those described in, Lo. B, Antibody Engineering: Methods and Protocols, published by Springer, 2004, page 135-159; Padlan, Mol. Immunol. 28: 489-498 (1991); Sato et al. Mol. Immunol. 31 (5): 371-381 (1994); Kettleborough et al. Protein Eng. 4(7): 773-783 (1991); and Presta, L., Advanced Drug Delivery Reviews, 58 (2006) 640-656.

Affinity Variants

The present disclosure further provides antibodies and antigen-binding fragments with enhanced properties (e.g., increased affinity, increased half-life, improved compatibility to conjugation, etc), which comprise one or more amino acid substitutions, additions or deletions in one or more CDR sequences or the heavy or the light chain variable regions of the SNGmB1 antibody, or in the heavy or the light chain constant regions.

In certain embodiments, the antibodies or antigen-binding fragments with such amino acid substitution(s) retain the binding specificity and the binding affinity to hER-α36, and preferably, have improved binding affinity to hER-α36. They can be generated by random or targeted mutagenesis of the amino acid sequence and subsequent binding and functional assays. Antibodies and antigen-binding fragments generated in this manner may be screened for binding to ER-α36 in order to identify antibodies with ER-α36 binding characteristics. Antibodies with favorable binding characteristics may be subjected to one or more functional assays to determine their ability to, for example, inhibit cancer cell growth or proliferation in vitro or tumor growth in vivo.

NNAA Variants

In certain embodiments, the anti-hER36 antibodies and the antigen-binding fragments therefore comprises one or more non-natural amino acid (NNAA) substitution. "Non-natural amino acid" or "NNAA" as used herein refers to any amino acid, including a modified amino acid and/or an amino acid analog, that is not one of the 20 standard amino acids (i.e. glycine, alanine, valine, leucine, isoleucine, serine, cysteine, threonine, methionine, proline, phenylalanine, tyrosine, tryptophan, histidine, lysine, arginine, aspartate, glutamate, asparagine, and glutamine).

NNAAs can contain a variety of functional groups or reactive groups, which can provide for additional functions and/or reactivity. For example, NNAAs suitable for incorporation in the antibodies and the antigen-binding fragments may be a photocaged and/or photoisomerizable amino acid (e.g. p-azophenyl-phenylalanine), glycosylated amino acid (e.g. N-acetyl-L-glucosaminyl-L-serine), radiolabled amino acid, keto-containing amino acid (e.g. pyrrolysine), aldehyde-containing amino acid, such as formylglycine (Redwood Bioscience's SMARTAG™), heavy atom substituted amino acid (e.g. p-iodophenylalanine), chemically cleavable and/or photocleavable amino acid, redox-active amino acid (3-amino-L-tyrosine), or photoactivatable amino acid (e.g. p-azido-Lphenylalanine and p-benzoyl-L-phenylalanine). Reviews of NNAA can be found at, for example, Xie, J. et al, Current Opinion in Chemical Biology 2005, 9:548-554; Hohsaka, T. et al, Current Opinion in Chemical Biology 2002, 6:809-815, both of which are incorporated herein by their entirety.

NNAAs can offer a variety of advantages, for example, in antibody conjugation, labeling, glycosylytion, photocrosslinking, and so on.

In certain embodiments, the antibodies and the antigen-binding fragments provided herein comprises an NNAA capable of being conjugated. A conjugate molecule with a functional group can be reacted with the corresponding reactive group on an NNAA, such that a stable linkage can be formed between the NNAA of the antibody and the conjugate, thereby attaching the conjugate to the antibody. For example, NNAAs containing keto group or aldehyde or β-diketomoieties can react with a hydrazide- or O-alkylhydroxylamine-, hydroxylamine-containing agents to form a hydrazone or an O-alkylated oxime linkage. For another example, NNAAs containing an azide group can react with an alkyne derivative to form a stable triazole linker by copper (I) catalyzed [3+2] cycloaddition (and vice versa). For another example, NNAAs containing an azide group can be ligated with an appropriate water soluble phosphine-containing agent to form an amide linkage by a Staudinger ligation. Further, a thioester moiety in an NNAA can react with an amine-containing agent to form amide linkage. The antibodies and antigen-binding fragments incorporated with an NNAA can be conjugated with an agent via cycloaddition reactions, such as (4+2) cycloaddtion between diene and dienophile (Diels-Alder reaction), (3+2) cycloaddtion via 1,3-dipolar Huisgen cycloaddition, and (3+2) cycloaddtion via Nitrone-olefin cycloaddition. Cycloaddition methods suitable for antibody conjugation have been described in, for example, WO05003294, US20120004183, WO06009901, WO07130453 and U.S. Pat. No. 6,737,236. Such approaches are particularly useful in conjugating the antibodies with a variety of conjugates such as for example, fluorophores, affinity molecule (e.g. biotin), sugar analogs, polymers (e.g. PEGs), and chemical compounds (e.g. cytotoxins and anti-tumor agents).

In certain embodiments, the antibodies and antigen-binding fragments incorporated with an NNAA comprises an azide group or an alkyne group. Such NNAA can be conjugated via copper catalyzed click chemistry, for example, NNAA with an azide can be reacted with a conjugate with a terminal alkyne in the presence of copper (I) ion, to allow formation of a triazole linkage. NNAA with an alkyne group may also be reacted with an agent with an azide group via the copper catalyzed click chemistry. More details of the reaction have been described in, for example, U.S. Pat. No. 7,009,059, WO2004055160, U.S. Pat. No. 7,375,234, and U.S. Pat. No. 7,763,736.

Any suitable NNAAs known in the art may be used, including, without limitation, those described in PCT publications WO05038002, WO04035743, WO04035605, WO06001832, WO06068802, and WO06110182, and US Pat. Appl. US20130030160, US20130028906, and US20120301490. In certain embodiments, the NNAA is an analog of any of the 20 standard amino acids. Exemplary NNAA include, without limitation:

a lysine analog such as pyrrolysine,
a phenylalanine analog such as p-nitrophenylalanine, p-aminophenylalanine, p-(2-amino-3-hydroxyethyl)phenylalanine, p-benzoylphenylalanine, p-phenylazophenylalanine, p-azidophenylalanine, p-iodophenylalanine, p-acetylphenylalanine, p-methoxyphenylalanine, p-(3-oxobutanoyl)-L-phenylalanine, p-isopropylthiocarbonylphenylalanine, p-ethylthiocarbonylphenylalanine, and p-propargyloxyphenylalanine, p-carboxymethylphenylalanine, 3,4-dihydroxy-L-phenylalanine, an alanine analog such L-3-(2-naphthyl)alanine,
a tyrosine analog such as O-methyl-tyrosine, O-(2-nitrobenzyl)-tyrosine, 0-(trimethylammoniumalkyl) tyrosine, 3-iodotyrosine, 3-amino-tyrosine,
a cysteine analog such as S-(2-nitrobenzyl)-cysteine, selenocysteine,
a phenylalanine analog such as p-benzoyl-L-phenylalanine,
a tryptophan analog such as 5-hydroxytryptophan,
glycine analog such as 7-hydroxycoumarin-glycine and dansyl-glycine,
a serine analog such as β-GlcNAc-serine, N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine;
a threonine analog such as α-GalNAc-threonine, and
a glutamine analog such as L-homoglutamine.

An NNAA can be encoded by a given genetic codon which can be incorporated in a desired site of a nucleotide sequence encoding the antibody or antigen-binding fragment thereof. An NNAA can be encoded by a unique genetic codon which is different from the natural codon encoding for any of the 20 standard amino acids. A genetic codon for an NNAA can be a stop codon (e.g. amber (UAG), ochre (UAA), and opal (UGA) codons), a four-base codon (e.g. AGGA, AGGU, CGGU, CGCU, CGAU, CCCU, CUCU, CUAU, and GGGU), a five-base codon, a six-base codon, and so on.

An NNAA can be incorporated to the antibodies and the antigen-binding fragments thereof by a translation system which comprises an orthogonal tRNA-aminoacyl-tRNA synthetase pair. In general, the antibody-encoding nucleotide sequence comprising the codon for the NNAA can be introduced to a translation system, where the codon for the NNAA can be specifically recognized and translated into the NNAA by the orthogonal pair of tRNA and tRNA aminoacyl synthetase, thereby translating the nucleotide into the antibody and the antigen-binding fragment with the NNAA incorporated.

The synthetase in the orthogonal pair specifically aminoacylates the tRNA with the NNAA, and the tRNA can specifically recognize the genetic codon for the NNAA. The pair may be artificially introduced to the system (i.e. an exogenous pair of tRNA and synthetase), or naturally present in the system (i.e. a native pair of tRNA and synthetase in a microorganism). Methods for preparing such a translation system are well known in the art, see, for example, PCT publications WO02085923, WO02086075, WO03033521, WO04094593, WO05007624, WO05007870, and WO05019415.

Conservative Variants

In certain embodiments, the anti-hER36 antibodies and the antigen-binding fragments therefore comprise a conservative substitution from the SNGmB1 antibody. "Conservative substitution" as used herein refers to substitution of an amino acid residue with another amino acid residue whose side chain has similar physiochemical properties to that of the residue to be substituted (e.g., hydrophobicity and molecular bulk of the side chain). For example, conservative substitutions can be made among amino acids with hydrophobic side chains (e.g. Met, Ala, Val, Leu, and Ile), among amino acids with neutral hydrophilic side chains (e.g. Cys, Ser, Thr, Asn and Gln), among amino acids with acidic side chains (e.g. Asp, Glu), among amino acids with basic side chains (e.g. His, Lys, and Arg), or among amino acids with aromatic side chains (e.g. Trp, Tyr, and Phe). As known in the art, conservative substitution does not cause significant change in the protein conformational structure, and therefore do not reduce or impair the biological activity of a protein. In certain embodiments, conservative substitutions can be introduced to one or more sites of the variable regions of the SNGmB1 antibody, for example, sites that are not critical for antigen-binding.

pH-Dependent Variants

In certain embodiments, the antibodies or antigen-binding fragments comprises one or more amino acid substitution(s) that imparts pH-dependent binding to ER-α36. In certain embodiments, such antibodies and antigen-binding fragments have reduced binding to ER-α36 at acidic pH relative to the binding at neutral pH. Antibodies bound to a surface receptor may be internalized to cytosol and followed by degradation in lysosome where the pH is acidic. It is contemplated that an reduced affinity at an acidic pH can dissociate the antibody from the receptor in lysosome and allow the antibody to escape from being degraded, and be recycled back to the cell surface for continued binding to an additional receptor molecule.

Antibodies and antigen-binding fragments having pH-dependent binding with ER-α36 can be engineered using methods known in the art, see, for example, Igawa T. et al, Nature biotechnology, 28(11): 2010; US Pat. Appl. 20110076275, US Pat. Appl. 20110111406. For example, the surface residues of the antibodies or fragment thereof can be mutated using Histidine scanning, and the resulting mutants can be screened for the binding affinity to the receptor at both acidic pH and neutral pH. Certain residues on the variable regions suitable for Histidine mutation have been disclosed, for example, in US Pat. Appl. 20110076275, and US Pat. Appl. 20110111406.

In certain embodiments, the antibodies or antigen-binding fragments comprises one or more amino acid substitution(s) that improves pH-dependent binding to an Fc receptor (FcRn). Ig G is known to bind to FcRn at acidic pH and dissociate at neutral pH. An internalized IgG can complex with FcRn in endosome, and can be released out of the cell through when the endosome transcytoses to the basolateral side of the cell. Such binding with FcRn allows the IgG to escape from being degraded in the lysosome, and therefore can extend the pharmacokinetic half life of the antibodies. Methods of engineering an antibody and antigen-binding fragment thereof to improve binding affinity with FcRn are well-known in the art, see, for example, Vaughn, D. et al, Structure, 6(1): 63-73, 1998; Kontermann, R. et al, Antibody Engineering, Volume 1, Chapter 27: Engineering of the Fc region for improved PK, published by Springer, 2010; Yeung, Y. et al, Cancer Research, 70: 3269-3277 (2010); and Hinton, P. et al, J. Immunology, 176:346-356 (2006). The mutated antibodies can be screened to identify a candidate with improved FcRn binding affinity.

Variants with Altered ADCC Activity

In certain embodiments, the antibodies or antigen-binding fragments can be engineered in the Fc region to alter the antibody-dependent cellular cytotoxicity (ADCC). Fc region binds to Fc receptors on the surface of effector cells such as natural killer cells and macrophages, and direct such effector cells to the targeted cells such as ER-α36 expressing cells. In certain embodiments, the antibodies or antigen-binding fragments comprises one or more modification or mutation that enhances ADCC activity. Certain amino acid residues at CH2 domain of the Fc region can be substituted to provide for enhanced ADCC activity. Alternatively or additional, carbohydrate structures on the antibody can be changed to enhance ADCC activity. Methods of enhancing ADCC activity by antibody engineering have been described in the art, see for example, Shields R L. et al., J Biol Chem. 2001. 276(9): 6591-604; Idusogie E E. et al., J Immunol. 2000.164 (8):4178-84; Steurer W. et al., J Immunol. 1995, 155(3): 1165-74; Idusogie E E. et al., J Immunol. 2001, 166(4): 2571-5; Lazar G A. et al., PNAS, 2006, 103(11): 4005-4010; Ryan M C. et al., Mol. Cancer Ther., 2007, 6: 3009-3018; Richards J O, et al., Mol Cancer Ther. 2008, 7(8): 2517-27; Shields R. L. et al, J. Biol. Chem, 2002, 277: 26733-26740; Shinkawa T. et al, J. Biol. Chem, 2003, 278: 3466-3473.

Epitope

The present disclosure further provides antibodies and the antigen-binding fragments thereof which substantially bind to the same epitope to which the SNGmB1 antibody specifically binds.

Methods for identifying the epitope of an antibody are well-known in the art, for example, by alanine scanning. Generally, single alanine mutation is introduced to an interested residue to produce a mutated antigen, and binding affinities of the mutated antigen and the antibody are tested, for example using competitive ELISA or Radioligand immuno-binding assay. Residues constituting the epitope will be distinguished if the antibody binding activity is significantly reduced or impaired by such alanine replacement, as described by Cunningham et al., Science 244 (4908): 1081-1085 (1989). More methods can be found at, for example, Westwood, O. et al, Epitope Mapping: a practical approach, published by Oxford University Press, 2001.

In certain embodiments, the antibody of the present application can bind to an epitope comprising one ore more residues selected from the group consisting of S3, K8, R10, P16, K17, G20, N21, K22, W23 of SEQ ID NO: 2. In certain embodiments, the epitope comprises one or more residues selected from the group consisting of G20, N21, K22, W23, and/or F24 of SEQ ID NO: 2.

In certain embodiments, the epitope comprises residues of G20, N21, K22, W23, and/or F24 of SEQ ID NO: 2. In certain embodiments, the epitope comprises residues of S3, K8, R10, P16, K17, G20, N21, K22, W23 of SEQ ID NO: 2.

In certain embodiments, the epitope consists of residues of G20, N21, K22, W23, and/or F24 of SEQ ID NO: 2. In certain embodiments, the epitope consists of residues of S3, K8, R10, P16, K17, G20, N21, K22, W23 of SEQ ID NO: 2.

Antibodies binding to the same epitope tend to compete for binding with each other, or blocking the binding of the other to the antigen. Therefore, competitive binding assay may also be used to identify antibodies that bind to the same epitope to which the SNGmB1 antibody specifically binds.

Method of Using the Antibodies and Antigen-Binding Fragments

The antibodies and antigen-binding fragments provided herein have been found to inhibit tumor growth in vivo. Therefore, the antibodies and antigen-binding fragments may be used to treat various conditions or diseases associated with ER-α36.

In certain embodiments, methods of preventing and/or treating a disease associated ER-α36 in a subject comprising administering to the subject a therapeutic effective dosage of a pharmaceutical composition comprising the antibodies or antigen-binding fragments provided herein. Examples of diseases associated with ER-α36 include without limitation bone loss, bone fractures, osteoporosis, metastatic bone disease, Paget's disease, periodontal disease, cartilage degeneration, endometriosis, uterine fibroid disease, hot flashes, increased levels of LDL cholesterol, cardiovascular disease, impairment of cognitive functioning, cerebral degenerative disorders, restenosis, gynecomastia, vascular smooth muscle cell proliferation, obesity, incontinence, anxiety, depression resulting from an estrogen deficiency, perimenopausal depression, post-partum depression, premenstrual syndrome, manic depression, anxiety, dementia, obsessive compulsive behavior, attention deficit disorder, sleep disorders, irritability, impulsivity, immune deficiency, auto immune diseases, anger management, multiple sclerosis and Parkinson's disease, inflammation, inflammatory condition, inflammatory bowel disease, respiratory diseases, sexual dysfunction, hypertension, retinal degeneration, asthma and cancers. Preferably, diseases related to ER-α36 include bone loss, bone fracture, osteoporosis, menopause, premenstrual syndrome, endometriosis, uterine disease, impotence, sexual dysfunctions, increased levels of LDL cholesterol, cardiovascular diseases, vascular smooth muscle cell proliferation, depression resulting from an estrogen deficiency, perimenopausal depression, post-partum depression, immune deficiency, auto immune diseases, inflammation, inflammatory condition, asthma and cancerous conditions. More preferably, diseases associated with ER-α36 include bone loss, osteoporosis, impotence, cardiovascular diseases, atherosclerosis, immune deficiency, inflammation, inflammatory condition, asthma and cancerous condition. The inflammatory condition used herein includes rheumatoid arthritis, psoriasis, scleroderma, chronic obstructive pulmonary disease, and asthma. The subject may be a mammal such as a dog, cat, cow, sheep, horse, or human, preferably a human. The required therapeutic amount for the method will vary according to the specific diseases and is readily ascertainable by one of ordinary skill in the art having benefit of the instant disclosure.

In certain embodiments, methods of preventing and/or treating a cancerous condition in a subject comprising administering to the subject a pharmaceutical composition comprising the antibodies or antigen-binding fragments provided herein. Cancerous conditions and tumor types that may be treated using the antibodies or antigen-binding fragments disclosed herein include but are not limited to carcinoma, blastoma, sarcoma, germ cell tumor, or hematological or lymphoid malignancy such as leukemia, lymphoma, or multiple myeloma. More specifically, cancerous conditions and tumor types that may be treated using the antibodies disclosed herein include but are not limited to squamous cell cancer, lung cancer (e.g., small cell lung cancer, non-small cell lung cancer (NSCLC), adenocarcinoma of the lung, or squamous cell carcinoma of the lung), cancer of the peritoneum, liver cancer (e.g., hepatocellular carcinoma/hepatoma), gastric or stomach cancer (e.g., gastrointestinal cancer), pancreatic cancer, brain tumor (e.g., glioblastoma/glioblastoma multiforme (GBM), non-glioblastoma brain tumor, or meningioma), glioma (e.g., ependymoma, astrocytoma, anaplastic astrocytoma, oligodendroglioma, or mixed glioma such as oligoastrocytoma), cervical cancer, ovarian cancer, liver cancer (e.g., hepatoblastoma, hepatocellular carcinoma/hepatoma, or hepatic carcinoma), bladder cancer (e.g., urothelial cancer), breast cancer, colon cancer, colorectal cancer, rectal cancer, endometrial or uterine carcinoma, salivary gland carcinoma, kidney or renal cancer (e.g., rhabdoid tumor of the kidney), prostate cancer, vulval cancer, penile cancer, anal cancer (e.g., anal squamous cell carcinoma), thyroid cancer, head and neck cancer (e.g., nasopharyngeal cancer), skin cancer (e.g., melanoma or squamous cell carcinoma), osteosarcoma, Ewing's sarcoma, chondrosarcoma, soft tissue sarcoma (e.g., rhabdomyosarcoma, fibrosarcoma, Kaposi's sarcoma), carcinoid cancer, eye cancer (e.g., retinoblastoma), mesothelioma, lymphocytic/lymphoblastic leukemia (e.g., acute lymphocytic/lymphoblastic leukemia (ALL) of both T-cell lineage and B-cell precursor lineage, chronic lymphoblastic/lymphocytic leukemia (CLL), acute myelogenous/myeloblastic leukemia (AML), including mast cell leukemia, chronic myelogenous/myelocytic/myeloblastic leukemia (CML), hairy cell leukemia (HCL), Hodgkin's disease, non-Hodgkin's lymphoma, chronic myelomonocytic leukemia (CMML), follicular lymphoma (FL), diffuse large B cell lymphoma (DLCL), mantle cell lymphoma (MCL), Burkitt's lymphoma (BL), mycosis fungoides, Sezary syndrome, cutaneous T-cell lymphoma, mast cell neoplasm, medulloblastoma, nephroblastoma, solitary plasmacytoma, myelodysplastic syndrome, chronic and non-chronic myeloproliferative disorder, central nervous system tumor, pituitary adenoma, vestibular schwannoma, primitive neuroectodermal tumor, ependymoma, choroid plexus papilloma, polycythemia vera, thrombocythemia, idiopathic myelfibrosis, and pediatric cancers such as pediatric sarcomas (e.g., neuroblastoma, rhabdomyosarcoma, and osteosarcoma). In addition, tumors can be malignant (e.g., cancers) or benign (e.g., hyperplasia, cyst, pseudocyst, hamartoma, and benign neoplasm).

In certain embodiments, methods of inhibiting tumor matasis associated with ER-α36 in a subject comprising administering to the subject a therapeutic effective dosage of a pharmaceutical composition comprising the antibodies or antigen-binding fragments provided herein.

In certain embodiments, the antibodies and antigen-binding fragment disclosed herein are modulators of ER-α36 and are useful for modulating the ER-α36 activities in cells in vitro and in vivo. In certain embodiments, the antibodies and antigen-binding fragment disclosed herein may induce cell death and/or inhibit cell proliferation.

In certain embodiments, methods of modulating the ER-α36 activities in a cell comprise exposing a cell expressing ER-α36 to the antibodies and antigen-binding fragment disclosed herein. The cells may express ER-α36 endogenously or exogenously through genetic engineering. In one embodiment, the cells express ER-α36 endogenously. In a preferred embodiment, the cells are cancer cells that express ER-α36 endogenously. Examples of cancer cells that express ER-α36 are breast cancer cells, leukemia cells, lung cancer cells, myeloma cells, prostate cancer cells, ovarian cancer cells, colon cancer cells and stomach cancer cells. In a further preferred embodiment, the cells expressing ER-α36 are breast cancer cells that express ER-α36 endogenously. Examples of breast cancer cells expressing ER-α36 are MCF7 and MDA-MB-231 cells. The expression of the endogenous ER-α36, may be increased or decreased through treatment with one or more agents. Examples of such agents are serum, E2β (17β-estradiol), Tamoxifen and ICI 182,780.

In another embodiment, the cells are altered by genetic engineering to express exogenous ER-α36. Cells expressing exogenous ER-α36 may be prepared by genetic engineering methods known to one of ordinary skill in the art (See Sambrook et al., Molecular Cloning, A Laboratory Manual (2d Ed. 1989) (Cold Spring Harbor Laboratory)). Briefly, an exogenous ER-α36 gene is prepared and inserted into an expression vector, which is transfected into a host cell, which is then grown in a culture solution suitable for expressing the exogenous ER-α36. An example of the gene sequence of human ER-α36 is disclosed in Wang et al., *Biochem. Biophys. Res. Commun.* 336, 1023-1027 (2005) (GenBank Accession No. BX640939). The cells expressing exogenous ER-α36 may or may not express endogenous ER-α36. The expression levels of endogenous or exogenous ER-α36 in the cells may be increased or decreased by treatment with one or more other agents. Examples of such agents are serum, E2β (17β-estradiol), Tamoxifen and ICI 182,780. The cells expressing ER-α36 may or may not express other estrogen receptors such as ER-α66, ER-α46 and ER-β.

The antibodies or antigen-binding fragments disclosed herein may be administered alone or in combination with one or more additional therapeutic means or agents. For example, the antibodies or antigen-binding fragments disclosed herein may be administered in combination with chemotherapy, radiation therapy, surgery for the treatment of cancer (e.g., tumorectomy), one or more anti-emetics or other treatments for complications arising from chemotherapy, or any other therapeutic agent for use in the treatment of cancer or any medical disorder mediated by ER-α36. In certain of these embodiments, an antibody or antigen-binding fragment as disclosed herein that is administered in combination with one or more additional therapeutic agents may be administered simultaneously with the one or more additional therapeutic agents, and in certain of these embodiments the antibody or antigen-binding fragment and the additional therapeutic agent(s) may administered as part of the same pharmaceutical composition. However, an antibody or antigen-binding fragment administered "in combination" with another therapeutic agent does not have to be administered simultaneously with or in the same composition as the agent. An antibody or antigen-binding fragment administered prior to or after another agent is considered to be administered "in combination" with that agent as the phrase is used herein, even if the antibody or antigen-binding fragment and second agent are administered via different routes. Where possible, additional therapeutic agents administered in combination with the antibodies or antigen-binding fragments disclosed herein are administered according to the schedule listed in the product information sheet of the additional therapeutic agent, or according to the Physicians' Desk Reference 2003 (*Physicians' Desk Reference,* 57th Ed; Medical Economics Company; ISBN: 1563634457; 57th edition (November 2002)) or protocols well known in the art. Examples of therapeutic agents include, but are not limited to, Icaritin, Tamoxifen, 17β-estradol, ICI 182,780, compounds disclosed in the U.S. patent application Ser. No. 11/877,575 filed on Oct. 23, 2007 which is incorporated herein by reference, compounds disclosed in the U.S. Pat. Appl. 60/046,255 filed on Apr. 8, 2008 which is incorporated herein by reference, cytokines, anti-VEGF antibodies (e.g., Bevacizumab or Avastin), anti-HER2 antibodies (e.g., Herceptin or trastuzumab), anti EGFR antibodies (Nimotuzamab or Erbitux), and tyrosin receptor inhibitors such as Gapatinib and Lapatinib.

Example of cytokines include but are not limited to lymphokines, monokines, human growth hormone, bovine growth hormone, parathyroid hormone, thyroxine, insulin, proinsulin, relaxin, prorelaxin, follicle stimulating hormone, thyroid stimulating hormone, luteinizing hormone, hepatic growth factor, fibroblast growth factor, prolactin, placental lactogen, tumor necrosis factor, mullerian-inhibiting substance, mouse gonadotropin-associated peptide, inhibin, activin, integrin, thrombopoietin, nerve growth factors such as NGF-β, platelet growth factor, transforming growth factors such as TGF-α and TGF-β, insulin-like growth factor I and II, erythropoietin, osteoinductive factors, interferons such as interferon-α, -β, and -γ, colony stimulating factors such as macrophage-CSF, granulocyte macrophage CSF, and granulocyte-CSF, interleukins such IL-1, IL-1α, IL-2, IL-3, IL-4, IL-5, IL-6, IL-7, IL-8, IL-9, IL-10, IL-11, and IL-12, tumor necrosis factors such as TNF-α and TNF-β, and other polypeptide factors.

In certain embodiments, antibodies or antigen-binding fragments disclosed herein are used by being linked to, conjugated with or in combination with one or more chemotherapeutic agents. Examples of chemotherapeutic agents include, but are not limited to, amrubicin, atrasentan batabulin, calcitriol, cilengitide, dasatinib, decatanib, edotecarin, enzastaurin, erlotinib, everolimus, gimatecan, gossypol ipilimumab, lonafarnib, lucanthone, neuradiab, nolatrexed, oblimersen, ofatumumab, oregovomab, panitumumab, pazopanibrubitecan, talampanel, temsirolimus, tesmilifene, tetrandrine, ticilimumab, trabectedin, vandetanib, vitespan, zanolimumab, zolendronate, histrelin, azacitidine, dexrazoxane, alemtuzumab, lenalidomide, gemtuzumab, ketoconazole, nitrogen mustard, ibritumomab tiuxetan, decitabine, hexamethylmelamine, bexarotene, tositumomab, arsenic trioxide, editronate, cyclosporine, Edwina-asparaginase, and strontium 89.

It is contemplated that a variety of conjugates may be linked to the antibodies or antigen-binding fragments provided herein (see, for example, "Conjugate Vaccines", Contributions to Microbiology and Immunology, J. M. Cruse and R. E. Lewis, Jr. (eds.), Carger Press, New York, (1989)). These conjugates may be linked to the antibodies or antigen-binding fragments by covalent binding, affinity binding, intercalation, coordinate binding, complexation, association, blending, or addition, among other methods. If needed, specific sites can be engineered outside the epitope binding portion so as to provide sites for the conjugation. For example, the antibodies or antigen-binding fragments thereof may be engineered to include one or more reactive amino acid residues, such as for example cysteine, histidine, lysine, glutamine or methionine residues, or NNAAs as described above, to facilitate covalent linkage to a conjugate.

In certain embodiments, the antibodies may be linked to a conjugate indirectly, or through another conjugate or through a linker. For example, the antibody or antigen-binding fragments may be conjugated to biotin, then indirectly conjugated to a second conjugate that is conjugated to avidin. Various linkers can be used to link a conjugate to a residue on the antibody, for example, (6-maleimidocaproyl) hydrazone linker for linking to a cysteine, 4-(4'-acetylphenoxy)butanoic acid for linking to a lysine, 4-mercaptopentanoate for linking to lysine, and valine-citrulline linker for linking to a cysteine (see, e.g., Ducry, L. et al, Bioconjugate Chem., Vol. 21, No. 1, 2010). To prepare a cysteine-linker antibody conjugate, the antibody or its fragment may be partially reduced by a reducing agent such as dithiothreitol (DTT), tris(2-carboxyethyl)phosphine (TCEP), or aminoethanethiol to provide free thiol groups, which are subsequently alkylated with the conjugate linked linker such as valine-citrulline linked monomethyl auristatin E (MMAE). However, in alternative embodiments, the antibody or antigen-binding fragment can be used without reduction to obtain cysteine-linker antibody conjugate, e.g. by insertion of free cysteine in the antibody or antigen-binding fragment sequence, or by insertion of free S-methylated cysteine followed by demethylation of the inserted S-methylated cysteine. Similarly, demethylation of methionine provides the thiol or sulfhydryl group (—SH) that can be further conjugated with another molecule such as a linker or a small molecule (e.g. a drug). The antibody conjugates as prepared can be further purified and tested.

In certain embodiments, conjugates and linkers linked to the antibodies or antigen-binding fragments disclosed herein may comprise one or more agents or functional groups meant to alter one or more pharmacokinetic (PK) properties (for example, to increase the half-life) or to decrease the immunogenicity of the antibody or antigen-binding fragment. Such agents or functional groups can include, without limitation, polyethylene glycol (PEG), glucuronic acid or other sugar based linkers, polar, positively or negatively charged groups that can increase the rates of hydrolysis of a succinimidyl ring and reduce or minimize the rate of reverse Michael reaction, therefore reduce or minimize the rate of loss of drug and the linker group from the antibody or antibody fragments to other thiol-containing proteins and small molecules.

In certain embodiment, the present disclosure provides antibody-drug conjugates. The antibody-drug conjugates comprise the antibody or antigen-binding fragment of the present invention covalently attached to one or more drug moieties. In certain embodiments, the antibody-drug conjugates have a formula of Ab(-L-D)$_n$, wherein the Ab is the antibody or antigen-binding fragment of the present disclosure, D is a drug, L is a linker coupling the drug to the antibody or antigen-binding frament, and the linker can be either cleavable or noncleavable in the presence of the target cells or tissues, n is an integer ranging from 1-60.

Any types of linkers can be used. Examples of suitable linkers include but are not limited to maleimidocaproyl (MC), maleimidocaproyl-valine-citrulline-p-aminobenzyl-carbamoyl (mc-vc-PAB), SMCC, SPDB and MB-vc. In certain embodiments, the linker (i.e. L) is selected from the group consisting of maleimidocaproyl (see, e.g. Formula (II)), maleimidocaproyl-valine-citrulline-p-aminobenzylcarbamoyl (see, e.g. Formula (III)), N-succinimidyl-4-(maleimidomethyl)cyclohexanecarboxylate (see, e.g. Formula (V)), N-succinimidyl-4-(2-pyridyldithio)butanoate (see, e.g. Formula (VI)) and MB-vc (see, e.g. Formula (IV)). The structures of exemplary linkers are shown below:

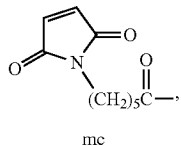

mc

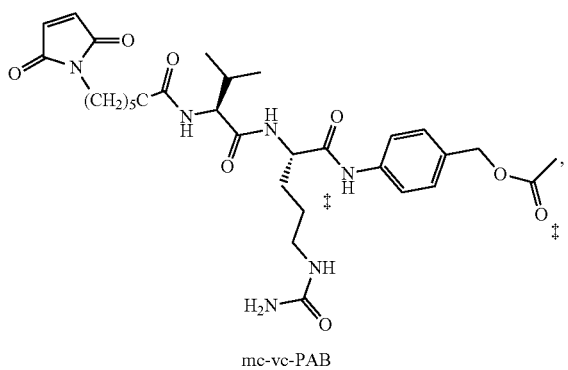

mc-vc-PAB

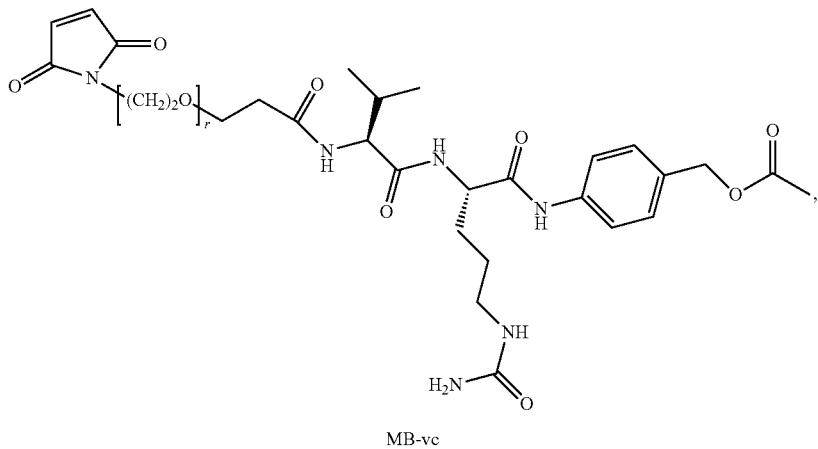

MB-vc

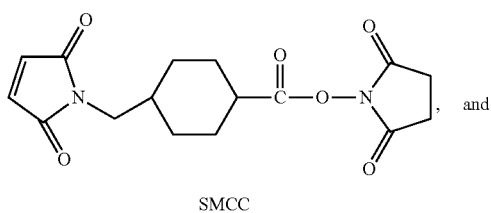

SMCC

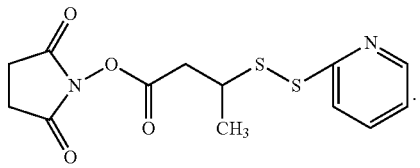

SPDB

The term "drug" as used herein refers to a therapeutic agent, or preferably a cytotoxic agent. Examples of the drug include but are not limited to monomethyl auristatin E (MMAE), monomethyl auristatin F (MMAF), duocarmycin and maytansinoid such as $N^{2'}$-deacetyl-$N^{2'}$-(3-mercapto-1-oxopropyl)-maytansine (DM1) and $N^{2'}$-deacetyl-$N^{2'}$-(4-mercapto-4-methyl-1-oxopentyl)maytansine (DM4).

Also provided herein are the structures of the preferred antibody-drug conjugates such as Ab-mc-vc-PAB-MMAE as shown in formula(VII), wherein "s" is an integer ranging from 1 to 20; Ab-mc-MMAF as shown in formula (VIII), wherein "t" is an integer ranging from 1-20; Ab-SMCC-DM1 as shown in formula (IX), wherein "v" is an integer ranging form 1-60; Ab-SPDB-DM4 as shown in formula (X), wherein "u" is an integer ranging from 1-60; Ab-MB-vc-duocarmycin as shown in formula(I), wherein "y" is an integer ranging from 1-20.

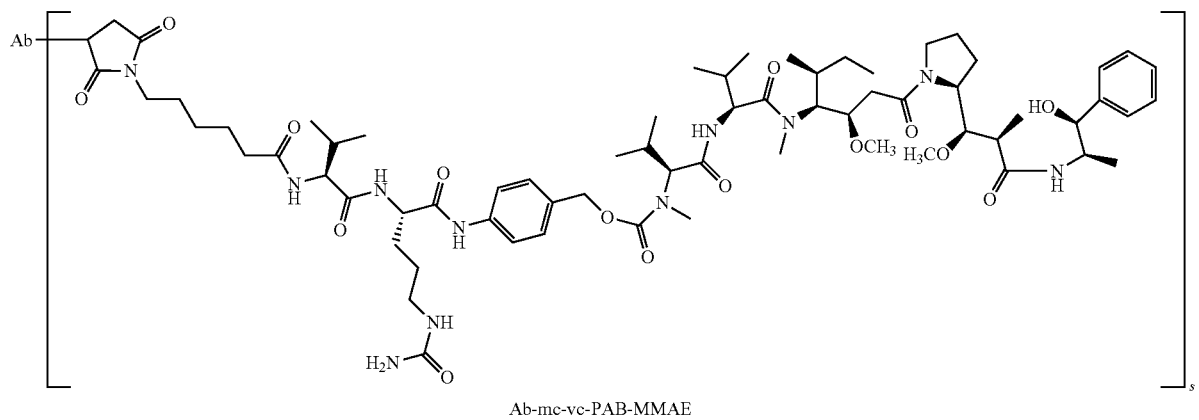
Ab-mc-vc-PAB-MMAE
(VII)
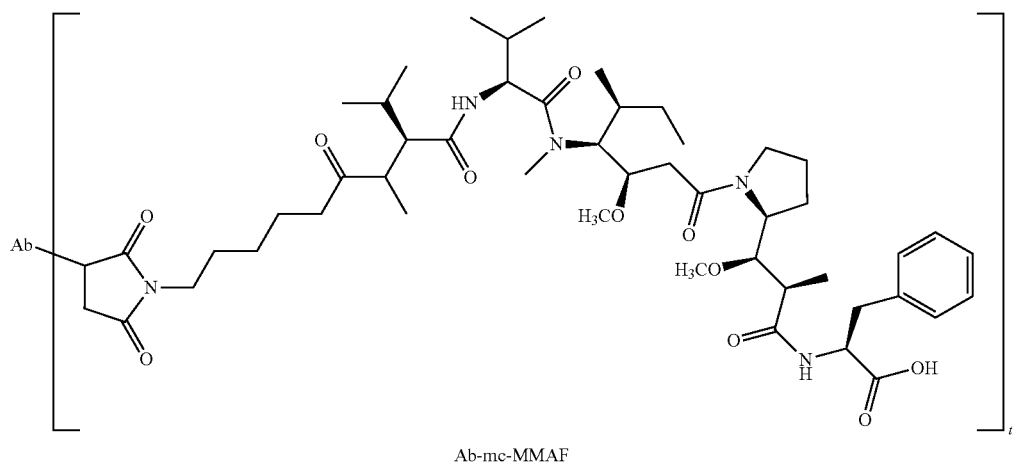
Ab-mc-MMAF
(VIII)
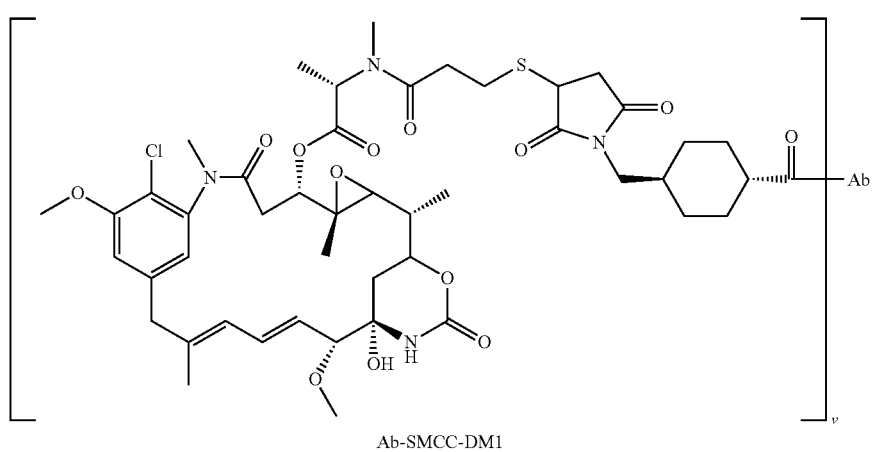
Ab-SMCC-DM1
(IX)

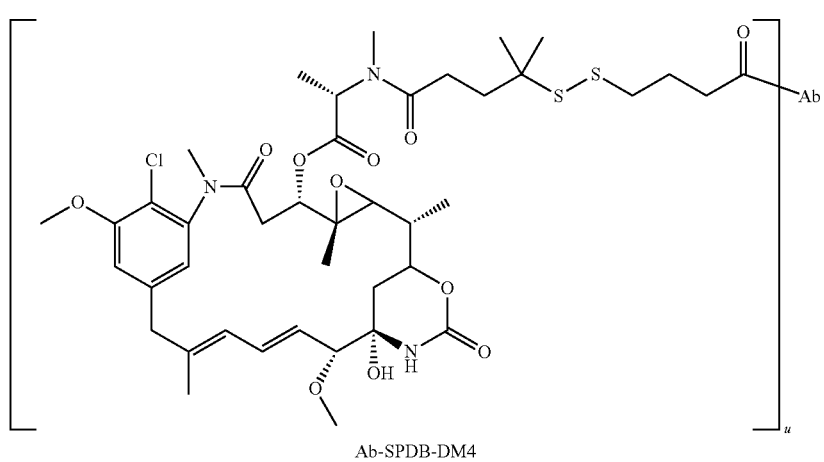

Ab-SPDB-DM4

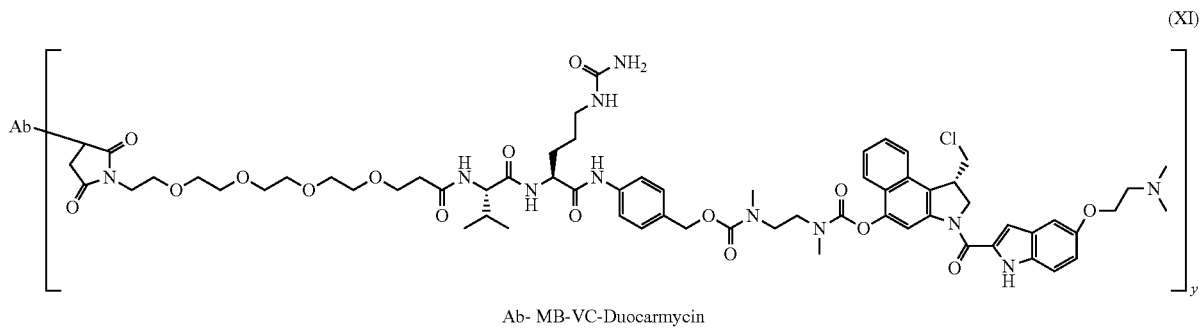

Ab-MB-VC-Duocarmycin wherein, the "s" is an integer ranges from 1-20, "t" is an integer ranges from 1-20, "u" is an integer ranges from 1-60, "v" is an integer ranges from 1-60, "y" is an integer ranges from 1-20, and "Ab" is the antibody or antigen-binding fragement of the present invention.

In the antibody-drug conjugates, in particular those having the formula of Ab(-L-D)$_n$, the linker can react at one end with an reactive group on the antibody or the antigen-binding fragment, and can also react at the other end with another reaction group on the drug moiety, thereby linking the antibody and the drug to form the antibody-drug conjugates.

In certain embodiments, the linker is capable of reacting with the thiol group on a cysteine in the antibody or the antigen-binding fragment thereof. Any suitable cysteine residues in the antibody or antigen-binding fragment can be utilized for the linker reaction. In certain embodiments, the antibody or antigen-binding frament has a limited number of cysteine thiol groups (e.g., 1, 2, 3, 4, 5, 6, 7, 8, 9, 10, etc.) available for reaction with the linker. For example, some existing disulfide bonds in the antibody or antigen-binding fragment can be reduced using a reducing agent such as dithiothreitol (DTT) to release one or more thiol groups for linker reaction. Linkers suitable for reacting with thiol groups in the antibody can include, without limitation, mc-vc-PAB, mc, and MB-vc. Examples of antibody-drug conjugates in which the linkers reacts with cysteine thiol groups are, Ab-mc-vc-PAB-MMAE, Ab-mc-MMAF and Ab-MB-vc-Duocarmycin.

In certain embodiments, the linker is capable of reacting with the amino group on a lysine residue in the antibody or the antigen-binding fragment thereof. In one embodiment, the linker attaches the antibody or antigen-binding fragment to the drug such as maytansinoids through a covalent amide bond formed between a lysine residue on the antibody and an activated ester that also contains a thioether moiety or disulfide bond. The preferred maytansinoids are DM1 and DM4. The structures of the DM1 and DM4 are respectively illustrated as formula (XI) and formula (XII):

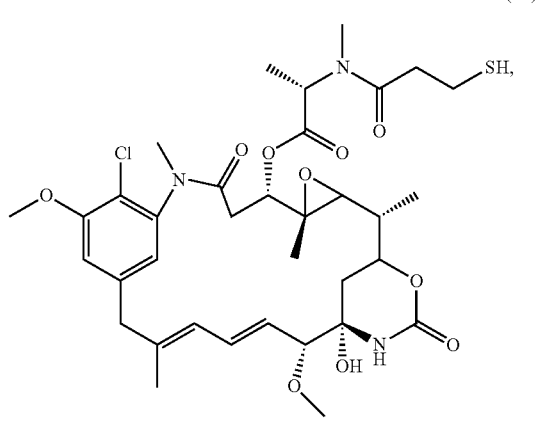

(XI)

-continued

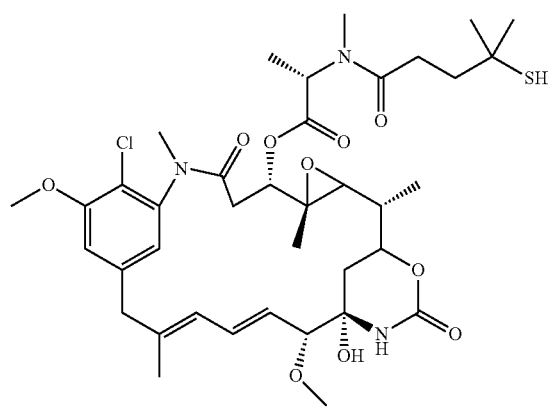

(XII)

In certain embodiments, a molecule of antibody or antigen-binding fragment thereof can be conjugated with more than one molecule of drug moieties. For example, the antibody or antigen-binding fragment can comprise more than one reactive group for linker reaction, thereby resulting in conjugation of more than one linker or drug moieties. In such case, the antibody-drug conjugate can be a mixture of conjugates with a varied number of conjugated linker or drug moieties in a certain distribution. The average number of drug moieties per antibody may be calculated as a weighed average, $\Sigma i*(Ab-(LD)_i\%)$, wherein i is the number of drug moieties on one antibody or antigen-binding fragment, shown here as Ab-(LD)$_i$ and can range from 0 to 60. The percentage of each of a certain species, Ab-(LD)$_i$, is shown as (Ab-(LD)$_i$)%. The loading (drug/antibody ratio, or DAR) of an ADC mixture may be controlled in different manners, including one or all of the following: (i) limiting the molar excess of drug-linker intermediate or linker agent relative to antibody, (ii) limiting the conjugation reaction time or temperature, (iii) partial or limited reductive conditions for cysteine thiol modification, and controlling the number of free cysteine, methionine or NNAAs introduced into the heavy and/or light chains of the antibody or antigen-binding fragment.

In a preferred embodiment, the linker comprises a polyethylene glycol moiety, for example, Ab-MB-vc-Duocarmycin. The PEG portion of the linker may be between 1 and 50 units long. In a preferred embodiment, the PEG moiety has 1-12 repeat units, more preferably 2-6 repeat units. The PEG moiety reduces the degree of aggregation that may occur during the conjugation of the drug to the antibody.

In another preferred embodiment, the linker comprises a peptide sequence. Examples of antibody drug conjugates having a peptide linker includes, without limitation, mc-vc-PAB-MMAE, and MB-vc-duocarmycin. In certain embodiments, the amino acid sequence of the peptide sequences can be chosen based on their suitability for selective enzymatic cleavage, for example by tumor associated proteases. In a preferred embodiment, the peptide linker comprises a two amino-acid linker val-cit. However, it is also known that other amino acid combinations, with two or more than two amino acid residues, can work in a similar way.

In one embodiment, linkers of conjugates comprise non-cleavable linker and cleavable linker. A non-cleavable linker is any chemical moiety that is capable of linking a drug to the antibody or antigen-binding fragment in a stable, covalent manner. The drug attached to it is released by the breakdown of the antibody sequence and the amino acid (such as lysine or cysteine) that is attached to the linker is freed. Non-cleavable linkers are substantially resistant to acid-induced cleavage, light-induced cleavage, peptidase-induced cleavage, esterase-induced cleavage, and disufide bond cleavage. Examples of non-cleavable linkers include linkers involves amide bonds and thioethers, such as SMCC and mc. Cleavable linkers can be cleaved by proteases, peptidases, esterases, light, acid, or disulfide bond breakage, such as the maleimidocaproyl-valine-citrulline-p-aminobenzyloxycarbonyl and MB-vc. It is possible to release a drug from a cleavable linker from the antibody with the antibody being intact.

In certain embodiments, conjugates linked to the antibodies or antigen-binding fragments disclosed herein may comprise one or more detectable labels. Such labels include, but are not limited to, radioactive isotopes such as $^{123}I$, $^{124}I$, $^{125}I$, $^{131}I$, $^{35}S$, $^{3}H$, $^{111}In$, $^{112}In$, $^{14}C$, $^{64}Cu$, $^{67}Cu$, $^{86}Y$, $^{88}Y$, $^{90}Y$, $^{177}Lu$, $^{211}At$, $^{186}Re$, $^{188}Re$, $^{153}Sm$, $^{212}Bi$, and $^{32}P$, other lanthanides, luminescent labels, fluorescent labels such as for example fluorescein, rhodamine, dansyl, phycoerythrin, or Texas Red, and enzyme-substrate labels such as for example horseradish peroxidase, alkaline phosphatase, or δ-D-galactosidase.

In certain embodiments, conjugates linked to the antibodies or antigen-binding fragments disclosed herein may comprise one or more toxins. The toxin can be same or different. Different toxins mean that different molecules with same or different mechanism of actions (MOA) are loaded onto the same mab or mab fragment. Such toxins can be targeted to cells expressing ER-36 and thereby exerting cytotoxicity on the targeted cell. Suitable toxins include, without limitation, auristatins such MMAE and MMAF (Seattle Genetics) through a linker such as vc or mc, maytansines such as DM1, DM3 and DM4 (Immunogen), calicheamicin (Pfizer), duocarmycins (Synthon), PBD dimers (Spirogen, Seattle Genetics and Roche, referring to U.S. Pat. No. 8,426,402), and amatoxins (eg. Amanitin) as RNA polymerase inhibitors (Heidelberg Pharma).

Also provided herein are methods of uses for the antibodies and antigen-binding fragments thereof linked to a conjugate. In certain embodiments, the conjugated antibodies and antigen-binding fragments can be administered to a subject in a therapeutically effective amount, thereby treating, preventing, or alleviating ER-α36 associated diseases, inhibiting the proliferation of ER-α36 expressing cells, reducing ER-α36-expressing cells, and/or killing ER-α36-expressing cells. The antibodies and antigen-binding fragments target specifically to the ER-α36 expressing cells, thereby directing the conjugate (e.g. toxins, chemotherapeutic agents) specifically to the ER-α36 expressing cells where the conjugate can exert the therapeutic effects. By such targeted delivery of the conjugate agents, the efficacy of the conjugates can be significantly improved, and the toxicity caused by non-specific activity can be greatly reduced. In certain embodiments, when administered as an conjugated antibody or an antigen-binding fragment, the therapeutically effective molar amount for the conjugate can be lower (e.g. at least 10%, 20%, 30%, 40%, 50% or higher) than what would be required if not conjugated to the antibody or antigen-binding fragment provided herein.

In certain embodiments, the antibodies or antigen-binding fragments provided herein may be administered as part of a pharmaceutical composition that comprises one or more pharmaceutical acceptable carriers. Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a composition comprising an antibody or antigen-binding fragment and conjugates as provided herein decreases oxidation of the antibody or antigen-binding fragment. This reduction in oxidation prevents or reduces loss of binding affinity, thereby improving antibody stability and maximizing shelf-life. Therefore, in certain embodiments compositions are provided that comprise one or more antibodies or antigen-binding fragments as disclosed herein and one or more antioxidants such as methionine. Further provided are methods for preventing oxidation of, extending the shelf-life of, and/or improving the efficacy of an antibody or antigen-binding fragment as provided herein by mixing the antibody or antigen-binding fragment with one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The therapeutic effective dosage of an antibody or antigen-binding fragment as provided herein will depend on various factors known in the art, such as for example body weight, age, past medical history, present medications, state of health of the subject and potential for cross-reaction, allergies, sensitivities and adverse side-effects, as well as the administration route and extent of tumor development. Dosages may be proportionally reduced or increased by one of ordinary skill in the art (e.g., physician or veterinarian) as indicated by these and other circumstances or requirements.

In certain embodiments, an antibody or antigen-binding fragment as provided herein may be administered at a therapeutically effective dosage of about 0.01 mg/kg to about 100 mg/kg (e.g., about 0.01 mg/kg, about 0.5 mg/kg, about 1 mg/kg, about 2 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg). In certain of these embodiments, the antibody or antigen-binding fragment is administered at a dosage of about 50 mg/kg or less, and in certain of these embodiments the dosage is 10 mg/kg or less, 5 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

The antibodies and antigen-binding fragments disclosed herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes. In embodiments wherein the antibodies or antigen-binding fragments are administered via injection, injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving an antibody or antigen-binding fragment as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the anti-hER antibody or antigen-binding fragment thereof or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

The antibodies and antigen-binding fragments provided herein may be used in various non-therapeutic uses. In certain embodiments, the antibodies or antigen-binding fragments may be used as affinity purification agents to purify ER-α36 or fragments thereof. In these embodiments, the antibodies or antigen-binding fragments may be immobilized on a solid phase such as a resin or filter paper using methods known in the art. The antibodies or antigen-binding fragments may also be used to precipitate ER-α36 or fragments thereof from solution. In other non-therapeutic embodiments, the antibodies or antigen-binding fragments may be used in various in vitro or in vivo diagnostic or detection applications. In certain of these embodiments, the antibodies or antigen-binding fragments may be conjugated to a detectable label. In other embodiments, the antibodies or antigen-binding fragments may not be conjugated to a detectable label, but may be detected using a labeled secondary antibody that binds to the antibody. In certain embodiments, the antibodies or antigen-binding fragments disclosed herein may be used to detect ER-α36 expression. In certain of these embodiments, the antibodies or antigen-binding fragments may be used to diagnose a condition associated with increased or decreased ER-α36 expression. For example, the antibody or antigen-binding fragment may be contacted with a biological sample from a subject in order to diagnose a condition associated with increased or decreased ER-α36 expression in the subject, in particular, the progression or recession of a condition associated with ER-α36. Likewise, the antibody or antigen-binding fragment may be administered to the subject directly, with binding to ER-α36 detected using methods known in the art.

In certain embodiments, isolated nucleic acid encoding the antibodies or antigen-binding fragment herein, vectors and host cells comprising the nucleic acid, and recombinant techniques for the production of the antibody are provided.

For recombinant production of the antibody, the nucleic acid encoding it may be isolated and inserted into a replicable vector for further cloning (amplification of the DNA) or for expression. In another embodiment, the antibody may be produced by homologous recombination known in the art. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescens*, and *Shigella*, as well as Bacilli such as *B. subtilis* and *B. licheniformis*, *Pseudomonas* such as *P. aeruginosa*, and *Streptomyces*.

In addition to prokaryotes, eukaryotic microbes such as filamentous fungi or yeast are suitable cloning or expression hosts for anti-ER antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated antibodies or antigen-fragment provided here are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for anti-ER antibody production and cultured in conventional nutrient media modified as appropriate for inducing promoters, selecting transformants, or amplifying the genes encoding the desired sequences.

The host cells used to produce the antibodies or antigen-binding fragments provided herein may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human .gamma.1, .gamma.2, or .gamma.4 heavy chains (Lindmark et al., J. Immunol. Meth. 62:1-13 (1983)). Protein G is recommended for all mouse isotypes and for human .gamma.3 (Guss et al., EMBO J. 5:1567 1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a C.sub.H3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

In certain embodiments, the antibodies or antigen-binding fragments provided herein can be provided in a kit, i.e., a packaged combination of agents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various agents may be varied widely to provide for concentrations in solution of the agents which substantially optimize the sensitivity of the assay. Particularly, the agents may be provided as dry powders, usually lyophilized, including excipients which on dissolution will provide an agent solution having the appropriate concentration.

In certain embodiments, an article of manufacture containing materials useful for the treatment of the conditions described above is provided. The article of manufacture comprises a container and a label. Suitable containers include, for example, bottles, vials, syringes, and test tubes. The containers may be formed from a variety of materials such as glass or plastic. The container holds a phamaceutical composition provided herein (comprising the antibodies or antigen-binding fragment disclosed herein) which is effective for treating the condition and may have a sterile access port (for example the container may be an intravenous solution bag or a vial having a stopper pierceable by a hypodermic injection needle). The label on or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1 Recombinant Protein Production and Establishment of ER-α36 Expressing Cells Recombinant ER-α36 proteins are produced for immunization and by following method.

Fusion Protein of Ligand Binding Domain of Ligand Binding Domain of ER-α36 and Fc (LBD-ER-α36_Fc)

Fc was fused to the C terminal of the ER-α36 ligand binding domain by a recombinant method. A vector expressing LBD-ER-α36_Fc was constructed. The ligand binding domain of ER-α36 spans from the 166th amino acid to the 310th amino acid of SEQ ID NO: 1. The plasmid pET30a-ER-α36 LBD-Fc was constructed using the following method. Human ER-α36 full length gene was cloned into BamH I/Not I sites of pcDNA3.1(+) vector (Invitrogen) and inserted sequence was confirmed by DNA sequence validation using T7 Forward and BGH reverse primers. Human ER-α36 with N-terminal myc tag and kozak sequence was also cloned and inserted into the NheI/XbaI sites of pcDNA3.1(+) vector. The inserted sequence was confirmed by DNA sequence validation using CMV Forward and BGH reverse primers. The plasmid DNA was transformed into BL21 (DE3) (New England Biolabs Inc.). Fresh transformant has been picked up and cultured in 30 L LB medium (Tryptone 10 g/L, Yeast extract 5 g/L, NaCl, 10 g/L) at 37° C. Protein expression was induced by adding IPTG (Sigma) to a final concentration of 0.5 mM when culture OD600 reaches 0.6. Cells were harvested 4 hours after induction by centrifugation of 7,000 g for 30 minutes at 4° C. Thirty grams of bacterial cells expressing recombinant ER-α36 LBD-Fc in 300 ml of Protein Extract Buffer (50 mM Tris, 150 mM NaCl, 2.0M urea, 1% TritonX100, pH 8.0) were lysed by sonication (350 W, 3*45 bursts). Soluble protein was collected from supernatant after centrifugation at 20,000 g (Beckman hAvanti J-26XP) for 30 min at 4° C. and loaded onto a 20 ml CaptivA PriMAB column (RepliGen Corporation). The column was equilibrated and washed by CaptivA PriMAB Buffer A (50 mM Tris, 150 mM NaCl, pH8.0) until the A280 value reached baseline. The recombinant ER-α36 LBD-Fc protein was then eluted from CaptivA PriMAB column by CaptivA PriMAB Buffer B (100 mM glycine, pH2.5). Protein elution fractions were pooled together and finally exchanged to the storage buffer by dialysis. The final purified protein was dialyzed and stored in the storage buffer (PBS pH7.3) at −80° C.

FC_LBD-ER-α36

Fc was fused to the N terminal of the ER-α36 ligand binding domain by a recombinant method. The plasmid pET30a-Fc-ER-α36 LBD was constructed using the following method: The plasmid DNA was transformed into BL21 (DE3). Fresh transformant has been picked up and cultured in 30 L LB medium at 37° C. Protein expression was induced by adding IPTG to a final concentration of 0.5 mM when culture OD600 reaches 0.6. Cells were harvested 4 hours after induction by centrifugation of 7,000 g for 30 minutes at 4° C. Thirty grams of bacterial cells expressing recombinant Fc-ER-α36 LBD in 300 ml of Protein Extract Buffer (50 mM Tris, 150 mM NaCl, 2.0M urea, 1% TritonX100, pH 8.0) were lysed by sonication (350 W, 3*45 bursts). Soluble protein was collected from supernatant after centrifugation at 20,000 g (Beckman hAvanti J-26XP) for 30 min at 4° C. and loaded onto a 20 ml CaptivA PriMAB column. The column was equilibrated and washed by CaptivA PriMAB Buffer A (50 mM Tris, 150 mM NaCl, pH8.0) until the A280 value reached baseline. The recombinant Fc-ER-α36 LBD protein was then eluted from CaptivA PriMAB column by CaptivA PriMAB Buffer B (100 mM glycine, pH2.5). Protein elution fractions were pooled together and finally exchanged to the storage buffer by dialysis and stored in the storage buffer (PBS pH7.3) at −80° C.

ER-α36 Recombinant Cells Preparation

Human ER-α36 full length gene was cloned into BamH I/Not I sites of pcDNA3.1(+) vector and inserted sequence was confirmed by DNA sequence validation using T7 Forward and BGH reverse primers (Invirogen). Human ER-α36 with N-terminal myc tag and kozak sequence was also cloned and inserted into the NheI/XbaI sites of pcDNA3.1(+) vector. The inserted sequence was confirmed by DNA sequence validation using CMV Forward and BGH reverse primers.

CHOK1, NIH3T3 or HEK293 cells (ATCC) were cultured to about 75% confluence or 1×10$^6$ cells/ml and then the cells were transfected with ER-α36 DNA plasmid by Lipofectamine 2000 (Invitrogen) for CHOK1 and NIH3T3, or by PEI (Polyscience) for HEK293.

For stable cell line development, the cells were passed 24 hours post transfection and switched to fresh selection medium with 800 μg/ml of G418 (Gibco). The selection medium was refreshed every 3 days and selection procedure was continued for 2-3 weeks, then the transfectants were subcloned by limiting dilution in 96-well plates at 1 cell/well. The subclones from single colony growth well were expanded into 6-well plates and screened by flow cytometry. 4-5 positive clones were further expanded, cryopreserved and maintained for stability test.

For transient transfection, the transfected cells were cultured for additional 48 hours in complete culture medium. Then part of the cells was harvested and cell lysate was prepared for western blot for transfetion efficiency and expression level test using ER-α36 specific antibodies or cmyc fusion tag antibody (Abcam). 72-96 hours later, the cells were harvested for animal immunization, cell based binding assays or for cell lysate preparation.

Example 2 Antibody Generation and Screening

Antigen and Immunogen Preparation

To maximize the diversity of antibodies to be generated against ER-α36, three different types of antigens were used for ER-α36 antibody production, including: 1) ER-α36 derived C-terminal peptides, 2) recombinant ER-α36 protein containing both ligand-binding domain and C-terminal 27 amino acids, and 3) cell lines expressing full length ER-α36 protein established using transient or stable transfection or naturally occurring cell lines expressing high levels of ER-α36 protein on membrane.

ER-α36 derived C-terminal peptides with the following sequences seq#1) GISHVEAKKRILNLHPKIFGNKWF-PRVC and 2) GISHVEAKKRILNLHPKIFGC were synthesized using solid chemistry method and conjugated with keyhole limpet hemocyanin (KLH) (Sigma). The peptide synthesized had more than 95% purity by Mass Spec (Waters). The synthetic peptide of C-terminal 27aa was then conjugated to KLH carrier protein via a heterobifunctional linker. The unconjugated peptide and linker were removed by dialysis the conjugate against PBS, pH 7.2. The purified recombinant LBD-containing ER-α36 protein was produced using methods shown in Example 1.

Animal Immunization:

The recombinant protein and the synthesized KLH conjugated peptide were then used as immunogen for immunization of C57BL/6, Balb/c, and SJL mice (Slac laboratory animal, Ltd, Shanghai). In brief, the immunogens were emulsified with complete or incomplete Fraund's adjuvant (Sigma) at equal volume, then immunized animals s.c. or i.p. at 100 ul/injection and dosage of 50-100 ug/animal/injection. Immunization occurred at least every 2-3 weeks, and test bleed and ELISA test were carried out 7 days after each boost immunization.

For cell based immunization, NIH3T3 or CHOK1 cell line was transient transfected with full length human ER-α36. After 2 days of transfection, part of the cells was harvested for western blot analysis with ER-α36 specific antibody to confirm ER-α36 expression. After 3 days of transfection, the cells were harvested and washed twice with RPMI 1640 basal medium (Gibco). Selected mouse strains C57BL/6, Balb/c and SJL mice (Slac laboratory animal, Ltd, Shanghai) were immunized at $(5-10)\times10^6$ cells/animal/injection, i.p. immunization was performed at least once every 2-3 weeks, and test bleed and FACS (BD Bioscience) or Acumen assay (TTP LabTech) was carried out 7 days after each boost immunization. Fresh ER-α36 transfectants were prepared right before each scheduled immunization or test bleed analysis.

Fusion:

4 days prior to fusion, each mouse was boosted intraperitoneally with ER-α36 protein or 27 aa peptide-KLH conjugate or recombinant ER-α36 protein in PBS. On the fusion day, the spleen was removed aseptically and the organ was processed into a single cell suspension. After washing, the cells were suspended in DMEM basal medium (Gibco) and mixed with SP2/0 myeloma cells (ATCC) at 5:1 ratio, and the mixture was washed once with basal medium and then subjected to PEG mediated fusion. Upon completion of fusion, the cells were washed once with DMEM basal medium and resuspended in post-fusion cell growth media supplemented with 1×HAT (Sigma) and hybridoma growth factors to $0.5\times10^6$ cells/ml. 200 μl per well of the cell suspension was plated into 96 well cell culture plates and placed in a 37° C. incubator with 5% $CO_2$. After 7 days incubation, add 50 μl/well of fresh growth medium containing 1×HAT (Sigma). The fusion was screened by ELISA or Acumen microplate cytometry 10-14 days post cell fusion.

Hybridoma Screening

1. ELISA Screening

High-binding clear polystyrene 96-well plates (Nunc) were coated with 100 ul/well of purified ER-α36 LBD fusion protein, negative control protein or other counter-screening antigens (including FC-ER-α66 Ligand binding domain fusion protein, human IgG) which were diluted to 1 μg/ml in PBS, pH 7.2. The plates were incubated with coating solution overnight at 2-8° C., then washed once on a plate washer using PBS+0.05% Tween 20 (PBST, Sigma). 200 μl/well of blocking solution (PBS at pH7.4+1% BSA (Sigma)) was added to each well and incubated 1-2 hours at room temperature. The plates were emptied and 50-100 μl/well of hybridoma culture supernatant was added. After 1.0 hour incubation at 37° C., the plates were then washed 3 times (PBST) and then 100 μl/well of HRP conjugated goat anti-mouse IgG antibody (ZSGB Bio) was added. The reaction was continued at 37° C. for 1.0 hour followed by 3 times washing with PBST and addition of 100 ul/well of TMB substrate (CW bio). After 15 minutes incubation at room temperature, 100 μl/well of 1.0N HCl was added as stopping solution and the plate was read at 450 nm over an ELISA plate reader (Molecular Device). Hybridoma clones were identified that produced an antibody giving a high read-out on the ELISA screen.

2. Acumen Microplate Cytometry Screening

Human ER-α36 transfected screening cells were plated into black/clear bottom 384-well plates (Nunc) and cultured overnight at 37° C. with 5% $CO_2$. Next day, the culture medium was removed and 20 μl/well of hybridoma supernatant sample was added. After 2.0 hours incubation at 37° C., the plates were washed twice with PBS, pH 7.2, and then 15 μl/well of Alexa488 conjugated goat anti-mouse IgG (F(ab')$_2$ fragment, Invitrogen) was added following with 1.0 hour incubation at 37° C. The plates were then washed 3-4 times with PBS and the cells were then fixed with 4% Paraformaldehyde (Sigma) and stained again with PI (DO-JINDO) for 1.0 hour at 37° C. The assay plates were read with Acumen microplate cytometer (Acumen eX3, TTP LabTech). Hybridoma clones were identified that produced an antibody giving a high read-out on the Acumen microplate cytometry screening.

Subcloning:

The selected positive hybridoma clones from ELISA and/or Acumen screening were subcloned by limiting dilution in 96-well cell culture plates. After 7-10 days culture, the subcloning plates were screened by ELISA or Acumen assay. Two positive clones with single colony growth for each parental clone were expanded into 24-well plates for additional confirmation assays, isotyping and then further expansion into culture flasks for cryopreservation.

Production and Purification:

Antibody production for the selected hybridoma cell line was performed using roller bottle (Corning) cell culture with hybridoma culture medium (SFM, Gibco). After 2-3 weeks of culture, the culture medium was harvested and the cells and cell debris were removed with ultrafilters. The clarified supernatant was then concentrated by ultrafiltration and uploaded onto a prepared Protein A-sepharose column (GE Healthcare Life Science). After washing with equilibration buffer to baseline under monitoring by a UV monitor, the column was then eluted with 0.1 M citric acid, pH3.5, and the eluted antibody was immediately neutralized with 1.0 M Tris-HCl buffer, pH 8.0, and dialyzed against PBS, pH 7.2 (Invitrogen), overnight at 2-8° C. with 2 buffer exchanges. The purified antibody was filtered through 0.22 um sterile syringe filters and stored in aliquots at −80° C. or below. The purified antibody was named SNGmB1. Samples of the antibody products were submitted to QC tests including purity, concentration, binding ability to protein and cell based antigens, in vitro potency assays, etc. The QC analysis result is shown in FIG. 2.

Example 3 Characterization of the Binding of SNGmB1 to ER-α36

The binding activities of the anti-ER-α36 antibody SNGmB1 to ER-α36 were characterized in this example from different aspects listed below.

a) Binding Specificity of SNGmB1 Using ELISA

The binding specificity of SNGmB1 was assessed using ELISA assay. Five different proteins were used to coat the assay plate at 1 μg/ml. After extensive blocking, the SNGmB1 antibody of different concentrations (10, 2, 0.4, 0.08 and 0.016, 0.004 μg/ml) was added to the assay plate and incubated for 1.5 hours, followed by detection of complex formation using HRP (horse radish peroxidase) labeled anti-mouse IgG Fc (Invitrogen). An example of the data was shown below in FIG. 3. SNGmB1 was shown to bind to 27-amino acid peptide derived from the F domain of ER-α36 ("peptide" in FIG. 3) and also to Fc-LBD protein ("Fc-LBD" in FIG. 3), but not to Fc-LBD with 27 amino acids deleted ("Fc-LBD-D27" in FIG. 3) or to Fc-ER-α66 protein ("Fc-ER66" in FIG. 3) or to the control human IgG protein ("Human IgG" in FIG. 3). Thus, SNGmB1 specifically bound to the 27-amino acid peptide of the C-terminal F domain of ER-α36. The key epitope residues in ER-α36 F domain for SNGmB1 binding have been mapped using both PepScan and Alanine Scan (see Example 5).

b) Western Blot Analysis:

The binding specificity of antibody SNGmB1 was further assessed using western blot analysis of whole cell lysates from a panel of human cancer cell lines. The following lysates were used: 1) parental HEK293 cells; 2) HEK293 cells transfected with pcDNA3.1_ER-α36 full length protein with Myc-tag; 3) MDA-MB-231(ATCC); 4) MCF-7 (ATCC); 5) Hec-1A (ATCC); 6) K562 (ATCC).

Cell lysates from different cell lines were prepared by aspirating the culture media and washing cells with PBS, followed by placing the cells on ice for 30 minutes in lysis buffer (PBS+1% NP40 and 0.7 mM EDTA+1% protease inhibitor cocktail) (Roche). The lysates were clarified by spinning at 14000 rpm in an Eppendorf centrifuge for 10 minutes at 4° C. to collect the supernatant. After protein quantification, 50-100 μg of the protein lysates were mixed with 5×SDS-PAGE gel loading buffer (Bio-rad) and loaded onto 10% polyacrylamide gel for electrophoresis followed by transferring to PVDF membrane. The PVDF membrane was then washed with TBS+0.1% Tween 20 (PBST) and non-specific binding were blocked with buffer containing PBS+0.1% Tween 20+5% fat free milk at 4° C. overnight. The primary SNGmB1 was then added to TBST with 1% fat free milk to a final concentration of 1-2 μg/ml and incubated with the membrane at 4° C. overnight for 2 hours. The membrane was then washed 3 times for 10 minutes each in TBST with gentle shaking; and then secondary HRP conjugated goat antibody against mouse or human Fc (ZSGB Bio) were added into TBST with 5% fat free milk and incubated at room temperature for 2 hours, washed with TBST 3 times for 5 minutes each with gentle rotation before incubating with ECL substrate (Millipore) for detection.

Figure 4:
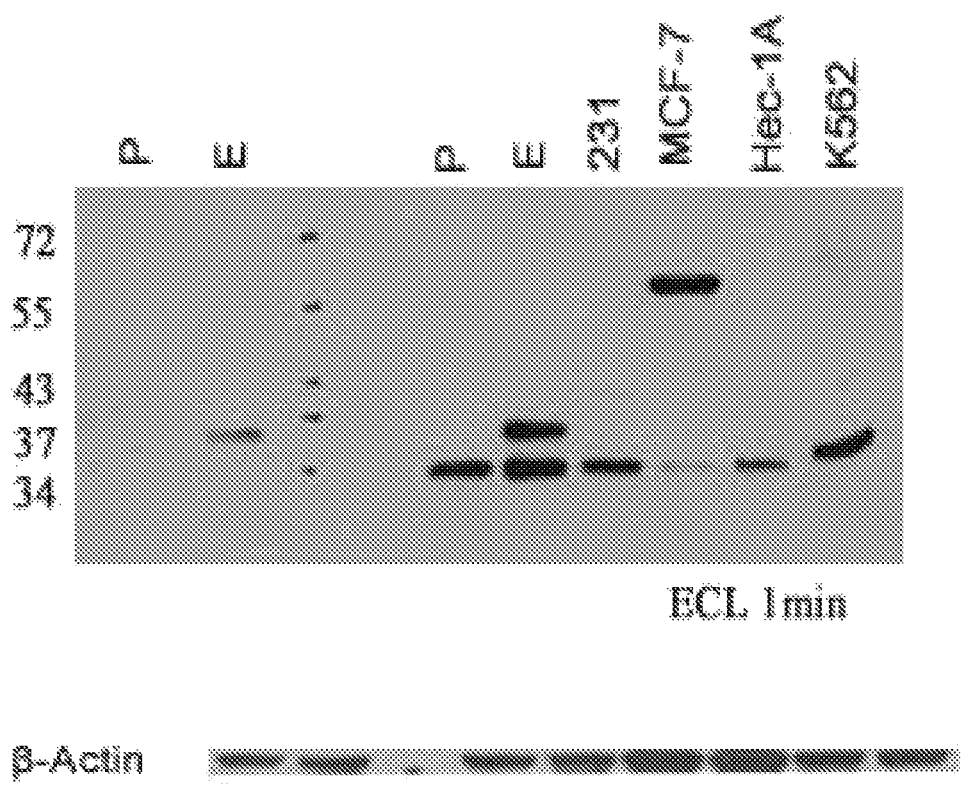
FIG. 4 shows binding specificity of SNGmB1 with western blot. The following lysates were used: 1) parental HEK293 cells ("P"); 2) HEK293 cells transfected with pcDNA3.1_ER-α36 full length protein with Myc-tag ("E"); 3) MDA-MB-231 ("231"); 4) MCF-7; 5) Hec-1A; 6) K562.

As shown in FIG. 4, the transfected ER-α36 protein with myc-tag was detected with anti-Myc (Abcam) as around 37 KD. The endogenous ER-α36 band was detected in all of the cells tested at 36 KD. The only other band detected was a band between 55 and 72 KD. This band was likely a chimeric protein of ER-α66 with the F domain from ER-α36 or another protein with similar epitope and its identity to be further defined.

c) FACS Analysis of ER-α36 Expression

Also examined were the binding of SNGmB1 to a series of human cancer cell lines including K-562 cell, a cell line derived from chronic myeloid leukemia patient; MCF7: a breast cancer cell line expressing both ER-α66 and ER-α36; SKBR3 (ATCC): a breast cancer cell line expressing high levels of HER2; and MHCC97H (ATCC): a highly metastatic hepatocellular carcinoma cell line. These cell lines were found to express ER-α36 protein by western blot.

These cell lines (K562, MCF7, SKBR3, MHCC97H) were cultured in their respective medium to 90% confluence and then the cells were washed with PBS, followed by pretreatment with 0.5 mM EDTA (adherent cell lines) to facilitate removal from substrate. The cells are then collected and centrifuged at 2500 rpm for 5 minutes at 4° C. After counting the cell number, the cells were then resuspended in the block buffer (10% normal goat serum, Invitrogen) to a final concentration of 5-10×10$^6$ cells/ml, and 100 μl of cells (5×10$^5$) were transferred to a 1.5 ml EP tube for staining. All those tubes (cells in block buffer) were then laid in a revolver (Grant) for 30 minutes at 4° C. After that the cells were centrifuged at 2500 rpm for 5 minutes at 4° C., the supernatant was discarded, 100 μl of the primary antibody was then added to (1-30 μg/ml final concentration, SNGmB1 or mouse IgG2b isotype control) and incubated in a revolver at 4° C. for 1 hr. The cells were then collected by centrifugation at 2500 rpm for 5 minutes at 4° C. and washed 2 times with PBS solution. The goat anti mouse IgG (H+L) FITC secondary antibody (Invitrogen) were then added at a dilution range of 1:400-800 followed by incubation in a revolver at 4° C. for 1 hr and kept in dark. Following this incubation, free antibody was the removed by washing the cells twice with PBS and the cells were then fixed in 1% paraformaldehyde at room temperature for 10 min and before resuspending the cells in 200-400 μl PBS with 5 μl 7-AAD (BD Biosciences) added for final flow cytometric analysis.

Figure 5C:
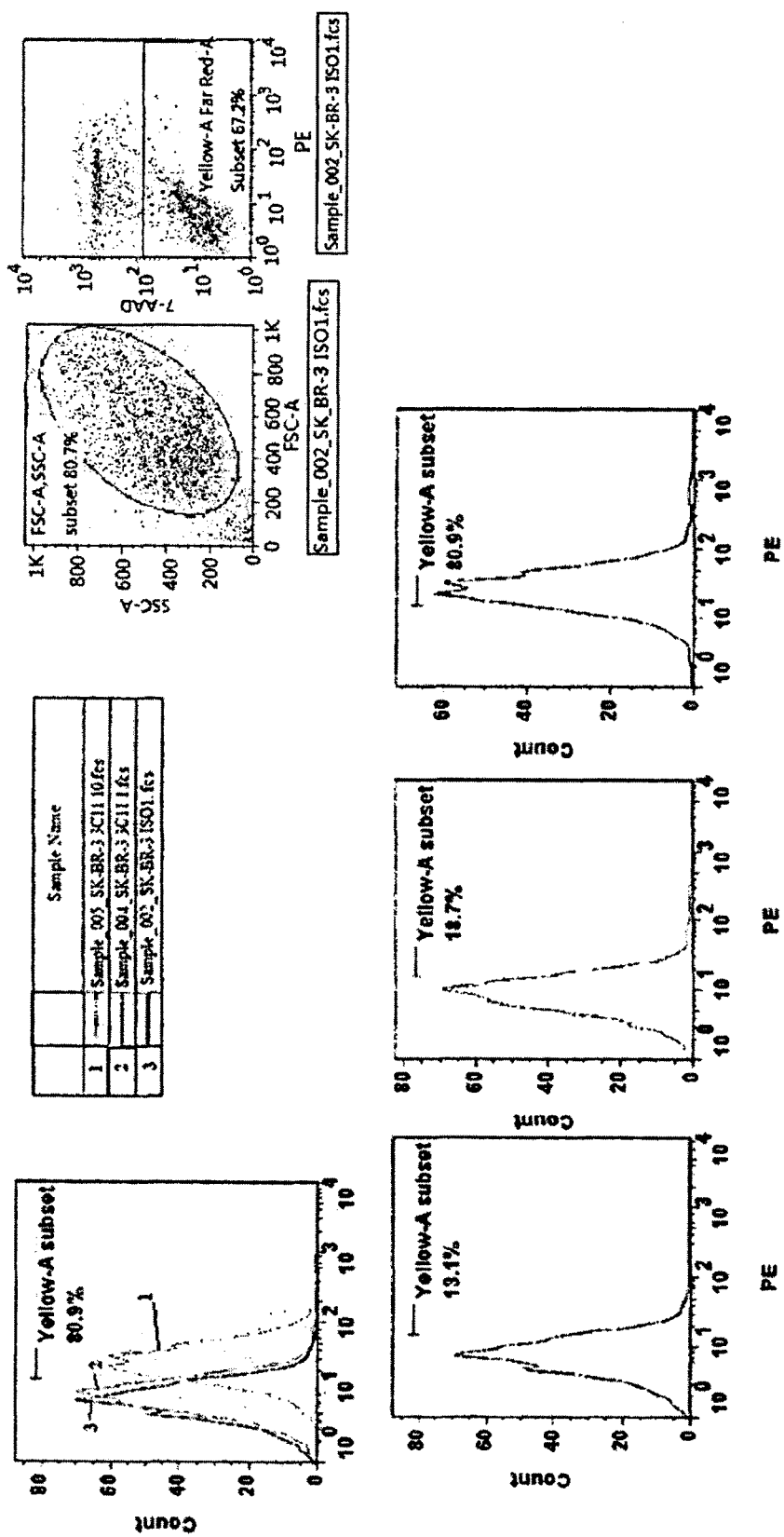
FIG. 5 shows the binding of SNGmB1 to ER-α36 expressed on cell surfaces of: K562 cells (FIG. 5A); MCF7 cells (FIG. 5B); SKBR3 cells (FIG. 5C); MHCC97H (FIG. 5D); 3T3 inducible cell lines (FIG. 5E), as measured by FACS analysis. The SNGmB1 antibody showed dose-dependent binding to K-562 in the FACS assay. Mouse IgG2b was used as isotype control.
Figure 5D:
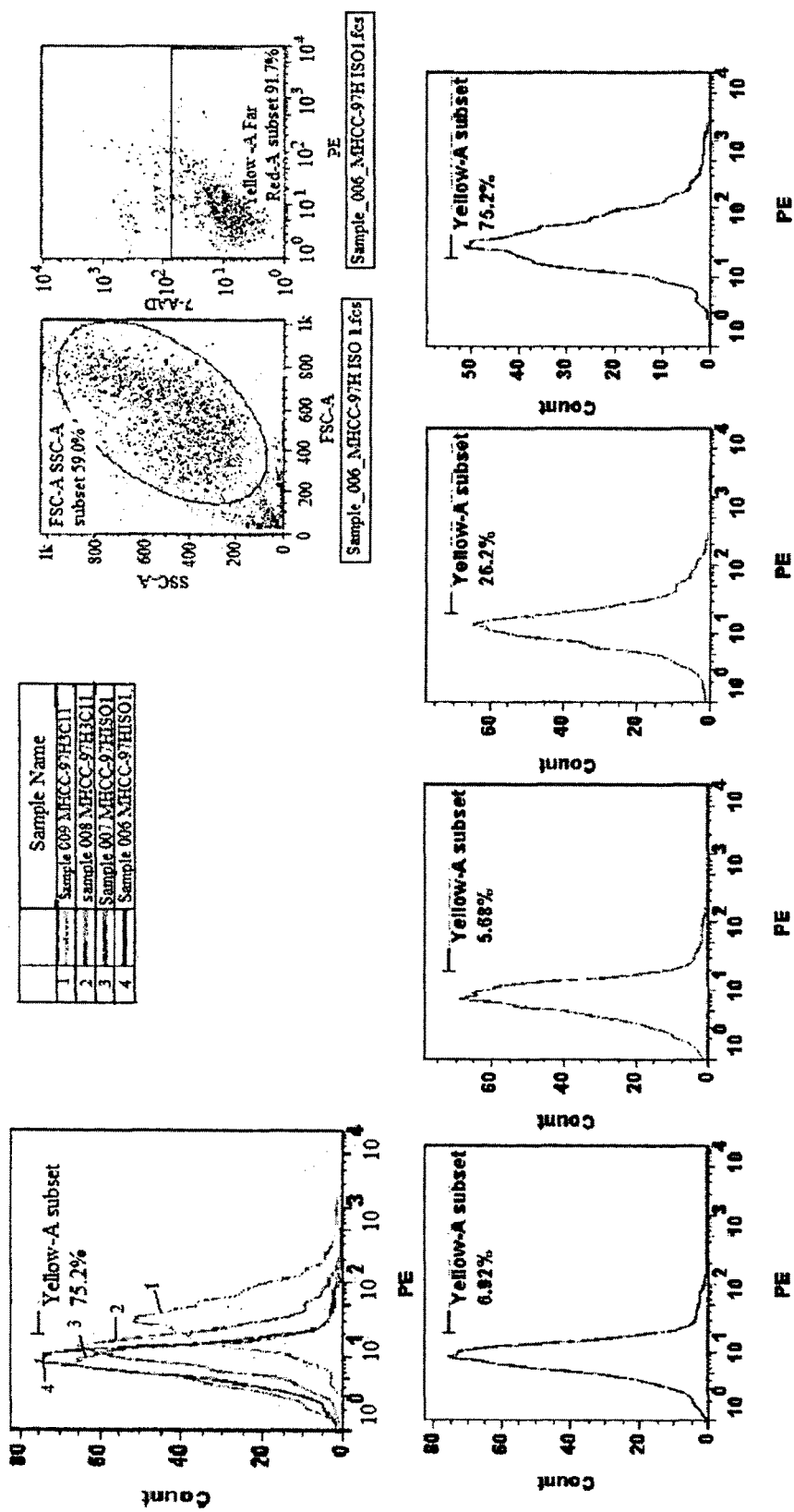
Figure 5E:
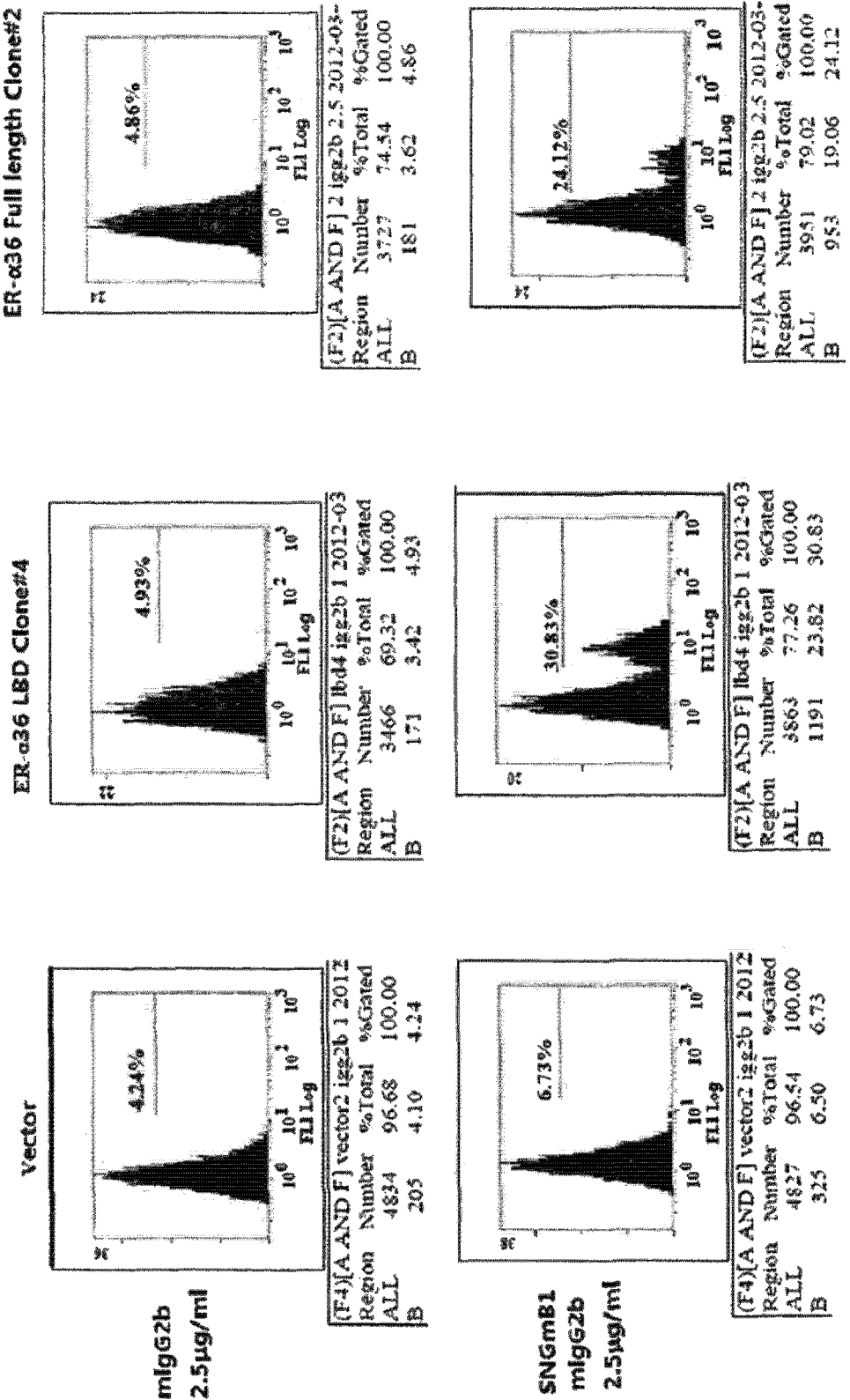

SNGmB1 antibody with a series of concentration (100, 20, 4, 0.8, 0.16, 0.032 μg/ml) was tested and showed dose-dependent binding to K562 cells in the FACS assay (see FIG. 5A). In FIG. 5A, the "Geom. Mean" refers to Geometric mean fluorescence intensity. The specific binding of SNGmB1 antibody to the other tested human breast cancer cell lines was also confirmed, see FIG. 5B (MCF7), 5C (SKBR3) and 5D (MHCC97H). To better characterize the specific binding of the antibody, we established stable 3T3 cell lines which can be induced to express human ER-α36 protein. The cell line was incubated with the SNGmB1 antibody and the binding was tested, according to the similar procedure described above. Mouse IgG2b was used as isotype control. Results showed that SNGmB1 antibody specifically bound to cell line as well (see FIG. 5E).

d) Immunoflurenscence Analysis

The ability of SNGmB1 to detect membrane bound ER-α36 protein in MCF-7 cells was assessed using immunostaining. MCF-7 mammosphere was formed and immunostaining was performed by steps as follows:

1. MCF-7 cells were cultured in DMEM without phenol red for 2 days and stained with 7-aminoactinomycin D (7-AAD) followed by FACS sorting. The sorted cells were cultured in DMEM/F12 without phenol red medium (Gibo) with B27 (Invitrogen), EGF (BD Biosciences) and bFGF (BD Biosciences) for 6 days and the MCF-7 mammosphere was formed.

2. MCF-7 mammosphere was centrifuged at 1000 rpm for 4 min, and the supernatant was removed.

3. The mammosphere was washed with 500 μl PBS and was transferred to a 1.5 ml EP tube before centrifugation at 1000 rpm for 4 min, and the supernatant was discarded.

4. The precipitate was fixed with 500 μl paraformaldehyde (4%) for 20 min (or overnight), and was centrifuged at 1000 rpm for 4 min to move the supernatant.

5. The precipitate was washed with 500 μl PBS and centrifuged at 1000 rpm for 4 min, and the supernatant was discarded, wash three times using PBS.

6. The supernatant was removed and the precipitate was incubated with 50 μl goat serum blocking solution at 37° C. for 30 min; after centrifugation at 1000 rpm for 4 min, the supernatant was discarded.

7. The mammosphere was incubated with SNGmB1 (working concentration: 10 μg/mL) at 4° C. overnight.

8. On the next day, the mammosphere was centrifuged at 1000 rpm for 4 min, and washed with 500 μl PBS for three times.

9. The goat anti-mouse IgG (H+L) FITC secondary antibody (Invitrogen) Secondary antibody (5 μg/ml) was added and incubated at 37° C. for 30 min.

10. After centrifugation at 1000 rpm for 4 min, 20 µl Hoechst was added dropwise to the precipitate, and was placed at room temperature for 20 min.

11. The mammosphere was washed with 500 µl PBS for three times.

12. The mammospheres was transferred to small observation dish, and stored at 4° C. to be detected.

Figure 6A:
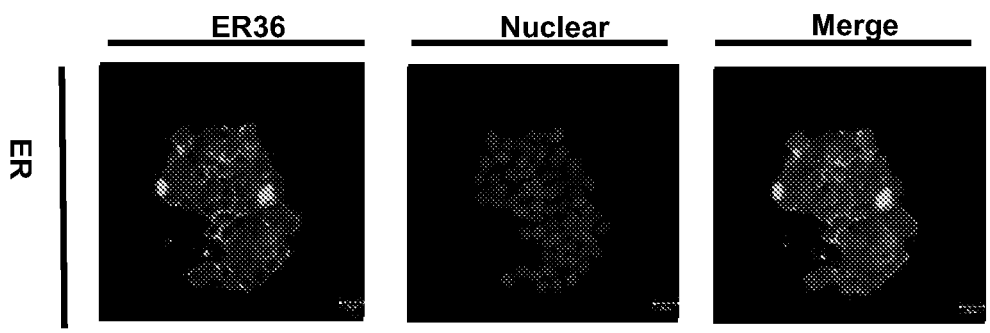
FIG. 6A shows that SNGmB1 can detect membrane bound ER-α36 on MCF7, as demonstrated in fluorescence signal.
Figure 6B:
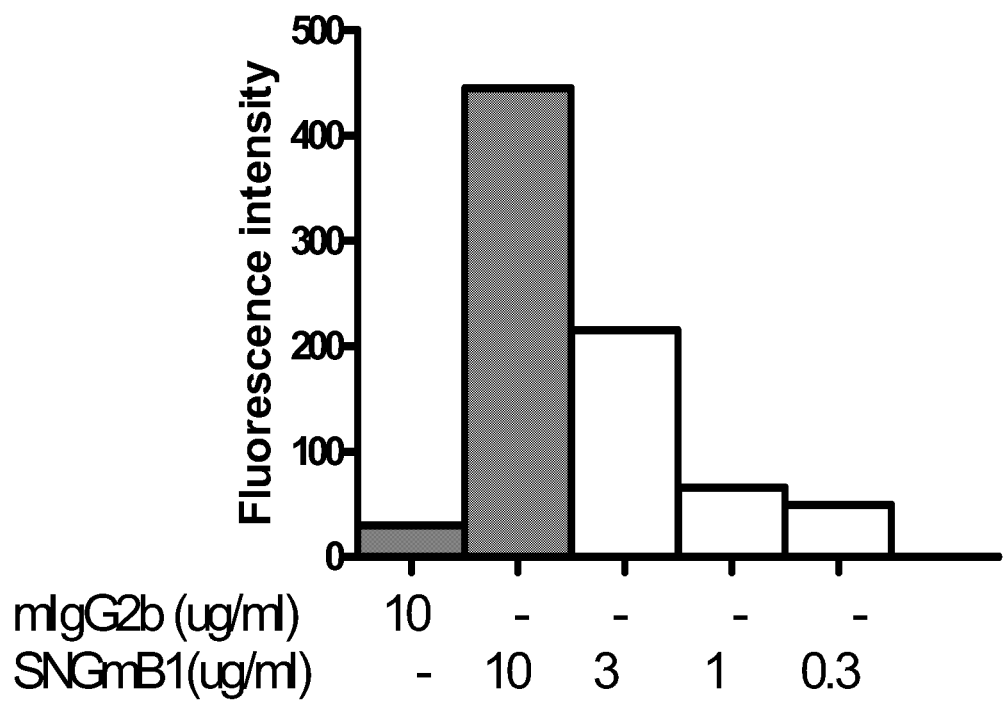
FIG. 6B shows the quantified fluorescent intensity in FIG. 6A.

As shown in FIG. 6A, clear membrane staining was observed in most of the cells. SNGmB1 stained the MCF-7 mammospheres in a dose-dependent manner (see FIG. 6B).

e) Internalization Analysis

As the development of antibody drug conjugate relies on the carrier antibody to be internalized to deliver the chemotherapeutic agent into the tumor cells, the ability of SNGmB1 being internalized by K-562 cells was also assessed.

Figure 7:
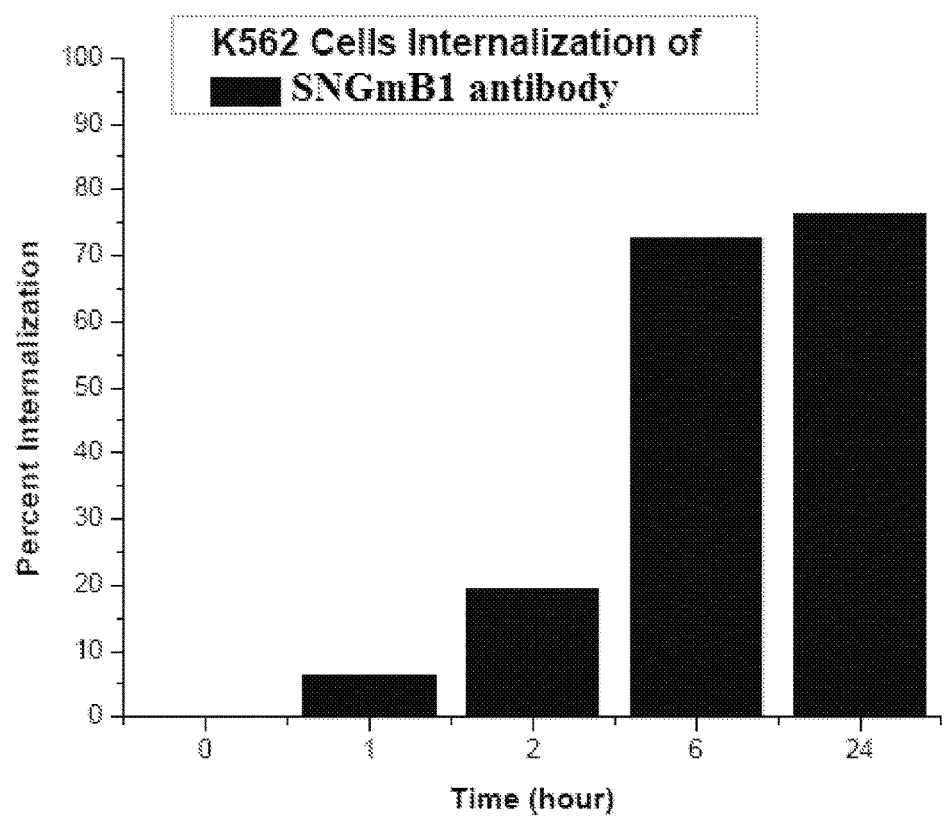
FIG. 7 shows the time-dependent internalization of SNGmB1 in K-562 cells. The % internalization=(Qn-Qo)/(Nn-Qo); Qn=MFI (Mean Fluorescence Intensity) for a sample at a specific time point, after quench; Nn=MFI for a sample taken at a specific time point, no quench; Qo=MFI for sample incubated only on ice at 0 hour, after quench.

K562 cells were first cultured in normal IMDM medium for 24 hours. On the second day, the cells are collected by centrifugation and washed once with warm PBS, followed by resuspending into culture medium with IMDM without phenol red (Gibco) supplemented with 2.5% charcoal-stripped FBS (Gibo) without phenol red. After culturing for 48 hours, the cells were collected and centrifuged for 5 minutes at 1000 rpm. The cells were then incubated with AlexaFluro488-labelled anti-ER-α36 antibody SNGmB1 37° C. for different time (1, 2, 4, 6, 24 hours) to allow internalization to occur. The internalization was stopped by putting the cells on ice. Antibody internalization analysis of SNGmB1 by K562 cells was performed by surface fluorescence quenching and measured by MFI as detected by FACS. An anti-anti-AlexaFluro488 antibody was used to quench the AlexaFluro488-labeled SNGmB1 antibody bound on the K562 cell surface. The results were shown in FIG. 7, which demonstrated time-dependent increase in the percentage of internalized antibody and peaked at ~75% of the bound antibody by 24 hours.

Example 4 Functional Testing of Neutralizing Anti-ER-α36 Antibodies Using Estradiol Stimulated MCF7 Mammosphere Formation Assay The impact of antibody on the formation and growth of cells was evaluated by Estradiol stimulated MCF7 mammosphere formation assay.

MCF-7 (ATCC) maintained in DMEM medium containing 10% FBS (Gibco) have been passaged 2-3 times prior to assay and are 60% confluence. MCF-7 cells were washed with warm phenol red-free DMEM twice and then grew in phenol red-free DMEM with 2.5% charcoal stripped FBS (CFBS) for 48 hours. The cells were then trypsinized and passed through 40-µm filters to remove cell clumps, followed by stained with 7-AAD and 800 cells were plated into each well of ultra-low binding 24 well plates (Corning Inc.) in 800 µl mammosphere growth medium consisting of serum free DMEM-F12 (Gibco) supplemented with 5 µg/ml insulin, 0.4% bovine serum albumin (Sigma), B27 (Invitrogen), 20 ng/ml EGF and bFGF (BDBiosciences). For the evaluation of antibody activity, 1 nM estradiol in DMSO was added to each well to induce mammosphere formation after adding of antibodies.

Figure 6C:
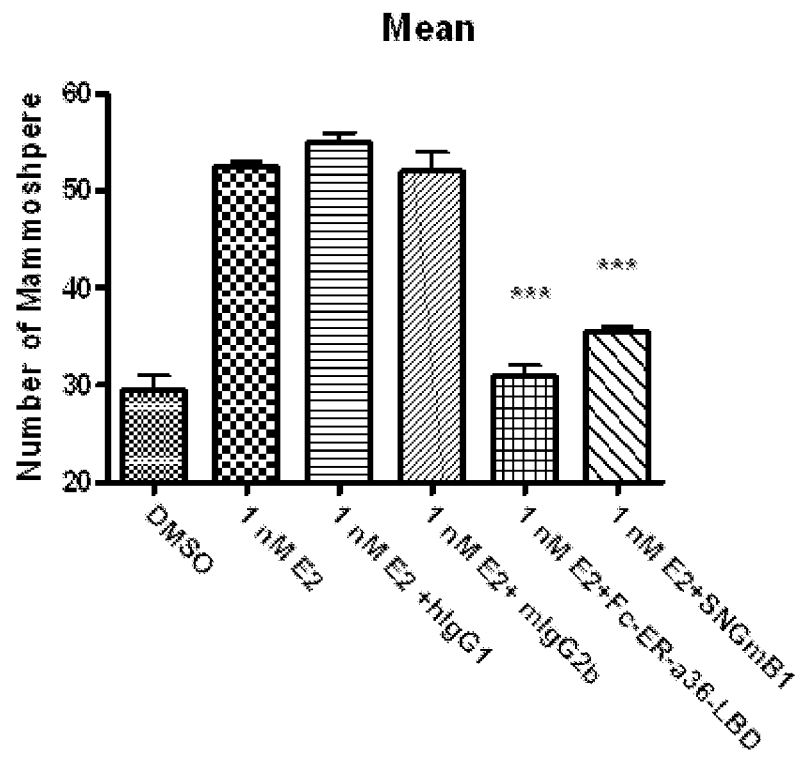
FIG. 6C shows that SNGmB1 antibody can inhibit on MCF7 mammosphere formation and growth.

MCF7 cells were grown in the presence of 1 nM estradiol and PBS, human IgG, mouse IgG2b, recombinant ER-α36 ligand binding domain Fc fusion protein, or SNGmB1. DMSO was used as negative control. After 72 hr treatment, the number of mammosphere in culture was counted. SNGmB1 and recombinant ER-α36 ligand binding domain Fc fusion protein significantly inhibited estradiol stimulated MCF7 mammosphere formation compared with human IgG and mouse IgG2b. (FIG. 6C)

Figure 6D:
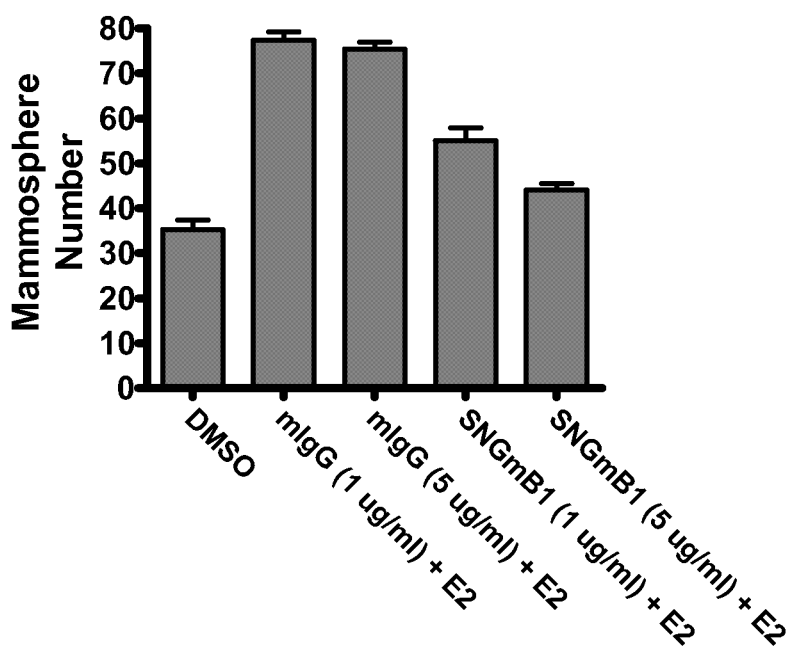
FIG. 6D shows that SNGmB1 antibody can inhibit on MCF7 mammosphere formation and growth at different concentrations.

The antibody activity was also evaluated in a longer term of 7 days by following methods: MCF7 mammosphere was prepared using same method described above. For the evaluation of antibody activity, 100 ul of 10× concentrated antibody stock solution in mammosphere growth medium are then added to each well and allowed to incubate for 2 hours. After that 100 ul of 10× concentrated stock of estradiol (final concentration at 100 µM or 3 nM in 0.02% DMSO) are then added to each well to stimulate mammosphere formation. 100 ul of 10× fresh antibody stock in mammosphere growth medium was added to each well on day 4. The number of mammosphere was accounted 7 days later manually with microscope. SNGmB1 showed better ability in inhibiting mammosphere formation compared with mIgG (FIG. 6D).

Example 5 Biacore Binding Assay

Figure 8:
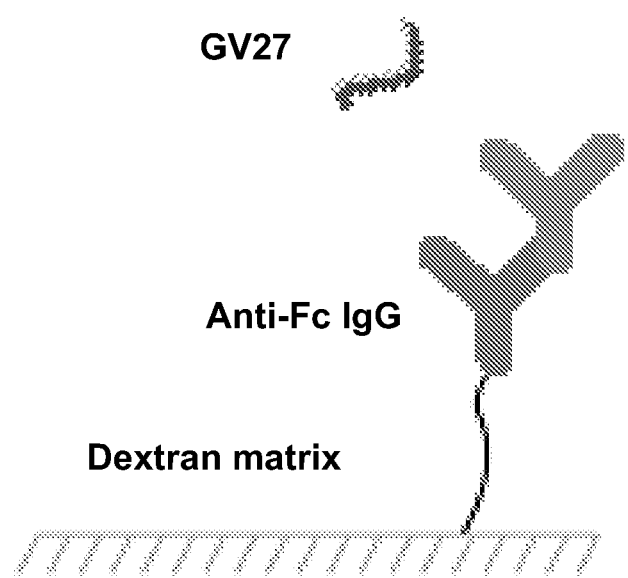
FIG. 8 shows the format of biacore assay. A chip surface was coated with anti-mouse FC IgG which captures the test antibody, and GV27 peptide (i.e. SEQ ID NO: 2) was injected over the surface to allow competition of binding for the test antibody. A chip coated with the IgG but without the test antibody was used as a control.

The affinity of SNGmB1 to its target protein was measured by Biacore. The format of Biacore assay is shown in FIG. 8. Antibody was captured on anti-mouse/human FC IgG coated surface and peptide was injected over the surface. Empty FC1 was used as a reference channel. The chip surface was regenerated with Gly 1.5.

Titration of GV27 to Captured Antibodies

A Series S CM5 sensor chip (9000RU) (BIACORE) was activated in the FC 2, FC 3 and FC 4 chips by 7-min injection (10 µl/min) of freshly prepared mixture with equal volume of 50 mM NHS and 200 mM EDC. Then 1:25 diluted Biacore anti-mouse Fc antibody (in a concentration of 25 µg/ml in 10 mM sodium acetate buffer PH 5.0) was injected onto the activated chip FC2, FC3 and FC4 cells at 10 µl/min until the signal reached 9000 Ru. Active coupling sites were blocked with 7 min injection of 1M ethanolamine at 10 µl/min. Each antibody was captured over the chip surfaces respectively (FC2, FC3 and FC4, FC1 as a reference cell) and the captured signal was around 500 RU. GV27 (ER-α36 c-terminal 27 aa, as set forth in SEQ ID NO: 2) at concentration of 0 nM, 1.5625 nM, 3.125 nM, 6.25 nM, 12.5 nM and 25 nM at 30 µl/min for 180 s of association phase and 900 s of dissociation phase. The sensor surfaces were regenerated by injecting regeneration buffer (10 mM glycine buffer with pH 1.5) for 90 s. As a control, GV27 was also injected in different concentrations over the surfaces of FC without captured antibodies. The signal from step 2 was subtracted from the control step and the result was fit using 1 to 1 binding model.

As shown in Table 3, the Kd of SNGmB1 to the 27 aa peptide (F domain) was around 100 pM (n=7).

TABLE 3

Biacore affinity data for SNGmB1

| Antibody | Lot # | $k_a$ (1/Ms) | kd (1/s) | $K_D$ (M) |
|---|---|---|---|---|
| SNGmB1 | 20110224 | 7.37E+06 | 6.23E−004 | 8.45E−11 |
|  | 20110425 | 2.93E+06 | 3.29E−04 | 1.12E−10 |
|  | 20110224 | 5.6E+06 | 4.11E−04 | 7.35E−11 |
|  | 20110329 | 5.77E+06 | 3.99E−04 | 6.92E−11 |
|  | 20110426 | 4.03E+06 | 3.38E−04 | 8.38E−11 |
|  | 20110709 | 6.5E+06 | 4.97E−04 | 7.64E−11 |
|  | 20110818 | 7.28E+05 | 1.05E−04 | 1.44E−10 |

Example 6 Epitope Mapping

The epitope bound by SNGmB1 was further analyzed using Alanine scan method. A series of peptides with serial replacement of the amino acid to alanine were synthesized and the said peptides were coated to the high binding plate and the ability of the antibody to bind to the peptides was determined. The list of peptides and their sequences were listed in Table 4.

TABLE 4

Peptide series with serial alanine mutation and their sequences.

| Peptide ID | Amino acid sequence |
| --- | --- |
| Shenogen-27aa-M1 | ALLLNSGISHVEAKKRILNLHPKIFGNKWFPRV |
| Shenogen-27aa-M2 | IALLNSGISHVEAKKRILNLHPKIFGNKWFPRV |
| Shenogen-27aa-M3 | ILALNSGISHVEAKKRILNLHPKIFGNKWFPRV |
| Shenogen-27aa-M4 | ILLANSGISHVEAKKRILNLHPKIFGNKWFPRV |
| Shenogen-27aa-M5 | ILLLASGISHVEAKKRILNLHPKIFGNKWFPRV |
| Shenogen-27aa-M6 | ILLLNAGISHVEAKKRILNLHPKIFGNKWFPRV |
| Shenogen-27aa-M7 | ILLLNSAISHVEAKKRILNLHPKIFGNKWFPRV |
| Shenogen-27aa-M8 | ILLLNSGASHVEAKKRILNLHPKIFGNKWFPRV |
| Shenogen-27aa-M9 | ILLLNSGIAHVEAKKRILNLHPKIFGNKWFPRV |
| Shenogen-27aa-M10 | ILLLNSGISAVEAKKRILNLHPKIFGNKWFPRV |
| Shenogen-27aa-M11 | ILLLNSGISHAEAKKRILNLHPKIFGNKWFPRV |
| Shenogen-27aa-M12 | ILLLNSGISHVAAKKRILNLHPKIFGNKWFPRV |
| Shenogen-27aa-M13 | ILLLNSGISHVEAAKRILNLHPKIFGNKWFPRV |
| Shenogen-27aa-M14 | ILLLNSGISHVEAKARILNLHPKIFGNKWFPRV |
| Shenogen-27aa-M15 | ILLLNSGISHVEAKKAILNLHPKIFGNKWFPRV |
| Shenogen-27aa-M16 | ILLLNSGISHVEAKKRALNLHPKIFGNKWFPRV |
| Shenogen-27aa-M17 | ILLLNSGISHVEAKKRIANLHPKIFGNKWFPRV |
| Shenogen-27aa-M18 | ILLLNSGISHVEAKKRILALHPKIFGNKWFPRV |
| Shenogen-27aa-M19 | ILLLNSGISHVEAKKRILNAHPKIFGNKWFPRV |
| Shenogen-27aa-M20 | ILLLNSGISHVEAKKRILNLAPKIFGNKWFPRV |
| Shenogen-27aa-M21 | ILLLNSGISHVEAKKRILNLHAKIFGNKWFPRV |
| Shenogen-27aa-M22 | ILLLNSGISHVEAKKRILNLHPAIFGNKWFPRV |
| Shenogen-27aa-M23 | ILLLNSGISHVEAKKRILNLHPKAFGNKWFPRV |
| Shenogen-27aa-M24 | ILLLNSGISHVEAKKRILNLHPKIAGNKWFPRV |
| Shenogen-27aa-M25 | ILLLNSGISHVEAKKRILNLHPKIFANKWFPRV |
| Shenogen-27aa-M26 | ILLLNSGISHVEAKKRILNLHPKIFGAKWFPRV |
| Shenogen-27aa-M27 | ILLLNSGISHVEAKKRILNLHPKIFGNAWFPRV |
| Shenogen-27aa-M28 | ILLLNSGISHVEAKKRILNLHPKIFGNKAFPRV |
| Shenogen-27aa-M29 | ILLLNSGISHVEAKKRILNLHPKIFGNKWAPRV |
| Shenogen-27aa-M30 | ILLLNSGISHVEAKKRILNLHPKIFGNKWFARV |
| Shenogen-27aa-M31 | ILLLNSGISHVEAKKRILNLHPKIFGNKWFPAV |
| Shenogen-27aa-M32 | ILLLNSGISHVEAKKRILNLHPKIFGNKWFPRA |
| Shenogen-27aa-Rhesus macaque | GISHVEAKKRILNLHPKIFGNKWFPRV |

Peptide Based Epitope Mapping: Alanine Scan

Figure 9:
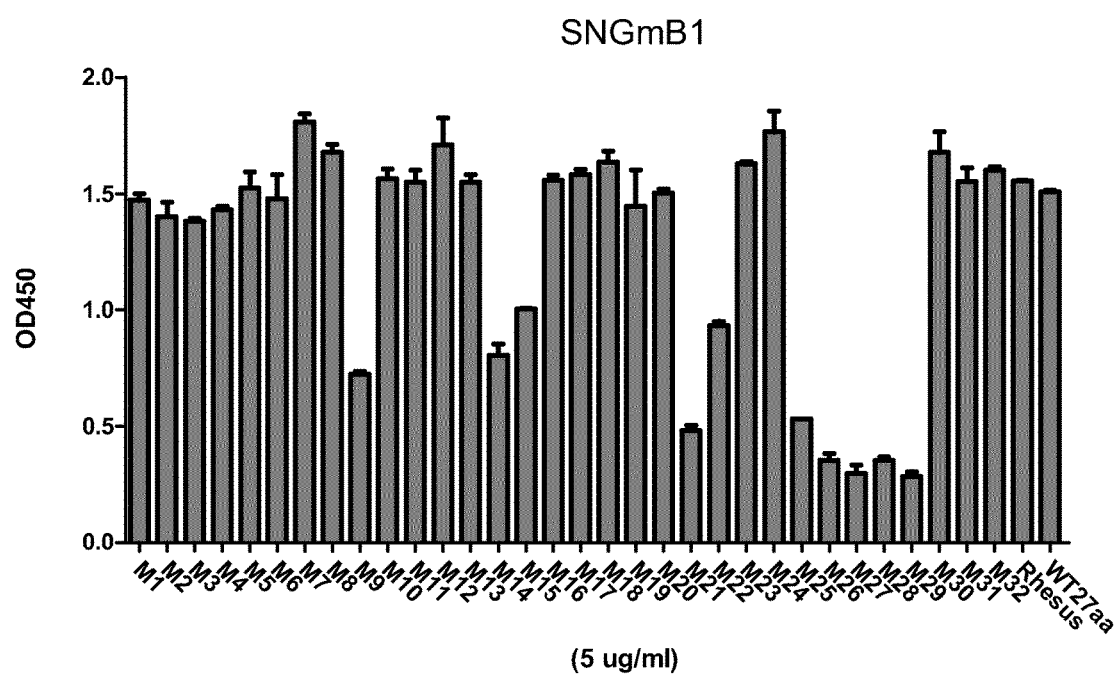
FIG. 9 shows the epitope mapping results by alanine scanning. Binding of SNGmB1 to a series of mutated peptides derived from ER-α36 comprising the C-terminal 27 amino acids was tested.

The binding of SNGmB1 to above peptides with serial replacement of the amino acid to alanine was studied using following method: clear polystyrene plates (Nunc) were coated with (50 µl/well) of a 5 µg/ml peptide solution in PBS consisting of one of the 33 peptide in the list. The plates were incubated with coating solution overnight 4° C. Then the plates were washed once on an automatic plate washer using PBS+0.05% Tween 20 (Sigma). 200 µl of block solution consisting of PBS+1% BSA+0.5% Tween 20 (Sigma) was added to each well and incubated for 1 hour at 37° C.). 50 µl of tested SNGmB1 with 10 µg/ml in blocking solution were added in the plate and incubate for 1 hour at 37° C. and then wash the plate 3 times with PBS containing 0.05% Tween20. Then, 100 µl of goat anti-mouse-IgG-Fab-HRP (ZSGB Bio) was added to each well and the plate was incubated at 37° C. for 1 hr. After washing the plate 3 times with PBS with 0.05% Tween 20, 100 µl/well TMB substrate was added to each well and the plate was then incubated at RT for 15 min. The plate was added with 50 ul/well stop solution and read on a plate reader. The result is shown in FIG. 9.

Example 7 Antibody Gene Cloning and Sequence

The sequences of the SNGmB1 light chain and heavy chain variable regions were obtained by the polymerase chain reaction (PCR) amplification technique known as 5' RACE (rapid amplification of cDNA ends). Total RNA from SNGmB1 antibody producing hybridoma cell were isolated using Trizol (Invitrogen) and cDNA was synthesized using Superscript first strand synthesis system (Invitrogen) with Oligo (dT)12-18 primer. The variable regions of mouse IgG gene were cloned by PCR with MulgG VH3'-2 and Mulg-5' leader primers for heavy chain variable region and MulgK VL3'-1 and Mulg-5" leader primer for light chain variable region (NOVAGEN). The resulting band was cloned into TOPO TA cloning vector and DNAs from more than 10 clones were submitted for sequencing and determined using ABI DNA sequencing instruments (life technologies). Consensus sequences were determined using Vector NTI Advance 10 software (Invitrogen). After sequencing analysis and confirmation, the variable region of the SNGmB1 gene was cloned into a recombinant expression vector (VL into pCP-mCK; VH into pCP-mCg2a) for antibody production and purification.

The heavy chain and light chain sequences are set forth in SEQ ID NOs: 16-19. The antibody was isotyped as mouse IgG2b. To facilitate the secretion of the antibody, a signal peptide (MGWSCIILFLVATGVHS) was fused at N-terminal of the antibody.

Example 8 Expression and Purification of Recombinant Antibody Protein in 293E6 Cells The expression and purification of a recombinant antibody protein were conducted by following methods: HEK293E cells cultured in Freestyle 293 Expression Medium with 10% of Pluronic F-68 (Gibco) at $1\times10^6$ cell/ml were transfected with equal amount of heavy chain vector and light chain vector DNA at final concentration of 0.5 µg/ml and PEI (Polyethylenimine-linear, Polyscience) at 1.0 µg/ml. DNA to PEI ratio was 1:2. DNA and PEI complexes formed period with Optimal MEM should be 15 minutes at the room temperature. Transfected cells were cultured in the flasks with 5% CO2, 37° C. and 125 rpm shaking speed. 1% Peptone medium was added at 22 to 26 hours post transfection. Conditioned medium was harvested on day 6 and supernatant was centrifuged at 3,000 rpm for 30 minutes. The clarified conditioned medium were then loaded onto nProteinA column (G.E. Healthcare), washed with PBS plus 0.1% triton-X100 and finally the bound IgG was eluted with a solution containing 0.1M glycine at pH 3.5. The eluted antibody protein was dialyzed to PBS and stored at −80*C. To remove endotoxin, the purified protein was further processed by passing through Hitrap DEAE Sepharose F.F. column and the resulting antibody was analyzed to determine the level of purity using size exclusion chromatography (Superdex 200 5/150 GL, G.E. Healthcare).

Example 9 Humanization and Sequence Analysis, Antibody Activity Characterization Humanization and Sequence Analysis:

The sequences of the variable regions of the murine SNGmB1 antibody were used to identify the germline sequences with highest homology to the murine framework and computer-modeling was used to design humanized variants. SNGmB1 was humanized using the light chain V1 with straight CDR graft into VK1|5-2 acceptor framework with V4, P44, L46, S49, S64 back-mutations (SEQ ID NO: 24 and SEQ ID NO: 25, amino acid and nucleotide). SNGmB1 was also humanized using the light chain V2, with V4, L46, S49, S64 back-mutations (SEQ ID NO: 26 and SEQ ID NO: 27, amino acid and nucleotide). SNGmB1 was also humanized using the light chain V3, with V4, P44, L46, S49 back-mutations (SEQ ID NO: 28 and SEQ ID NO: 29). SNGmB1 was humanized using the heavy chain V1 with CDR graft with murine residues at T28A into VH1|1-46 acceptor framework (SEQ ID NO: 32 and SEQ ID NO: 33). SNGmB1 was also humanized using the heavy chain V2 with V1 with additional L81M mutation (SEQ ID NO: 30 and SEQ ID NO: 31). The designed variants were synthesized and cloned into pTT5 expression vector with human IgG1 Fc constant domain and expressed in 293E6 cells.

Characterization of Antibody Activity:

The humanized antibodies were purified and characterized using ELISA and Biacore for binding analysis. The sequence components of the humanized antibody are shown in Table 5.

TABLE 5

Antibody list:

| Antibody Type | Antibody Name | Sequence descriptions of the heavy and the light chains | SEQ ID Nos |
|---|---|---|---|
| Mouse antibody | SNGmB1 | SNGmB1 light chain V region + Mu Kc (Amino Acid) | 16 |
| | | SNGmB1 light chain V region + Mu Kc (Nucleotide) | 17 |
| | | SNGmB1 heavy chain V region + Mu IgG2b C (Amino Acid) | 18 |
| | | SNGmB1 heavy chain V region + Mu IgG2b C (Nucleotide) | 19 |
| Chimeric antibody | SNGhB1 | SNGmB1 light chain V region + Hu κC (Amino Acid) | 20 |
| | | SNGmB1 light chain V region + Hu κC (Nucleotide) | 21 |
| | | SNGmB1 heavy chain V region + Hu IgG1 C (Amino Acid) | 22 |
| | | SNGmB1 heavy chain V region + Hu IgG1 C (Nucleotide) | 23 |
| Humanized antibody | SNGHZD (C1L + C5H) | humanized SNGmB1 light chain V region V4, P44, L46, S49, S64 + Hu κC (Amino Acid) | 24 |
| | | humanized SNGmB1 light chain V region V4, P44, L46, S49, S64 + Hu κC (Nucleotide) | 25 |
| | | humanized SNGmB1 heavy chain V region T28, L81 + Hu IgG1 C (Amino Acid) | 30 |
| | | humanized SNGmB1 heavy chain V region T28, L81 + Hu IgG1 C (Nucleotide) | 31 |
| Humanized antibody | SNGHZD (C2L + C6H) | humanized SNGmB1 light chain V region V4, L46, S49, S64 + Hu κC (Amino Acid) | 26 |
| | | humanized SNGmB1 light chain V region V4, L46, S49, S64 + Hu κC (Nucleotide) | 27 |
| | | humanized SNGmB1 heavy chain V region T28 + Hu IgG1 C (Amino Acid) | 32 |
| | | humanized SNGmB1 heavy chain V region T28 + Hu IgG1 C (Nucleotide) | 33 |
| Humanized antibody | SNGHZD (C3L + C6H) | humanized SNGmB1 light chain V region V4, P44, L46, S49 + Hu κC (Amino Acid) | 28 |
| | | humanized SNGmB1 light chain V region V4, P44, L46, S49 + Hu κC (Nucleotide) | 29 |
| | | humanized SNGmB1 heavy chain V region T28 + Hu IgG1 C (Amino Acid) | 32 |
| | | humanized SNGmB1 heavy chain V region T28 + Hu IgG1 C (Nucleotide) | 33 |
| Humanized antibody | SNGHZD (C3L + C5H) | humanized SNGmB1 light chain V region V4, P44, L46, S49 + Hu κC (Amino Acid) | 28 |
| | | humanized SNGmB1 light chain V region V4, P44, L46, S49 + Hu κC (Nucleotide) | 29 |

TABLE 5-continued

Antibody list:

| Antibody Type | Antibody Name | Sequence descriptions of the heavy and the light chains | SEQ ID Nos |
|---|---|---|---|
| | | humanized SNGmB1 heavy chain V region T28, L81 + Hu IgG1 C (Amino Acid) | 30 |
| | | humanized SNGmB1 heavy chain V region T28, L81 + Hu IgG1 C (Nucleotide) | 31 |
| Humanized antibody | SNGHZD (C1L + C6H) | humanized SNGmB1 light chain V region V4, P44, L46, S49, S64 + Hu κC (Amino Acid) | 24 |
| | | humanized SNGmB1 light chain V region V4, P44, L46, S49, S64 + Hu κC (Nu) | 25 |
| | | humanized SNGmB1 heavy chain V region T28 + Hu IgG1 C (Amino Acid) | 32 |
| | | humanized SNGmB1 heavy chain V region T28 + Hu IgG1 C (Nucleotide) | 33 |
| Humanized antibody | SNGHZD (C2L + C5H) | humanized SNGmB1 light chain V region V4, L46, S49, S64 + Hu κC (Amino Acid) | 26 |
| | | humanized SNGmB1 light chain V region V4, L46, S49, S64 + Hu κC (Nucleotide) | 27 |
| | | humanized SNGmB1 heavy chain V region T28, L81 + Hu IgG1 C (Amino Acid) | 30 |
| | | humanized SNGmB1 heavy chain V region T28, L81 + Hu IgG1 C (Nucleotide) | 31 |

Figure 10A:
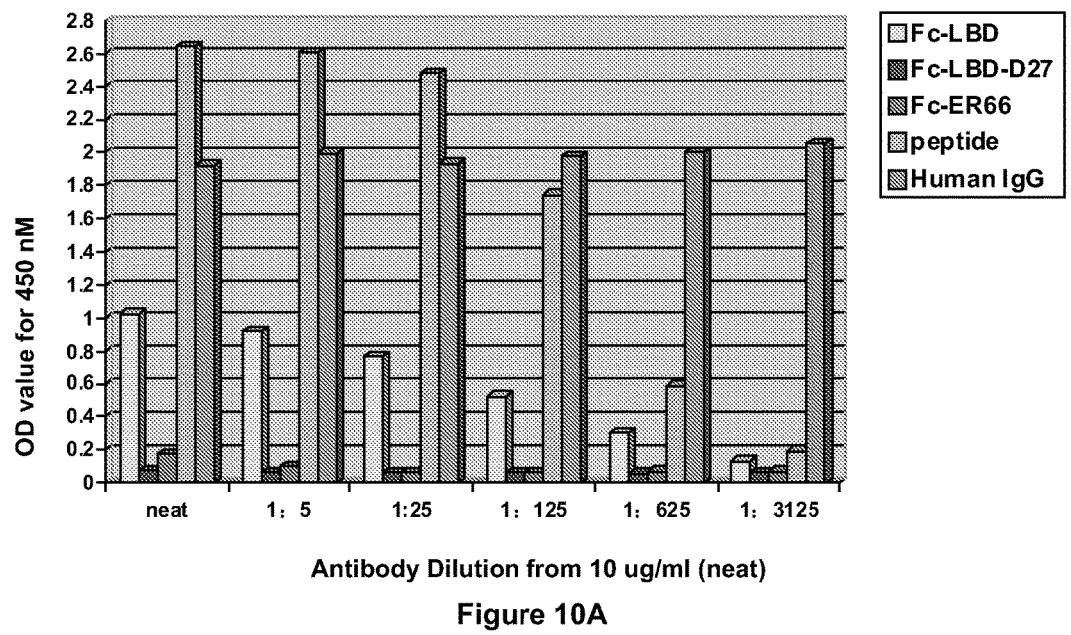
FIG. 10A shows the binding of humanized antibody SNGHZD (C1L+C6H) to ER-α36.
Figure 10B:
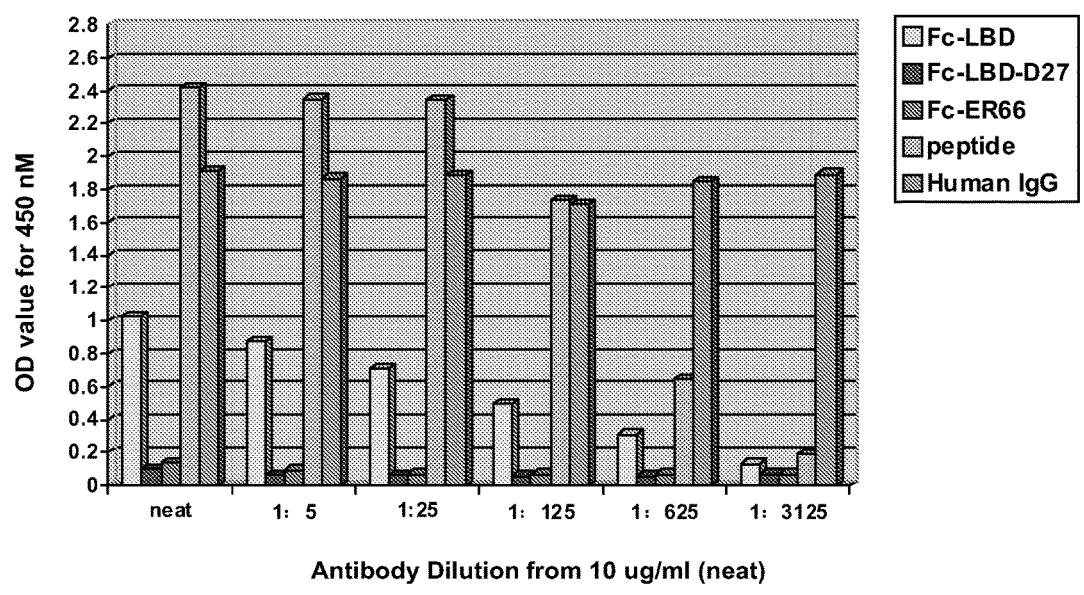
FIG. 10B shows the binding of humanized antibody SNGHZD (C2L+C5H). "Fc-LBD", "Fc-LBD-D27", "Fc-ER66", "peptide" and "Human IgG" represent the same agents as defined in the description for FIG. 3.

The humanized antibodies were tested for their binding affinity to ER-α36. Results were shown in FIGS. 10A-B and Table 6.

TABLE 6

Binding affinity of chimeric and humanized antibodies to human ER-α36

| Sample(Antibody) | Ka(1/Ms) | Kd(1/s) | KD(M) |
|---|---|---|---|
| SNGmB1-20110709(IgG2b) | 2.12e6 | 1.29e−4 | 6.06e−11 |
| SNGmB1-20111117(IgG2b) | 1.76e6 | 3.19e−4 | 1.82e−10 |
| SNGhB1(20111118) | 1.74e6 | 2.83e−4 | 1.63e−10 |
| SNGHZD (C1L + C5H) | 7.44e5 | 1.22e−4 | 1.64e−10 |
| SNGHZD (C2L + C6H) | 1.28e6 | 3.98e−4 | 3.1e−10 |
| SNGHZD (C3L + C6H) | 1.33e6 | 3.6e−4 | 2.71e−10 |
| SNGHZD (C3L + C5H) | 3.54e6 | 3.56e−4 | 1e−10 |
| SNGHZD (C1L + C6H) | 2.89e6 | 3.02e−4 | 1.05e−10 |
| SNGHZD (C2L + C5H) | 3.46e6 | 4.88−4 | 1.3e−10 |

Competition ELISA

The hybridoma derived SNGmB1, chimeric SNGmB1, and humanized SNGmB1 were tested for their ability to compete with hybridoma derived SNGmB1 or 104c3F8 antibody (an ERα36 antibody having a different sequence from SNGmB1) for binding to ER-α36, using ELISA competition assay.

Clear polystyrene plates (Nunc) were coated with 1 μg/ml hybridoma derived SNGmB1, chimeric SNGmB1 or humanized SNGmB1 in PBS, and the plates were incubated overnight at 4° C., then washed once on an automatic plate washer. The antigen (biotinylated GV27 peptide) was added along with different amount of the competing mouse antibody, the ELISA plates were then allowed to incubate for equilibrium before wash. Streptavidin-HRP (Sigma, S2438, 1:5000) and TMB substrate (Biopanda, China) were added and OD450 was measured on a plate reader. IgG were tested in parallel as control antibody.

Figure 10C:
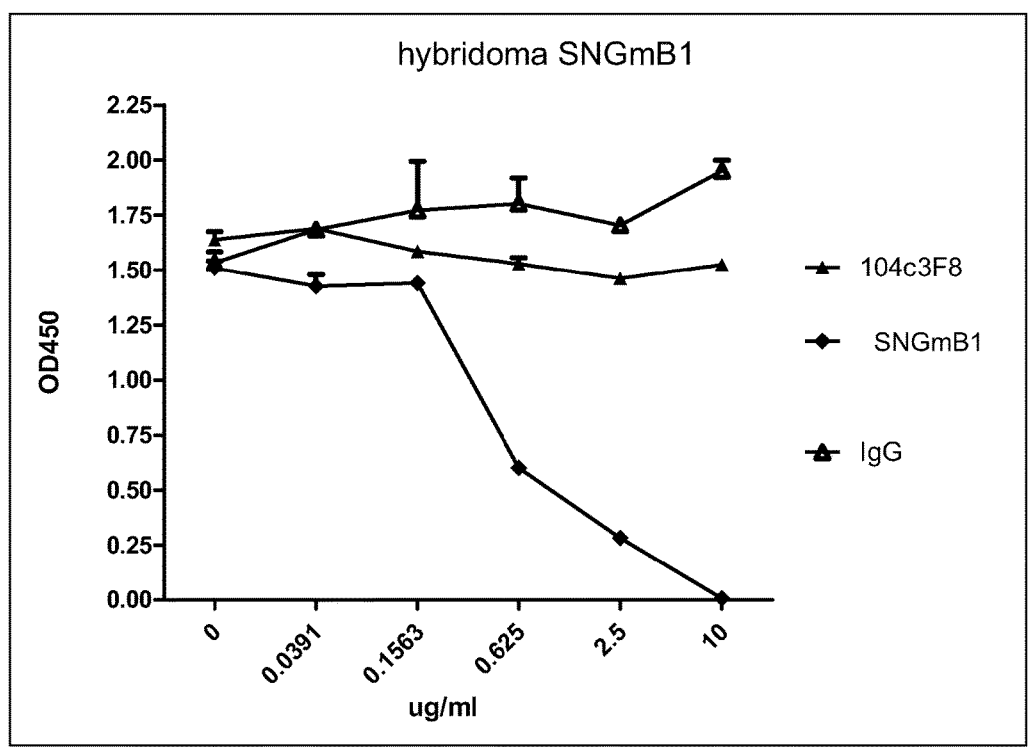
FIG. 10C to FIG. 10D show that hybridoma derived mouse SNGmB1 (C), chimeric SNGhB1 (D), and humanized SNGHZD respectively compete against SNGmB1 antibody for binding to ER-α36, as detected in an ELISA assay. Plates were coated with SNGmB1, SNGhB1 and SNGHZD respectively, followed by addition of the biotinylated GV27 peptide and the competing antibody (i.e., antibody 104c3F8 which is an anti-ERa-36 antibody binding to a different epitope, antibody SNGmB1, or a control IgG).
Figure 10D:
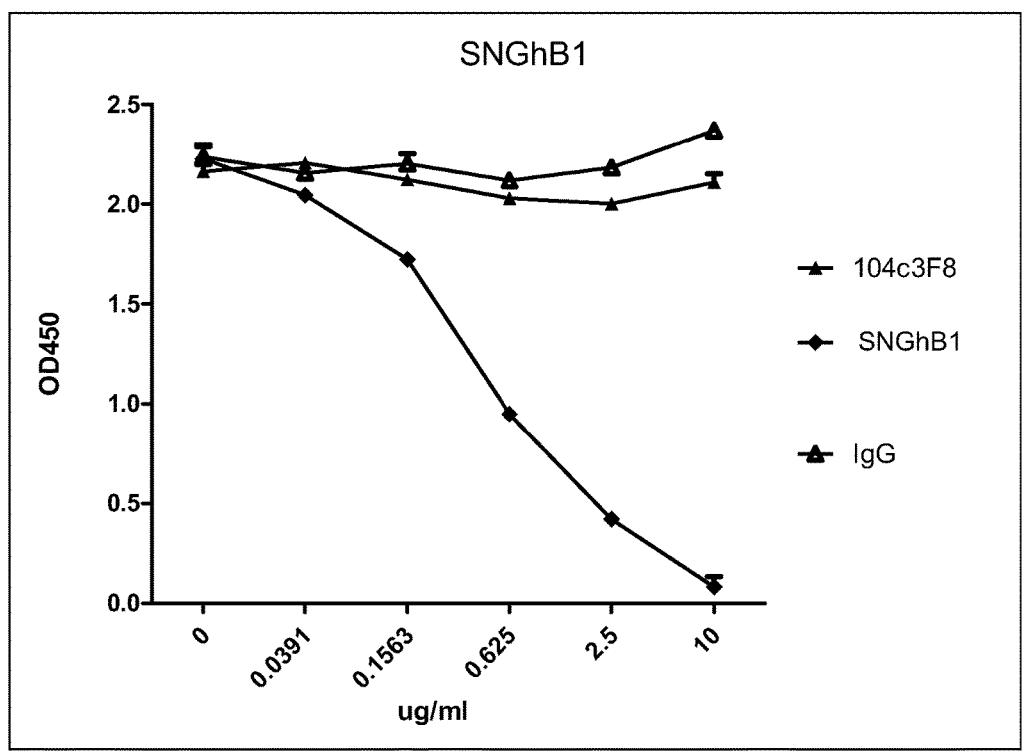
Figure 10E:
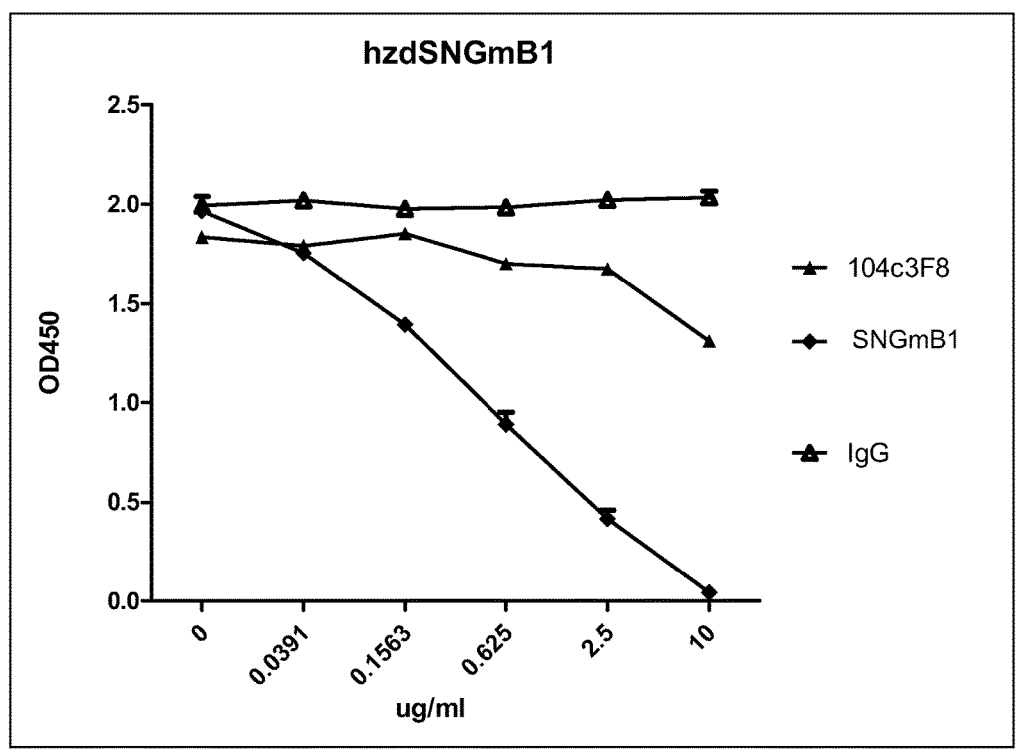
FIG. 10 shows the binding of the anti-ERa-36 antibodies to ER-α36.
FIG. 10F illustrates that different humanized variants of SNGmB1 compete against SNGmB1 antibody for binding to ER-α36. HZD-B1 represents for a humanized variant of SNGmB1, HBD-F8 represents humanized 104c3F8, HBD-B1 represents hybridoma produced SNGmB1, Mouse IgG represents a negative control antibody.

Results were shown in FIGS. 10C-10E. All of the three tested antibodies competed with SNGmB1 for GV27 peptide binding in a dose-dependent manner, but none of them showed obvious competition with antibody 104c3F8 for binding to the GV27 peptide. Based on complete set of data, there were different binding sites on the GV27 peptide, and antibodies derived from SNGmB1 bound to a site which was different from that bound by the 104c3F8 antibody.

Figure 10F:
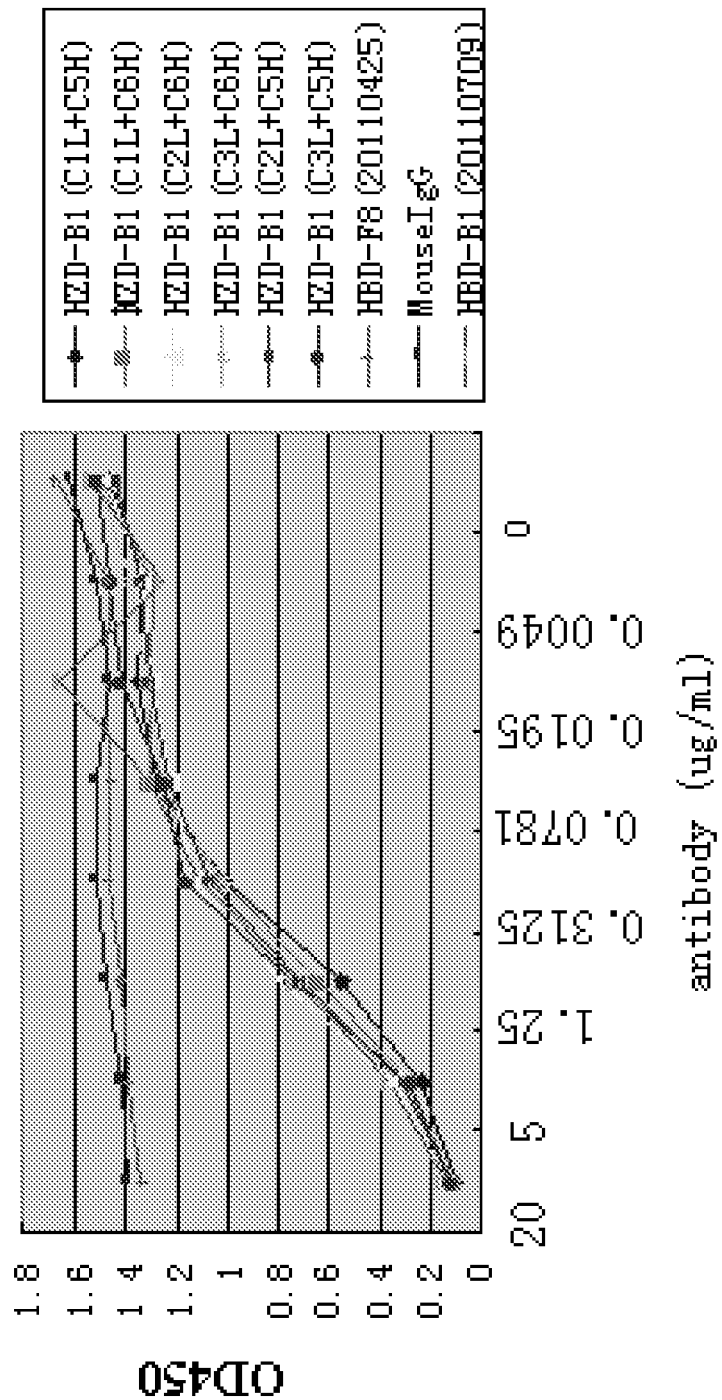

The different humanized antibodies were tested using the competition ELISA assay as described. Briefly, 1 μg/ml of SNGmB1 was coated on a plate, and antigen (biotinylated GV27 peptide) was added along with different amount of the competing antibody (i.e. the different humanized antibodies shown in Table 6). Mouse IgG and HBD-F8 (i.e. humanized 104C3F8) were tested in parallel as negative controls, and HBD-B1 was tested in parallel as a positive control (hybridoma produced SNGmB1). Results were shown in FIG. 10F. All humanized variants showed dose dependent competition to SNGmB1 antibody.

Example 10 Diagnostic Use: IHC Analysis of Human Samples

Immunohistochemistry (IHC) assay was used to evaluate the ability of utilizing a specific antibody like SNGmB1 to better detect the presence of ER-α36 in human tissue samples. 4 μm thick paraffin tissue blocks of breast cancer patients were de-paraffinized by immersing in the xylene for twenty minutes twice, followed by rehydrating sequentially in 99%, 90%, 85%, 75%, 50% ethanol for 5 minutes each. The tissue sections were then washed three times with PBS. Antigen retrieval was then performed by heating in 95° C. citrate (pH 6.0) buffer for 15 minutes in microwave. Once cooled to room temperature, the sections were then washed with PBS three times, and incubated with 3% hydrogen peroxide for 20 minutes at room temperature, followed by washing with PBS. The non-specific binding of antibody were then blocked by incubating with 10% normal goat serum for 30 minutes, followed with incubating with primary antibody overnight at 4° C. in a humid chamber. Upon washing with PBS five times, pre-diluted secondary antibody (ZSGB-Bio, Cat# PV-6000) was added and incubated for 20 minutes at room temperature. The sections were then washed with PBS and incubated with DAB solution for 2-5 minutes, followed by rinsing in distilled water for 5-10 minutes. The sections were then counter-stained in hematoxylin (ZSGB-BIO, Cat# ZLI-9609), followed by rinsing sequentially in 50%, 75%, 85%, 90% and 99% A ethanol to dehydrate. The sections were then cleared in xylene and sealed with neutral balsam before evaluated with microscope.

As shown in FIG. 11, the SNGmB1 antibody detected both membrane bound and cytoplasmic expression of ER-α36 protein in human tumor tissues (FIG. 11).

Figure 12:
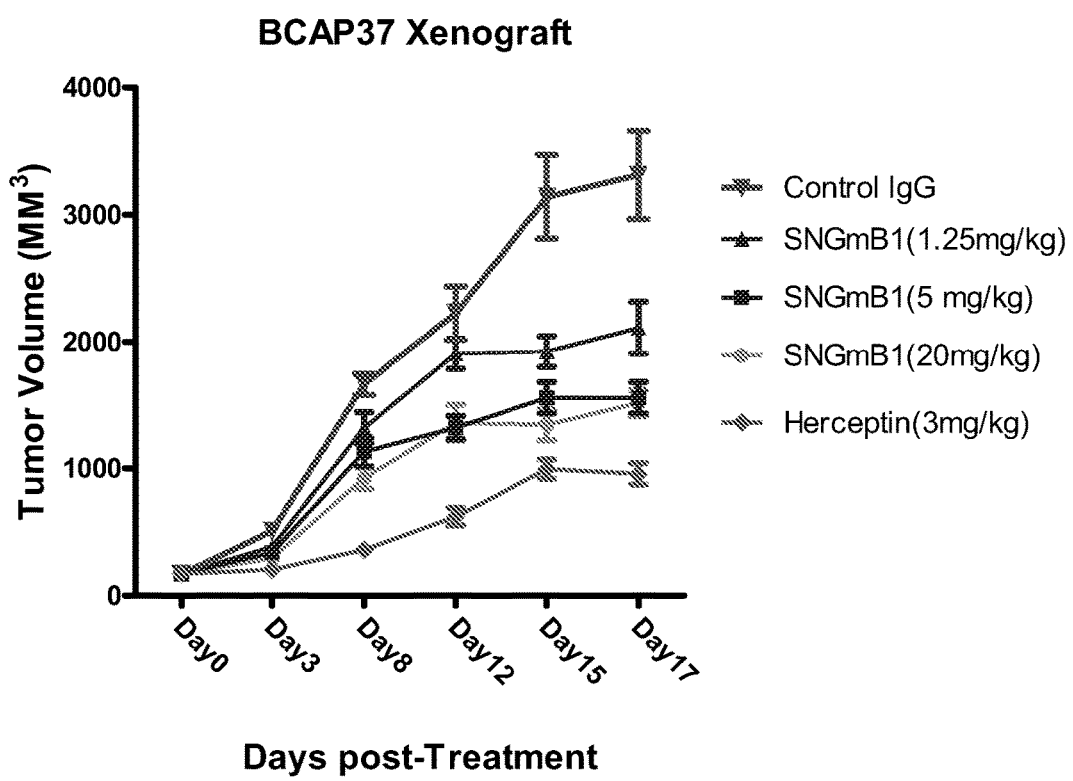
FIG. 12 shows that SNGmB1 inhibited tumor cell growth in a does-dependent manner in BCAP37 Xenograft mouse model.

Example 11 Ability of Anti-ER-α36 Antibody in Inhibiting Human Tumor Cell Growth The ability of anti-ER-α36 antibody in inhibiting human tumor cell growth in Xenograft model was assessed using BCAP37 breast cancer model. BCAP37 was developed from a patient with invasive ductal breast carcinoma and was shown to express ER-α36 and HER2 by western blot. The cells were implanted into NOD-SCID mice. When the tumor grown to 80-120 mm3 size, the mice were randomized into groups of 10 mice and been treated either with mouse IgG2b or SNGmB1 antibody or Herceptin, at a does of 1.25, 5 and 20 mg/kg for SNGmB1, or 3 mg/kg for Herceptin. After 17 days of treatment, the tumors were excised, and both tumor weight and volume were measured. As shown in FIG. 12, SNGmB1 antibody was found to be able to inhibit tumor growth in a dose-dependent manner, similar to herceptin. There was significant difference between the tumor volume from the control IgG2b treated groups and SNGmB1 antibody treated groups.

Example 12 Synthesis of the Antibody-Drug Conjugate (ADC) of Ab-mc-vc-PAB-MMAE Formula(VII)

1. Synthesis of the Antibody-Drug Conjugate (ADC) of Ab-Mc-Vc-PAB-MMAE Formula (VII)

140 mg of antibody SNGmB1(Ab) is taken and dissolved in PBS (Corning), adjusting the concentration of the solution to 10 mg/ml. TCEP (Thermo Scientific) is added into the antibody solution in the molar ratio, TCEP/Ab=3. A tube with the above solution is kept at 37° C. for 2 hrs. Small molecules (such as TCEP and TCEP oxide) are removed through a equilibrated PD-10 column (GE) in PBS. Monitoring Ab concentration and free thiol in DTNB. When the free thiol/Ab>4, 1/10 (v/v) dimethyl acetamide (DMA) (Honeywell) is added to the Ab solution. 10 mM MMAE (i.e. drug) in DMA is added into the Ab solution in molar ratio, and the ratio of the drug to the Ab is reached to 4.5. The solution is kept on room temperature for 4 hrs and the reaction is monitored through HIC-HPLC (Agilent). After the reaction is finished, the product of ADC is purified with Amicon centrifugal filter unit, and through 0.2 um filter, washed 6 times in 10 volume PBS, the final product is obtained. The ADC is stored at 4° C.

Figure 13:
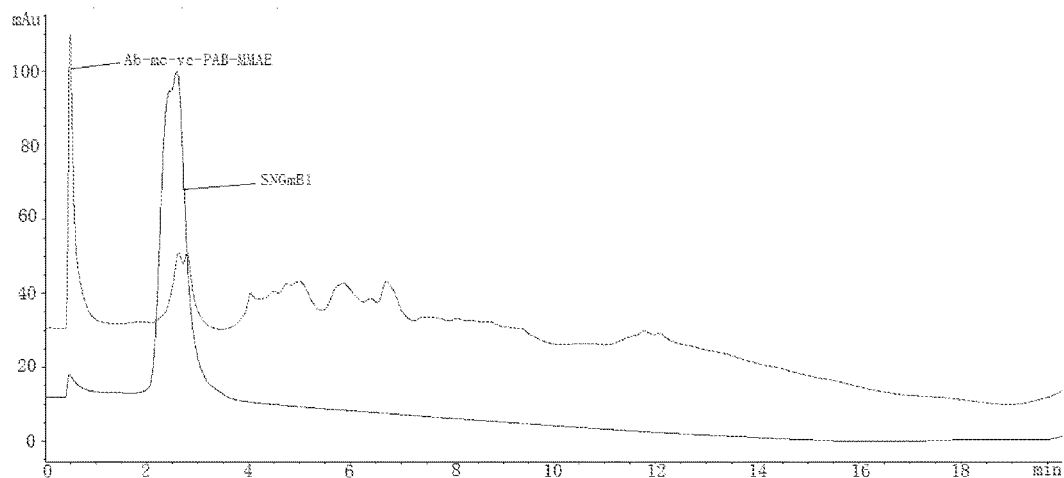
FIG. 13 shows HIC-HPLC chromatograms of the Ab-mc-vc-PAB-MMAE as formula (VII) and SNGmB1.

2. Analysis of the ADC
2.1. HIC-HPLC Procedure
column: #14947, TSK gel Butyl-NPR, 4.6 mm I.D.×3.5 cm, 2.5 um (Tosoh Bioscience), column temperature, 30° C.
Flow rate: 1 ml/min
Detection: UV280 and UV252. Buffer A: 1.5 M Ammonium Sulfate;
Buffer B: 25 mM Sodium phosphate, pH7.0, 25% Isopropanol, 20 min, 0%-90%; 1 min, 90%-95%; 4 min, 95%; 1 min, 95%-0%. 20 ul sample for analysis depending on the ADC concentration
2.2 SEC-HPLC Procedure
Column: #08541, G3000SWxl, 7.8 mm I.D.×30 cm, 5 um (Tosoh Bioscience), column temperature, room temperature.
Flow rate: 0.4 ml/min
Detection: UV280.
Buffer: 100 mM Sodium phosphate, pH 7.0, 100 mM Sodium Chloride, 15% Isopropanol, 60 min.
20 ul sample for analysis depending on the ADC concentration. Nanodrop procedure and DAR calculation
ul volume for measurement; 1x PBS as blank; Record the absorption of 280 nm.
3. Results
3.1 HIC-HPLC
Seen from FIG. 13, the chromatography with little peaks demonstrates un-conjugate antibody of the present invention. The chromatography with more peaks demonstrates Ab-mc-vc-PAB-MMAE. Both samples were analyzed under identical HIC-HPLC condition. Ab-mc-vc-PAB-MMAE shows multiple peaks under the standard HPLC condition, which suggests the heterogeneous population of antibody itself.

Figure 14A:
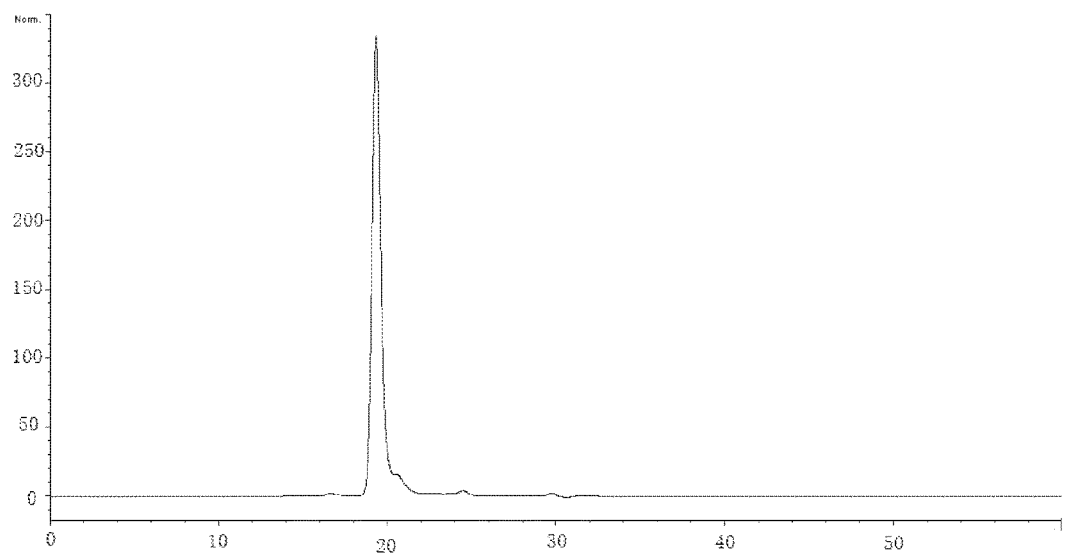
FIG. 14a shows SEC-HPLC chromatograms of SNGmB1.
Figure 14B:
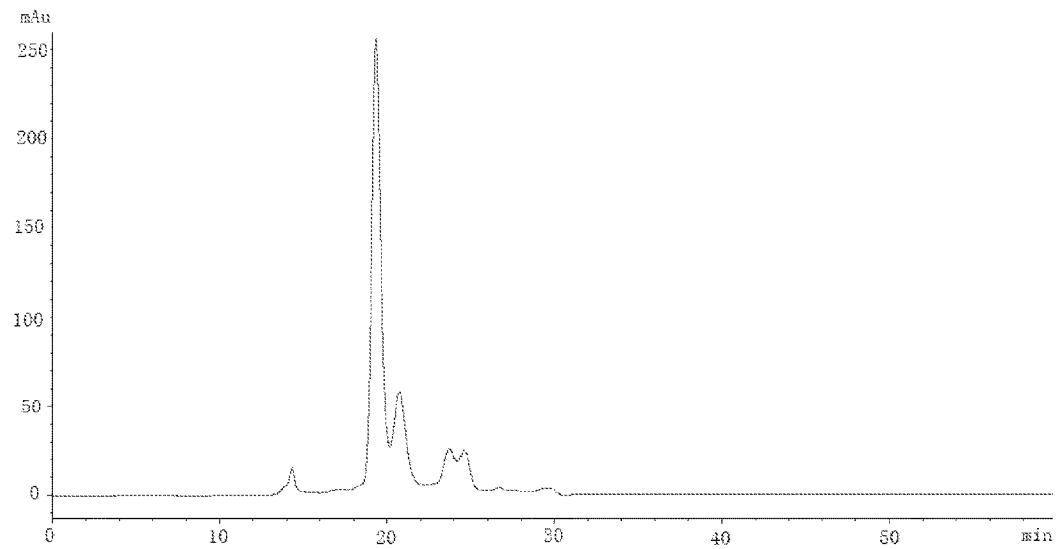
FIG. 14b shows SEC-HPLC chromatograms of the Ab-mc-vc-PAB-MMAE as formula(VII)

Based on distribution of peaks, the average DAR=3.97, with 7.89% unconjugated antibody.
3.2 SEC-HPLC
Seen from FIG. 14a, it is demonstrated un-conjugated antibody i.e. SNGmB1 of the present invention. Seen from FIG. 14b, it is demonstrated the ADC of Ab-mc-vc-PAB-MMAE. The result indicates that lower mass weight (MW) species are formed during the conjugation process, which may suggests that the antibody was reduced and formed lower MW species instead of forming an intact IgG, also forming some HMW species by inter-IgG disulfide bonds.

Example 13 Synthesis of the Antibody-Drug Conjugate (ADC) of Ab-mc-MMAF Formula (VIII)

1. Synthesis of ADC Ab-mc-MMAF Formula (VIII)
140 mg Ab is taken and dissolved in PBS(Corning), adjusting the concentration of the solution to 10 mg/ml. TCEP (Thermo Scientific) is added into the Ab solution in molar ratio, TCEP/Ab=3. A tube with the above solution is kept at 37° C. for 2 hrs. Small molecules are removed through equilibrated PD-10 column (GE) in PBS. Monitoring Ab concentration and free thio in DTNB, when the free thiol/Ab>4, 1/10 (v/v) dimethyl acetamide (DMA) (Honeywell) is added to the Ab solution. 10 mM MMAF i.e. drug in DMA is added into the Ab solution in molar ratio, and the ratio of the drug to Ab is reached to 4.5. The solution is kept on room temperature for 4 hrs and the reaction is monitored through HIC-HPLC (Agilent). After the reaction is finished, the product of ADC is purified with Amicon centrifugal filter unit, and washed 6 times in 10 volume PBS, the final product is obtained. The ADC is stored at 4° C. after being filtered through 0.2 um filter.

2. Analysis of the Conjugate
2.1 HIC-HPLC Procedure
column: #14947, TSK gel Butyl-NPR, 4.6 mm I.D.×3.5 cm, 2.5 um (Tosoh Bioscience), column temperature, 30° C.
Flow rate: 1 ml/min
Detection: UV280 and UV252.
Buffer A: 1.5 M Ammonium Sulfate;
Buffer B: 25 mM Sodium phosphate, pH7.0, 25% Isopropanol,
20 min, 0%-90%; 1 min, 90%-95%; 4 min, 95%; 1 min, 95%-0%. 20 ul sample for analysis depending on the ADC concentration.
2.2 SEC-HPLC procedure
Column: #08541, G3000SWx1, 7.8 mm I.D.×30 cm, 5 um (Tosoh Bioscience), column temperature, room temperature.
Flow rate: 0.4 ml/min
Detection: UV280.

Buffer: 100 mM Sodium phosphate, pH 7.0, 100 mM Sodium Chloride, 15% Isopropanol, 60 min.

20 ul sample for analysis depending on the ADC concentration.

Nanodrop procedure and DAR calculation 2.5 ul volume for measurement; 1×PBS as blank Record the absorption of 280 nm.

3. Results 3.1 HIC-HPLC

Figure 15:
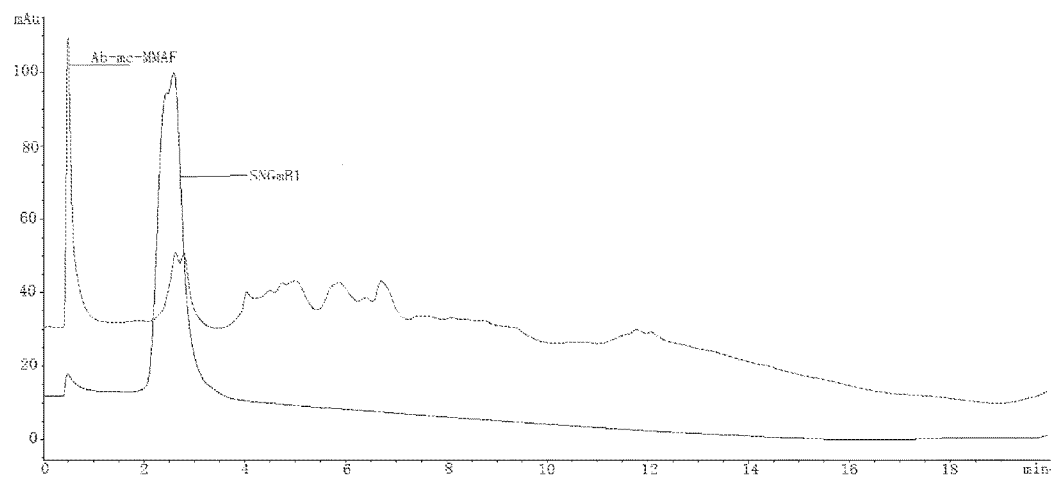
FIG. 15 shows HIC-HPLC chromatograms of the Ab-mc-MMAF as formula(VII)) and SNGmB1.

Seen from FIG. 15, the chromatography with little peaks demonstrates un-conjugate antibody i.e. SNGmB1 of the present invention. The chromatography with more peaks demonstrates Ab-mc-MMAF. Both samples were analyzed under identical HIC-HPLC condition. Ab-mc-MMAF shows multiple peaks under the standard HPLC condition, which suggests the heterogeneous population of antibody itself.

Based on distribution of peaks, the average DAR=3.97, with 7.89% unconjugated antibody.

3.2 SEC-HPLC

Figure 16:
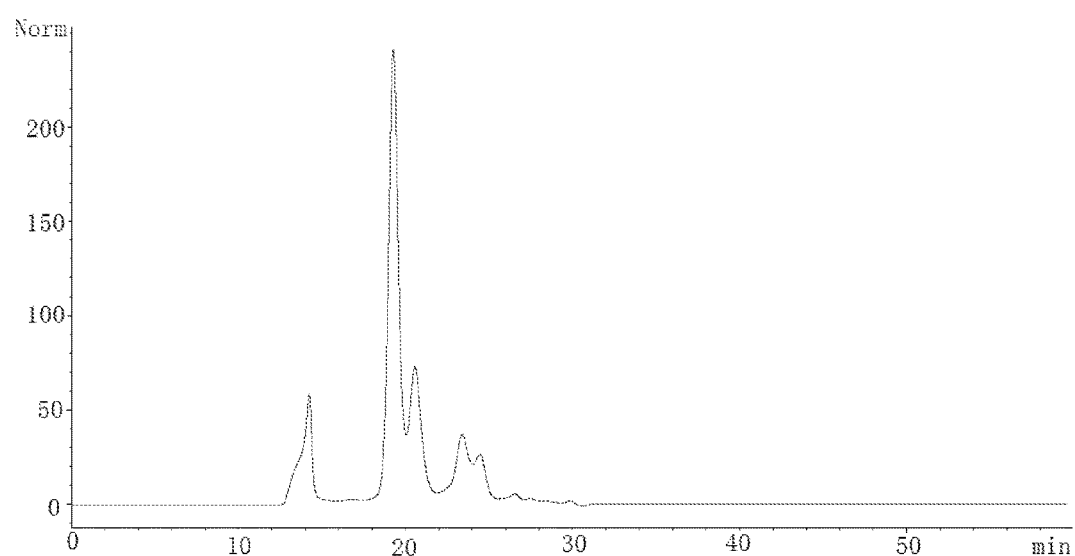
FIG. 16 shows SEC-HPLC chromatograms of the Ab-mc-MMAF as formula(VII)).

Seen from FIG. 16, it is demonstrated the ADC of Ab-mc-MMAF. The result indicates that lower mass weight (MW) species were formed during the conjugation process, which may suggest that antibody is reduced and formed lower MW species instead of forming an intact IgG. Also, there is significant amount of height mass weight (HMW).

Therefore, the ADCs of Ab-mc-vc-PAB-MMAE and Ab-mc-MMAF are prepared. The purity of the ADC Ab-mc-vc-PAB-MMAE is above 98.0%. The purity of ADC Ab-mc-MMAF is above 98.0%. The whole reaction can be monitored by HPLC.

Example 14 Synthesis of the Antibody-Drug Conjugate (ADC) of Ab-SMCC-DM1 Formula (E)

Synthesis of the Ab-SMCC-DM1

100 mg Ab is taken and dissolved in PBS(Corning), adjusting the concentration of the solution to 10 mg/ml. The buffer of PBS is exchanged to conjugation buffer (50 mM Sodium phosphate, pH=6.5). DMA1/10(v/v) is added to the solution, and the molar ratio of DM1 i.e. drug to the antibody is equal to 7.5. The reaction is kept at room temperature for 2 hrs. The reaction is monitored in HIC-HPLC. After the reaction is finished, the product of ADC is purified with Amicon centrifugal filter unit, and washed 6 times in 10 volume PBS, the final product is obtained. The ADC is stored at 4° C. after being filtered through 0.2 um filter.

Analytical Method Procedures 2.1 HIC-HPLC Procedure column: #14947, TSK gel Butyl-NPR, 4.6 mm I.D.×3.5 cm, 2.5 um (Tosoh Bioscience), column temperature, 30° C.

flow rate: 1 ml/min.

Detection: UV280 and UV252.

Buffer A: 1.5 M Ammonium Sulfate; Buffer B: 25 mM Sodium phosphate, pH7.0. 25% Isopropanol, 20 min, 0%-90%; 1 min, 90%-95%; 4 min, 95%; 1 min, 95%-0%.

μl sample for analysis depending on the ADC concentration.

2.2 SEC-HPLC Procedure

Column: #08541, G3000SWxl, 7.8 mm I.D.×30 cm, 5 um (Tosoh Bioscience). Column temperature: room temperature.

Flow rate: 0.4 ml/min.

Detection: UV280. Buffer: 100 mM Sodium phosphate, pH 7.0, 100 mM Sodium Chloride, 15% Isopropanol, 60 min.

5-100 ul sample for analysis depending on the ADC concentration.

2.3 Nanodrop Procedure and DAR Calculation 2.5 ul volume for measurement

1×PBS as blank

Record the absorption of 280 nm.

2.4 Entotoxin detection procedure

Dilute the sample with Endotoxin-free water to the desired test range (50-100 fold), following the Endosafe PTS instrument instruction to add sample to the cartridge. Print out the endotoxin reading.

Conclusion 3.1 HIC-HPLC

Figure 17:
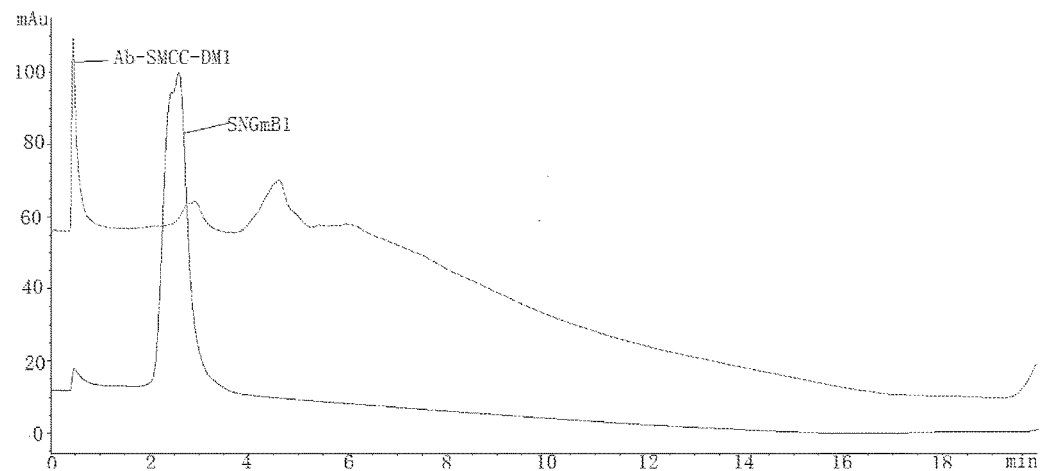
FIG. 17 shows HIC-HPLC chrotomagrams of the Ab-SMCC-DM1 as formula(IX) and SNGmB1.

In the FIG. 17, the chromatography with little peaks demonstrates un-conjugate antibody of the present invention. The chromatography with more peaks demonstrates Ab-SMCC-DM1. Both samples were analyzed under identical HIC-HPLC condition. Ab-SMCC-DM1 shows multiple peaks under the standard HPLC condition, which suggests the heterogeneous population of antibody itself.

Based on UV absorption, the average ration of drug to the antibody is equal to 2.86., with 11.05% unconjugated antibody. The ratio of unconjugated antibody was lower than 10%, it was increased during the storage at 4° C.

3.2 SEC-HPLC

Figure 18:
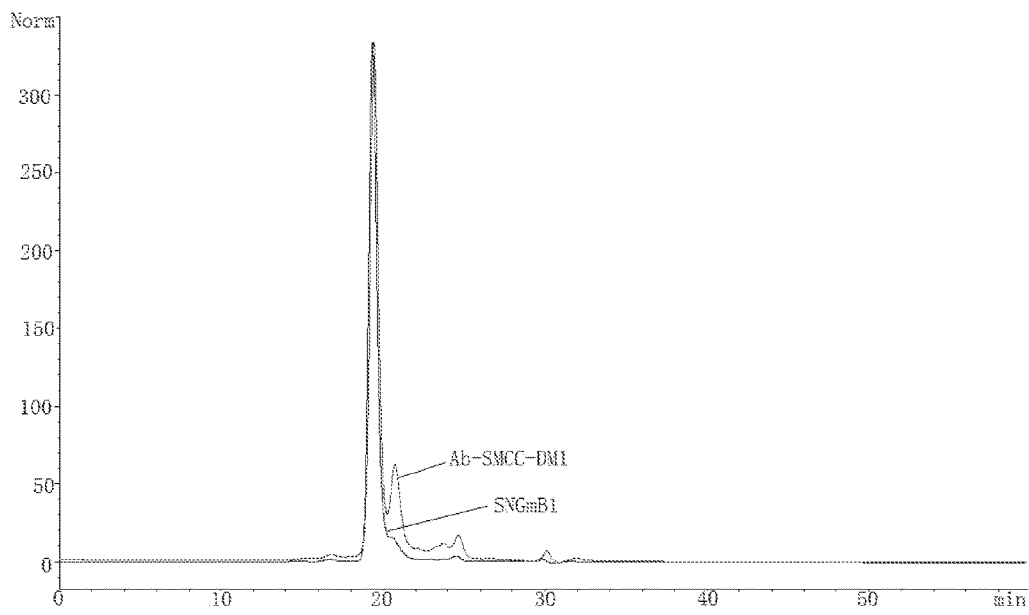
FIG. 18 shows SEC-HPLC chrotomagrams of Ab-SMCC-DM1 as formula(IX) and SNGmB1.

Seen from FIG. 18, the chromatography with more peaks is ADC, and the chromatography with little peaks is the un-conjugate antibody. Compared with Ab-MB-vc-PAB-MMAE, Ab-SMCC-DM1 contains far less low mass weight (MW) species, which confirm that the low MW species in MMAE conjugate were generated from the reduction step.

Example 15 Synthesis of the Antibody-Drug Conjugate(ADC) of Ab-SPDB-DM4 Formula (X)

1. Synthesis of the Antibody-Drug Conjugate 100 mg Ab is taken and dissolved in PBS(Corning), adjusting the concentration of the solution to 10 mg/ml. The buffer of PBS is exchanged to conjugation buffer (50 mM Sodium phosphate, pH=6.5). DMA1/10(v/v) is added to the solution, and the molar ratio of the antibody to DM4, i.e. drug is equal to 7.5. The reaction is kept at room temperature for 2 hrs. The reaction is monitored in HIC-HPLC. After the reaction is finished, the product of ADC is purified with Amicon centrifugal filter unit, and washed 6 times in 10 volume PBS, the final product is obtained. The ADC is stored at 4° C. after being filtered through 0.2 um filter.

2. Analytical Method Procedures 2.1 HIC-HPLC Procedure column: #14947, TSK gel Butyl-NPR, 4.6 mm I.D.×3.5 cm, 2.5 um (Tosoh Bioscience), column temperature, 30° C.

flow rate: 1 ml/min.

Detection: UV280 and UV252.

Buffer A: 1.5 M Ammonium Sulfate; Buffer B: 25 mM Sodium phosphate, pH7.0. 25% Isopropanol, 20 min, 0%-90%; 1 min, 90%-95%; 4 min, 95%; 1 min, 95%-0%.

20 μl sample for analysis depending on the ADC concentration.

2.2 SEC-HPLC Procedure

Column: #08541, G3000SWxl, 7.8 mm I.D.×30 cm, 5 um (Tosoh Bioscience). Column temperature: room temperature.

Flow rate: 0.4 ml/min.

Detection: UV280.

Buffer: 100 mM Sodium phosphate, pH 7.0, 100 mM Sodium Chloride, 15% Isopropanol, 60 min.

20 ul sample for analysis depending on the ADC concentration.

Figure 19:
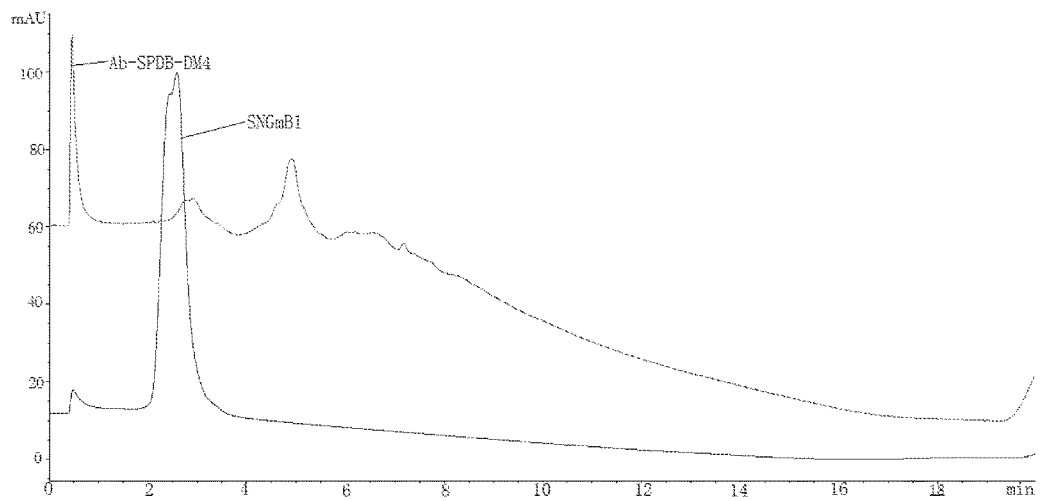
FIG. 19 shows HIC-HPLC chrotomagrams of the Ab-SPDB-DM4 as formula(X) and SNGmB1.

2.3 Nanodrop procedure and DAR calculation
2.5 ul volume for measurement
1×PBS as blank
Record the absorption of 280 nm.
3. Conclusion
3.1 Hic-Hplc In the FIG. 19, the chromatography with little peaks demonstrates unconjugate antibody of the present invention. The chromatography with more peaks demonstrates Ab-SPDB-DM4. Both samples were analyzed under identical HIC-HPLC condition. Ab-SPDB-DM4 shows multiple peaks under the standard HPLC condition, which suggests the heterogeneous population of antibody itself.

Based on UV absorption, the average ration of drug to the antibody is equal to 3.28, with 9.01% unconjugated antibody. The ratio of unconjugated antibody was lower than 10%, it was increased during the storage at 4° C.

3.2 SEC-HPLC

Figure 20:
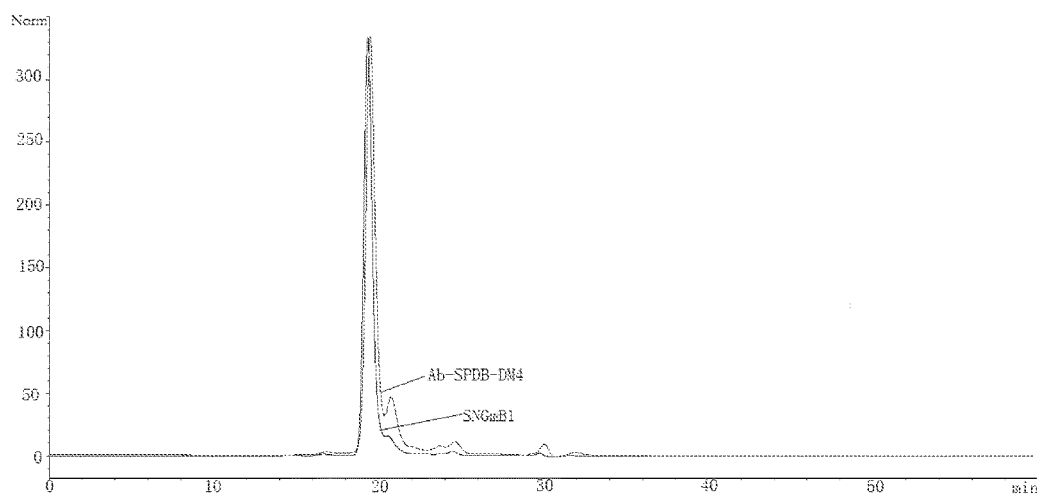
FIG. 20 shows SEC-HPLC chrotomagrams of the Ab-SPDB-DM4 as formula(X).

Seen from FIG. 20, the chromatography with more peaks is ADC, and the chromatography with little peaks is the un-conjugate antibody.

Example 16 Synthesis of the Antibody-Drug Conjugate (ADC) of Ab-MB-Vc-Duocarmycin of Formula (XI)

1. Synthesis of the Antibody-Drug Conjugate 140 mg Ab i.e. SNGmB1 is taken and dissolved in PBS (Corning), adjusting the concentration of the solution to 10 mg/ml. TCEP (Thermo Scientific) is added into the Ab solution in a molar ratio of TCEP/Ab=3. The tube with the above solution is kept at 37° C. for 2 hrs. Excess TCEP is removed through equilibrated PD-10 column (GE) in PBS. Monitoring Ab concentration and free thio in DTNB, when the free thiol/Ab>4, 1/10 (v/v) dimethyl acetamide (DMA, Honeywell) is added to the Ab solution. 10 mM duocarmycin i.e. drug in DMA is added into Ab solution in molar ratio, and the ratio of drug to Ab is reached to 4.5. The solution is kept on room temperature for 4 hrs and the reaction is monitored through HIC-HPLC(Agilent). After the reaction is finished, the product of ADC is purified with Amicon centrifugal filter unit, and washed 6 times in 10 volume PBS, the final product is obtained. The ADC is stored at 4° C. after being filtered through 0.2 um filter.

2. Analytical Method Procedures 2.1 HIC-HPLC Procedure column: #14947, TSK gel Butyl-NPR, 4.6 mm I.D.×3.5 cm, 2.5 um (Tosoh Bioscience), column temperature, 30° C.
Flow rate: 1 ml/min
Detection: UV280 and UV252.
Buffer A: 1.5 M Ammonium Sulfate; Buffer B: 25 mM Sodium phosphate, pH7.0, 25% Isopropanol,
20 min, 0%-90%; 1 min, 90%-95%; 4 min, 95%; 1 min, 95%-0%.
20 ul sample for analysis depending on the ADC concentration.

2.2 SEC-HPLC procedure

Column: #08541, G3000SWxl, 7.8 mm I.D.×30 cm, 5 um (Tosoh Bioscience), column temperature, room temperature.
Flow rate: 0.4 ml/min
Detection: UV280.
Buffer: 100 mM Sodium phosphate, pH 7.0, 100 mM Sodium Chloride, 15% Isopropanol, 60 min.
20 ul sample for analysis depending on the ADC concentration.

Figure 21:
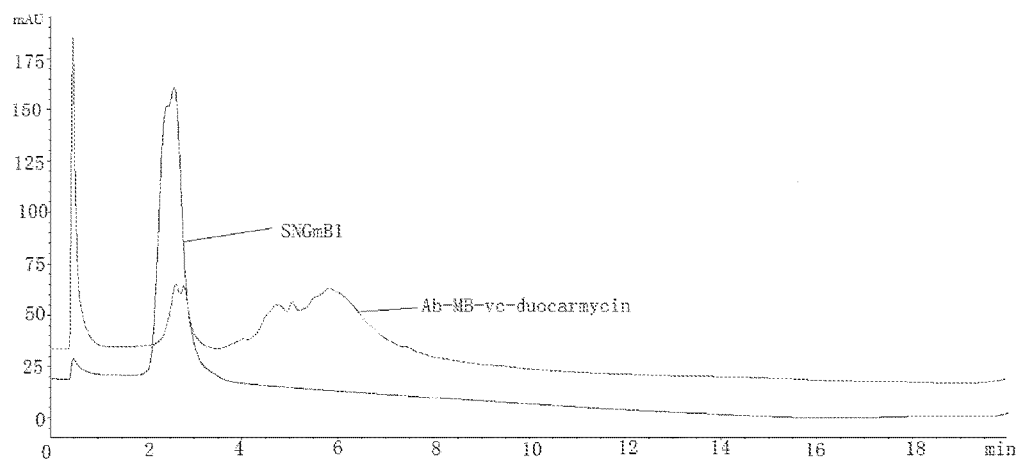
FIG. 21 shows HIC-HPLC chrotomagrams of the MB-VC-duocarmycin as formula(XI) and SNGmB1.

2.3 Nanodrop Procedure and DAR Calculation
2.5 ul volume for measurement
1×PBS as blank
Record the absorption of 280 nm.
3. Conclusion Seen from FIG. 21, the chromatography with more peaks is ADC, and the chromatography with little peaks is the un-conjugate antibody. Both samples were analyzed under identical HIC-HPLC condition. The ADC shows multiple peaks under the standard HPLC condition, which suggests the heterogeneous population of antibody itself.

Based on distribution of peaks, the average DAR=3.04, with 17.6% unconjugated antibody.

Figure 22:
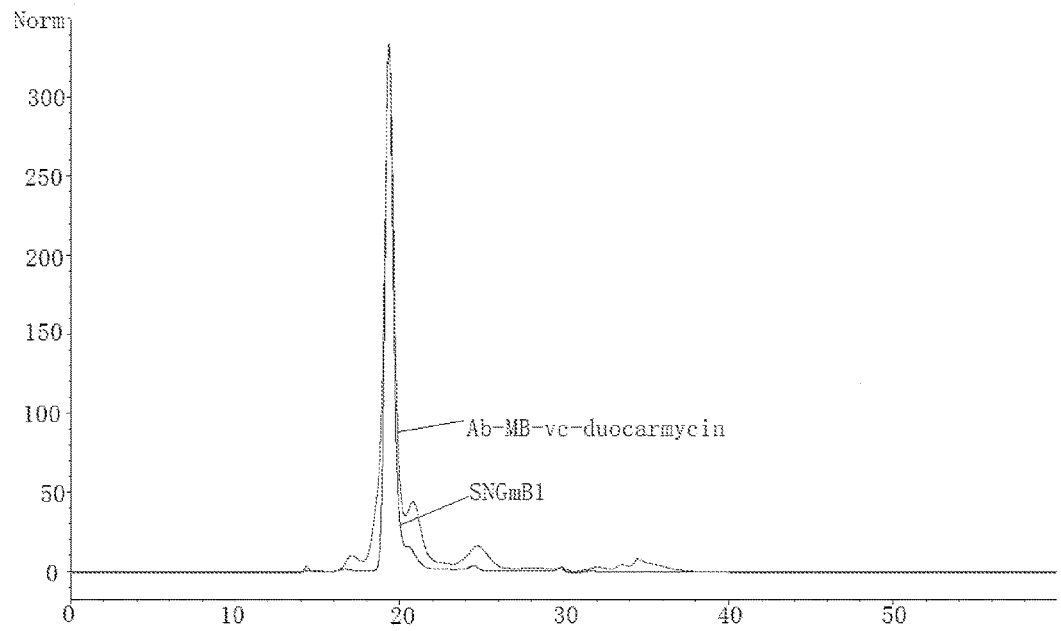
FIG. 22 shows SEC-HPLC chrotomagrams of the MB-VC-duocarmycin as formula(XI).

Seen from FIG. 22, the chromatography with more peaks is ADC, and the chromatography with little peaks is the un-conjugate antibody. The result indicates that lower MW species were formed during the conjugation process, which may suggests that antibody was reduced and formed lower MW species instead of forming a intact IgG.

Example 17 Viability Assay of the Cells Treated with Conjugates

The cells used in this experiment are listed as following table 1.

TABLE 1

| MHCC97H | hepatocellular carcinoma | ER-α 36 |
|---|---|---|
| PLC | hepatocellular carcinoma | ER-α 36+ |
| SUM159 | breast cancer | ER-α 36+ |

Experiment Method

The 1st Day:

Cells of table 1 were taken respectively with 90% confluence and culture medium was removed. 2 mL PBS was added to 60 mm petri dish, and was removed t. 0.5 mL trypsin was added to the petri dish, and kept at 37° C. for 2~3 min. When about 80% cells were suspended through microscope, 1 mL complete medium was added to terminate the reaction. The cells suspension was transferred to 2 mL Ep tube, and centrifugated for 5 minutes at 900 rpm on room temperature. Supernant was absorbed and 1 ml PBS was added to resuspend cells (removing Phenol red and serum hormone). The solution was centrifugated for 5 minutes at 900 rpm on room temperature, and the cells were through 2.5% CS-FBS medium without phenol red and counting. The cells were cultivated on 96-well plates according to the cell volume and growth speed, keeping 2000-3000 cells/well and 90 μL/well. Each ADC was dropped in triple well, and PBS was added around the edge of a well. The plates were Put on incubator with 5% $CO_2$, and kept on 37° C. for 24 hours, The $2^{nd}$ day The testing concentration of each ADC (Ab-mc-vc-PAB-MMAE, Ab-mc-MMAF, Ab-SPDB-DM4, Ab-SMCC-DM1 and Ab-MB-vc-duocarmycin) was respectively 300 nM, 100 nM, 30 nM, 10 nM, 3 nM, 1 nM, 0.3 nM and 0.1 nM. Each of above solution was Kept for 72 hours for testing.

The $5^{th}$ day

Figure 23:
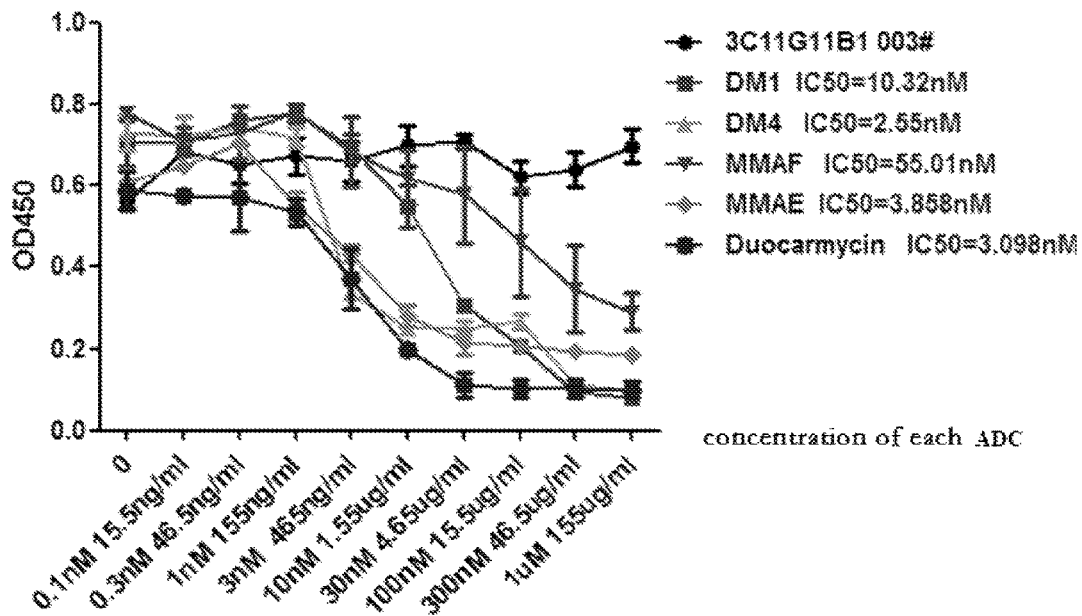
FIG. 23 shows the results of the viability assay of cancer cell line PLC treated with different ADCs of different concentrations respectively.
Figure 24:
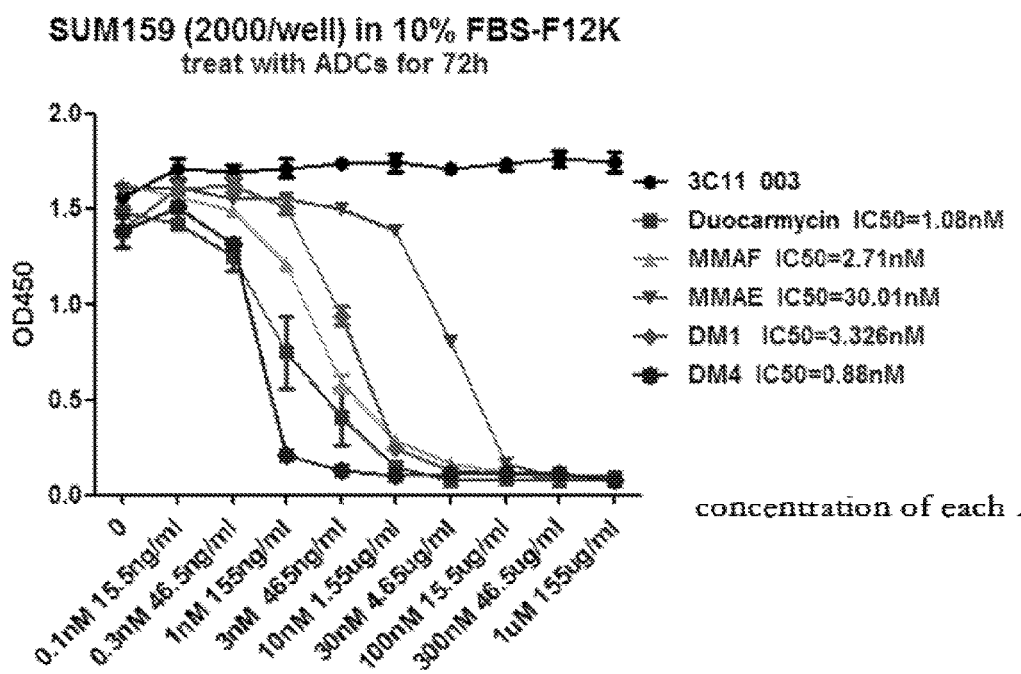
FIG. 24 shows the results of the viability assay of cancer cell line SUM159 treated with different ADCs of different concentrations respectively.

10 μL CCK-8 was added to each well, raising temperature to 37° C. for 2-4 hours. Based on cell color, optimal time was selected to test 0D450 and IC50 was calculated. The OD450 of PLC administrated with each agent (SNGmB1, Ab-mc-vc-PAB-MMAE, Ab-mc-MMAF, Ab-SMCC-DM1, Ab-SPDB-DM4 and Ab-MB-vc-duocarmycin) of different concentration was shown as FIG. 23. The OD450 of SUM159 administrated with each agent (SNGmB1, Ab-mc-vc-PAB-MMAE, Ab-mc-MMAF, Ab-SMCC-DM1, Ab-SPDB-DM4 and Ab-MB-vc-duocarmycin) of different concentration was shown as FIG. 24.

In conclusion, when the antibody or antigen binding fragment is conjugated with drug(s), its effects, such as the cytotoxicities to certain cell lines, are altered. In some cases, the cytotoxicities of such ADCs are potent than naked antibody or antigen binding fragment.

Example 18

Targeting ER-α36 by SNGmB1 for eliminating tumor metastasis

SNGmB1 inhibiting lung tumor metastasis

Figure 25:
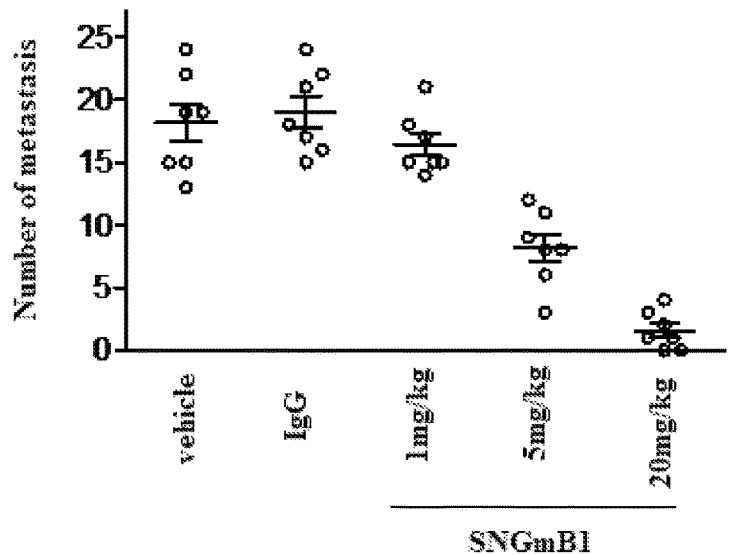
FIG. 25 shows metastasis of lung tumor cells on administrated with vehicle, control IgG and SNGmB1.

FACS-sorted 4T1-ER-α36 positive cells (ATCC) ($5*10^4$) were injected in the nude mice via tail vein. Average 20 mg/kg body SNGmB1 or control IgG (20 mg/kg body weight) was administered by tail vein injection every 3 or 4 days for 18 days, and tamoxifen (1 mg/kg body weight) was intragastric administrated synchronously. The metastasis of lung tumor cells is shown in FIG. 25. It is illustrated that the SNGmB1 prevents the metastasis of lung tumor.

Figure 26A:
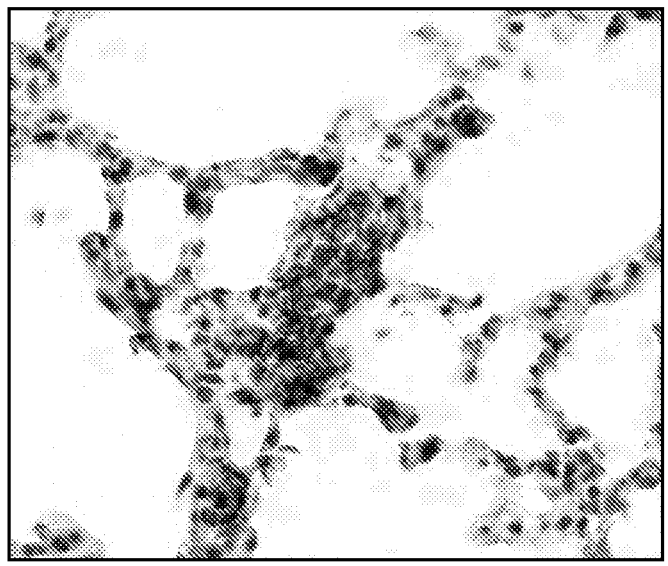
FIG. 26a shows immunohistochemical images of ALDH1 in lung metastatic foci with tamoxifen administrated tumor-bearing nude mice after control IgG treatment.
Figure 26B:
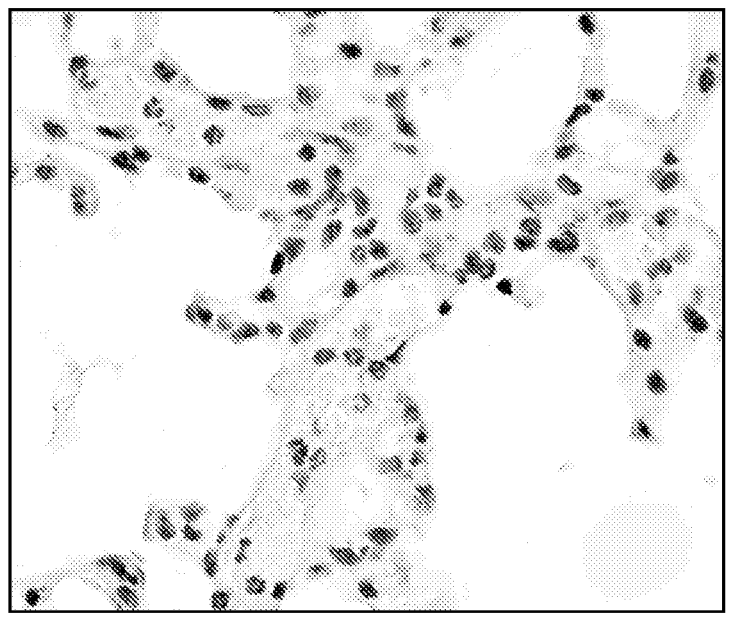
FIG. 26b shows immunohistochemical images of ALDH1 in lung metastatic foci with tamoxifen administrated tumor-bearing nude mice after SNGmB1 treatment.

Representative immunohistochemical images showing ALDH1 in lung metastatic foci with tamoxifen administrated tumor-bearing nude mice respectively after control IgG and SNGmB1 antibody treatment. Hematoxylin was used for counterstaining. Seen from FIG. 26a and FIG. 26b, it is illustrated that ALDH1 is decreased after SNGmB1 injection. scale bars 50 μm.

We claim:

1. An antibody or antigen-binding fragment thereof comprising:
   a) a light chain variable region comprising an LCDR1 of SEQ ID NO: 3, an LCDR2 of SEQ ID NO: 4, and an LCDR3 of SEQ ID NO: 5, and
   b) a heavy chain variable region comprising an HCDR1 of SEQ ID NO: 6, an HCDR2 of SEQ ID NO: 7, and an HCDR3 of SEQ ID NO: 8.

2. The antibody or antigen binding fragment thereof of claim 1, wherein the light chain variable region is selected from the group consisting of:
   a) the light chain variable region comprising SEQ ID NO: 9;
   b) the light chain variable region comprising SEQ ID NO: 11;
   c) the light chain variable region comprising SEQ ID NO: 12; and
   d) the light chain variable region comprising SEQ ID NO: 13.

3. The antibody or antigen binding fragment thereof of claim 1, wherein the heavy chain variable region is selected from the group consisting of:
   a) the heavy chain variable region comprising SEQ ID NO: 10;
   b) the heavy chain variable region comprising SEQ ID NO: 14; and
   c) the heavy chain variable region comprising SEQ ID NO: 15.

4. The antibody or antigen binding fragment thereof of claim 2, comprising a light chain comprising SEQ ID NO: 16, and a heavy chain of SEQ ID NO: 18.

5. The antibody or antigen binding fragment thereof of claim 2, comprising a light chain comprising SEQ ID NO: 20, and a heavy chain of SEQ ID NO: 22.

6. The antibody or antigen binding fragment thereof of claim 5, comprising a light chain selected from the group consisting of SEQ ID NO: 24, SEQ ID NO: 26, and SEQ ID NO: 28, and a heavy chain selected from the group consisting of SEQ ID NO: 30, and SEQ ID NO: 32.

7. The antibody or antigen-binding fragment thereof of claim 1, which is a monoclonal antibody, a polyclonal antibody, a bispecific antibody, a chimeric antibody, a humanized antibody, a recombinant antibody, a human antibody, a labeled antibody, a bivalent antibody, or an anti-idiotypic antibody.

8. The antibody or antigen-binding fragment thereof of claim 1, which is a camelized single domain antibody, a diabody, a scFv, an scFv dimer, a BsFv, a dsFv, a (dsFv)2, a dsFv-dsFv', an Fv fragment, a Fab, a Fab', a F(ab')2, a ds diabody, a nanobody, a domain antibody, or a bivalent domain antibody.

9. The antibody or antigen-binding fragment thereof of claim 1, further comprising an immunoglobulin constant region.

10. The antibody or antigen-binding fragment thereof of claim 9, wherein said immunoglobulin constant region is a λ light chain, κ light chain, γ1 heavy chain, γ2 heavy chain, γ3 heavy chain, or γ4 heavy chain constant region.

11. An isolated polypeptide comprising the heavy chain variable region and the light chain variable region of the antibody of claim 1.

12. A pharmaceutical composition comprising the antibody or antigen-binding fragment thereof as recited in claim 1 and one or more pharmaceutically acceptable carriers.

13. The pharmaceutical composition of claim 12, wherein said one or more pharmaceutical acceptable carriers are selected from the group consisting of pharmaceutically acceptable liquid, gel, solid carriers, aqueous vehicles, non-aqueous vehicles, antimicrobial agents, isotonic agents, buffers, antioxidants, anesthetics, suspending/dispending agents, sequestering or chelating agents, diluents, adjuvants, excipients, and non-toxic auxiliary substances.

14. A kit for detecting a sample expressing ER-α36, wherein the kit comprises the antibody or antigen-binding fragment of claim 1.

* * * * *

SEQUENCE LISTING

```
<160> NUMBER OF SEQ ID NOS: 33

<210> SEQ ID NO 1
<211> LENGTH: 310
<212> TYPE: PRT
<213> ORGANISM: Homo sapiens

<400> SEQUENCE: 1

Met Ala Met Glu Ser Ala Lys Glu Thr Arg Tyr Cys Ala Val Cys Asn
1               5                   10                  15

Asp Tyr Ala Ser Gly Tyr His Tyr Gly Val Trp Ser Cys Glu Gly Cys
            20                  25                  30

Lys Ala Phe Phe Lys Arg Ser Ile Gln Gly His Asn Asp Tyr Met Cys
        35                  40                  45

Pro Ala Thr Asn Gln Cys Thr Ile Asp Lys Asn Arg Arg Lys Ser Cys
    50                  55                  60

Gln Ala Cys Arg Leu Arg Lys Cys Tyr Glu Val Gly Met Met Lys Gly
65                  70                  75                  80

Gly Ile Arg Lys Asp Arg Arg Gly Gly Arg Met Leu Lys His Lys Arg
                85                  90                  95

Gln Arg Asp Asp Gly Glu Gly Arg Gly Glu Val Gly Ser Ala Gly Asp
            100                 105                 110

Met Arg Ala Ala Asn Leu Trp Pro Ser Pro Leu Met Ile Lys Arg Ser
        115                 120                 125

Lys Lys Asn Ser Leu Ala Leu Ser Leu Thr Ala Asp Gln Met Val Ser
    130                 135                 140

Ala Leu Leu Asp Ala Glu Pro Pro Ile Leu Tyr Ser Glu Tyr Asp Pro
145                 150                 155                 160

Thr Arg Pro Phe Ser Glu Ala Ser Met Met Gly Leu Leu Thr Asn Leu
                165                 170                 175

Ala Asp Arg Glu Leu Val His Met Ile Asn Trp Ala Lys Arg Val Pro
            180                 185                 190

Gly Phe Val Asp Leu Thr Leu His Asp Gln Val His Leu Leu Glu Cys
        195                 200                 205

Ala Trp Leu Glu Ile Leu Met Ile Gly Leu Val Trp Arg Ser Met Glu
    210                 215                 220

His Pro Gly Lys Leu Leu Phe Ala Pro Asn Leu Leu Leu Asp Arg Asn
225                 230                 235                 240
```

```
Gln Gly Lys Cys Val Glu Gly Met Val Glu Ile Phe Asp Met Leu Leu
                245                 250                 255

Ala Thr Ser Ser Arg Phe Arg Met Met Asn Leu Gln Gly Glu Glu Phe
            260                 265                 270

Val Cys Leu Lys Ser Ile Leu Leu Asn Ser Gly Ile Ser His Val
        275                 280                 285

Glu Ala Lys Lys Arg Ile Leu Asn Leu His Pro Lys Ile Phe Gly Asn
    290                 295                 300

Lys Trp Phe Pro Arg Val
305                 310

<210> SEQ ID NO 2
<211> LENGTH: 27
<212> TYPE: PRT
<213> ORGANISM: Homo sapiens

<400> SEQUENCE: 2

Gly Ile Ser His Val Glu Ala Lys Lys Arg Ile Leu Asn Leu His Pro
1               5                   10                  15

Lys Ile Phe Gly Asn Lys Trp Phe Pro Arg Val
            20                  25

<210> SEQ ID NO 3
<211> LENGTH: 11
<212> TYPE: PRT
<213> ORGANISM: Mus musculus

<400> SEQUENCE: 3

Ile Thr Ser Thr Asp Ile Asp Asp Met Asn
1               5                   10

<210> SEQ ID NO 4
<211> LENGTH: 7
<212> TYPE: PRT
<213> ORGANISM: Mus musculus

<400> SEQUENCE: 4

Glu Gly Asn Thr Leu Arg Pro
1               5

<210> SEQ ID NO 5
<211> LENGTH: 9
<212> TYPE: PRT
<213> ORGANISM: Mus musculus

<400> SEQUENCE: 5

Leu Gln Ser Asp Asn Leu Pro Leu Thr
1               5

<210> SEQ ID NO 6
<211> LENGTH: 5
<212> TYPE: PRT
<213> ORGANISM: Mus musculus

<400> SEQUENCE: 6

Ser His Asn Met His
1               5

<210> SEQ ID NO 7
<211> LENGTH: 17
<212> TYPE: PRT
<213> ORGANISM: Mus musculus
```

```
<400> SEQUENCE: 7

Ala Ile His Pro Val Asn Gly Asp Thr Ala Tyr Asn Gln Lys Phe Lys
1               5                   10                  15

Gly

<210> SEQ ID NO 8
<211> LENGTH: 8
<212> TYPE: PRT
<213> ORGANISM: Mus musculus

<400> SEQUENCE: 8

Glu Gly Tyr Gly Ser Val Asp Tyr
1               5

<210> SEQ ID NO 9
<211> LENGTH: 107
<212> TYPE: PRT
<213> ORGANISM: Mus musculus

<400> SEQUENCE: 9

Glu Thr Thr Val Thr Gln Ser Pro Ala Ser Leu Ser Met Thr Ile Gly
1               5                   10                  15

Glu Lys Val Thr Ile Arg Cys Ile Thr Ser Thr Asp Ile Asp Asp Asp
                20                  25                  30

Met Asn Trp Tyr Arg Lys Lys Pro Gly Gln Pro Pro Lys Leu Leu Ile
            35                  40                  45

Ser Glu Gly Asn Thr Leu Arg Pro Gly Val Pro Ser Arg Phe Ser Ser
        50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Leu
                85                  90                  95

Thr Phe Gly Ala Gly Thr Lys Leu Glu Leu Lys
            100                 105

<210> SEQ ID NO 10
<211> LENGTH: 117
<212> TYPE: PRT
<213> ORGANISM: Mus musculus

<400> SEQUENCE: 10

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser His
                20                  25                  30

Asn Met His Trp Ile Lys Gln Thr Pro Arg Gln Gly Leu Glu Trp Ile
            35                  40                  45

Gly Ala Ile His Pro Val Asn Gly Asp Thr Ala Tyr Asn Gln Lys Phe
        50                  55                  60

Lys Gly Lys Ala Thr Leu Thr Val Asp Lys Ser Ser Thr Ala Tyr
65                  70                  75                  80

Leu Gln Leu Ser Ser Leu Thr Ser Glu Glu Ser Ala Val Tyr Phe Cys
                85                  90                  95

Ala Arg Glu Gly Tyr Gly Ser Val Asp Tyr Trp Gly Gln Gly Thr Thr
            100                 105                 110

Leu Thr Val Ser Ser
            115
```

<210> SEQ ID NO 11
<211> LENGTH: 107
<212> TYPE: PRT
<213> ORGANISM: Artificial Sequence
<220> FEATURE:
<223> OTHER INFORMATION: LCVR of SNGHZDC01 (humanized)

<400> SEQUENCE: 11

```
Glu Thr Thr Val Thr Gln Ser Pro Ala Phe Met Ser Ala Thr Pro Gly
1               5                   10                  15

Asp Lys Val Asn Ile Ser Cys Ile Thr Ser Thr Asp Ile Asp Asp Asp
            20                  25                  30

Met Asn Trp Tyr Gln Gln Lys Pro Gly Glu Ala Pro Ile Leu Ile Ile
        35                  40                  45

Ser Glu Gly Asn Thr Leu Arg Pro Gly Ile Pro Pro Arg Phe Ser Ser
50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln Ser Asp Asn Leu Pro Leu
                85                  90                  95

Thr Phe Gly Gln Gly Thr Lys Leu Glu Ile Lys
            100                 105
```

<210> SEQ ID NO 12
<211> LENGTH: 107
<212> TYPE: PRT
<213> ORGANISM: Artificial Sequence
<220> FEATURE:
<223> OTHER INFORMATION: LCVR of SNGHZDC02 (humanized)

<400> SEQUENCE: 12

```
Glu Thr Thr Val Thr Gln Ser Pro Ala Phe Met Ser Ala Thr Pro Gly
1               5                   10                  15

Asp Lys Val Asn Ile Ser Cys Ile Thr Ser Thr Asp Ile Asp Asp Asp
            20                  25                  30

Met Asn Trp Tyr Gln Gln Lys Pro Gly Glu Ala Ala Ile Leu Ile Ile
        35                  40                  45

Ser Glu Gly Asn Thr Leu Arg Pro Gly Ile Pro Pro Arg Phe Ser Ser
50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln Ser Asp Asn Leu Pro Leu
                85                  90                  95

Thr Phe Gly Gln Gly Thr Lys Leu Glu Ile Lys
            100                 105
```

<210> SEQ ID NO 13
<211> LENGTH: 107
<212> TYPE: PRT
<213> ORGANISM: Artificial Sequence
<220> FEATURE:
<223> OTHER INFORMATION: LCVR of SNGHZDC03 (humanized)

<400> SEQUENCE: 13

```
Glu Thr Thr Val Thr Gln Ser Pro Ala Phe Met Ser Ala Thr Pro Gly
1               5                   10                  15

Asp Lys Val Asn Ile Ser Cys Ile Thr Ser Thr Asp Ile Asp Asp Asp
            20                  25                  30

Met Asn Trp Tyr Gln Gln Lys Pro Gly Glu Ala Pro Ile Leu Ile Ile
        35                  40                  45
```

```
                35                  40                  45
Ser Glu Gly Asn Thr Leu Arg Pro Gly Ile Pro Pro Arg Phe Ser Gly
 50                  55                  60

Ser Gly Tyr Gly Thr Asp Phe Thr Leu Thr Ile Asn Asn Ile Glu Ser
 65                  70                  75                  80

Glu Asp Ala Ala Tyr Tyr Phe Cys Leu Gln Ser Asp Asn Leu Pro Leu
                 85                  90                  95

Thr Phe Gly Gln Gly Thr Lys Leu Glu Ile Lys
            100                 105
```

<210> SEQ ID NO 14
<211> LENGTH: 117
<212> TYPE: PRT
<213> ORGANISM: Artificial Sequence
<220> FEATURE:
<223> OTHER INFORMATION: HCVR of SNGHZDc05 (humanized)

<400> SEQUENCE: 14

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser His
             20                  25                  30

Asn Met His Trp Val Arg Gln Ala Pro Gly Gln Gly Leu Glu Trp Ile
         35                  40                  45

Gly Ala Ile His Pro Val Asn Gly Asp Thr Ala Tyr Asn Gln Lys Phe
 50                  55                  60

Lys Gly Lys Ala Thr Leu Thr Val Asp Lys Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Glu Gly Tyr Gly Ser Val Asp Tyr Trp Gly Gln Gly Thr Leu
            100                 105                 110

Val Thr Val Ser Ser
            115
```

<210> SEQ ID NO 15
<211> LENGTH: 117
<212> TYPE: PRT
<213> ORGANISM: Artificial Sequence
<220> FEATURE:
<223> OTHER INFORMATION: HCVR of SNGHZDc06 (humanized)

<400> SEQUENCE: 15

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser His
             20                  25                  30

Asn Met His Trp Val Arg Gln Ala Pro Gly Gln Gly Leu Glu Trp Ile
         35                  40                  45

Gly Ala Ile His Pro Val Asn Gly Asp Thr Ala Tyr Asn Gln Lys Phe
 50                  55                  60

Lys Gly Lys Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Tyr Gly Ser Val Asp Tyr Trp Gly Gln Gly Thr Leu
            100                 105                 110
```

Val Thr Val Ser Ser
        115

<210> SEQ ID NO 16
<211> LENGTH: 214
<212> TYPE: PRT
<213> ORGANISM: Mus musculus

<400> SEQUENCE: 16

Glu Thr Thr Val Thr Gln Ser Pro Ala Ser Leu Ser Met Thr Ile Gly
1               5                   10                  15

Glu Lys Val Thr Ile Arg Cys Ile Thr Ser Thr Asp Ile Asp Asp Asp
            20                  25                  30

Met Asn Trp Tyr Arg Lys Lys Pro Gly Gln Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 17
<211> LENGTH: 645
<212> TYPE: DNA
<213> ORGANISM: Mus musculus

<400> SEQUENCE: 17
gagaccacag tgacccagag ccccgccagc ctcagcatga caatcggcga gaaggtgacc      60
atcaggtgca tcacatccac cgacatcgac gacgacatga actggtacag gaagaagccc     120
ggccaacccc ccaaactcct catcagcgag ggcaacacac tcaggcctgg cgtcccctcc     180
agattctcca gcagcggcta cggcaccgac ttcgtcttca ccatcgagaa catgctgtcc     240
gaggacgtgg ccgactacta ctgcctgcag tccgataacc tgcccctgac attcggcgcc     300
ggcaccaagc tcgagctgaa aagggccgac gccgccccta ccgtcagcat tttcccccct     360
tccagcgagc aactgacaag cggaggcgcc agcgtggtgt gcttcctcaa caacttctac     420
cccaaggaca tcaacgtgaa gtggaagatc gacggcagcg agagacaaaa cggagtgctg     480
aacagctgga ccgatcagga cagcaaggac agcacctaca gcatgagctc cacccctcaca    540

```
ctgaccaagg acgaatacga gaggcacaac tcctacacct gcgaggccac acacaagaca      600
agcacctccc ccatcgtcaa gagcttcaac aggaacgagt gctga                     645
```

<210> SEQ ID NO 18
<211> LENGTH: 453
<212> TYPE: PRT
<213> ORGANISM: Mus musculus

<400> SEQUENCE: 18

```
Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser His
            20                  25                  30

Asn Met His Trp Ile Lys Gln Thr Pro Arg Gln Gly Leu Glu Trp Ile
        35                  40                  45

Gly Ala Ile His Pro Val Asn Gly Asp Thr Ala Tyr Asn Gln Lys Phe
    50                  55                  60

Lys Gly Lys Ala Thr Leu Thr Val Asp Lys Ser Ser Thr Ala Tyr
65                  70                  75                  80

Leu Gln Leu Ser Ser Leu Thr Ser Glu Glu Ser Ala Val Tyr Phe Cys
                85                  90                  95

Ala Arg Glu Gly Tyr Gly Ser Val Asp Tyr Trp Gly Gln Gly Thr Thr
            100                 105                 110

Leu Thr Val Ser Ser Ala Lys Thr Thr Pro Pro Ser Val Tyr Pro Leu
        115                 120                 125

Ala Pro Gly Cys Gly Asp Thr Thr Gly Ser Ser Val Thr Leu Gly Cys
    130                 135                 140

Leu Val Lys Gly Tyr Phe Pro Glu Ser Val Thr Val Thr Trp Asn Ser
145                 150                 155                 160

Gly Ser Leu Ser Ser Ser Val His Thr Phe Pro Ala Leu Leu Gln Ser
                165                 170                 175

Gly Leu Tyr Thr Met Ser Ser Ser Val Thr Val Pro Ser Ser Thr Trp
            180                 185                 190

Pro Ser Gln Thr Val Thr Cys Ser Val Ala His Pro Ala Ser Ser Thr
        195                 200                 205

Thr Val Asp Lys Lys Leu Glu Pro Ser Gly Pro Ile Ser Thr Ile Asn
    210                 215                 220

Pro Cys Pro Pro Cys Lys Glu Cys His Lys Cys Pro Ala Pro Asn Leu
225                 230                 235                 240

Glu Gly Gly Pro Ser Val Phe Ile Phe Pro Pro Asn Ile Lys Asp Val
                245                 250                 255

Leu Met Ile Ser Leu Thr Pro Lys Val Thr Cys Val Val Val Asp Val
            260                 265                 270

Ser Glu Asp Asp Pro Asp Val Gln Ile Ser Trp Phe Val Asn Asn Val
        275                 280                 285

Glu Val His Thr Ala Gln Thr Gln Thr His Arg Glu Asp Tyr Asn Ser
    290                 295                 300

Thr Ile Arg Val Val Ser Thr Leu Pro Ile Gln His Gln Asp Trp Met
305                 310                 315                 320

Ser Gly Lys Glu Phe Lys Cys Lys Val Asn Asn Lys Asp Leu Pro Ser
                325                 330                 335

Pro Ile Glu Arg Thr Ile Ser Lys Ile Lys Gly Leu Val Arg Ala Pro
            340                 345                 350

Gln Val Tyr Ile Leu Pro Pro Pro Ala Glu Gln Leu Ser Arg Lys Asp
```

Val Ser Leu Thr Cys Leu Val Val Gly Phe Asn Pro Gly Asp Ile Ser
355                 360                 365
Val Glu Trp Thr Ser Asn Gly His Thr Glu Glu Asn Tyr Lys Asp Thr
370                 375                 380
Ala Pro Val Leu Asp Ser Asp Gly Ser Tyr Phe Ile Tyr Ser Lys Leu
385                 390                 395                 400
Asn Met Lys Thr Ser Lys Trp Glu Lys Thr Asp Ser Phe Ser Cys Asn
        405                 410                 415
Val Arg His Glu Gly Leu Lys Asn Tyr Tyr Leu Lys Lys Thr Ile Ser
    420                 425                 430
Arg Ser Pro Gly Lys
435                 440                 445
450

<210> SEQ ID NO 19
<211> LENGTH: 1362
<212> TYPE: DNA
<213> ORGANISM: Mus musculus

<400> SEQUENCE: 19

```
caggcctacc tgcaacaaag cggcgctgag ctcgtcaggc ctggagctag cgtgaagatg      60
tcctgtaagg ccagcggcta cacctttacc agccacaaca tgcactggat caagcagacc     120
cctaggcagg gactggaatg gatcggagcc attcaccccg tgaacggaga taccgcttat     180
aaccagaagt tcaagggcaa ggctaccctg accgtcgaca gtcctcctc cacagcctat     240
ctgcagctca gctccctgac cagcgaagag agcgccgtct acttttgcgc cagagaaggc     300
tacggcagcg tggattactg gggccaggga accaccctca ccgtgagctc ggccaagacc     360
acccctccta cgtctaccc tctggctccc ggctgtggag acaccaccgg aagctccgtc     420
accctgggat gtctggtcaa gggctacttc cctgagtccg tgaccgtgac ctggaactcc     480
ggctccctga gcagctccgt gcacaccttc ccgctctgc tgcagtccgg cctgtacacc     540
atgagctcca gcgtcacagt gccctccagc acctggcctt cccagacagt gacctgcagc     600
gtggcccacc ctgcttccag caccacagtc gacaaaaagc tggagcctag cggccctatt     660
tccaccatca cccctgccc ccctgcaag gagtgccata agtgtcctgc ccctaatctc     720
gagggcggac ccagcgtgtt catcttcccc ccaacatca agacgtcct gatgatctcc     780
ctgacaccca aggtgacatg cgtcgtcgtc gacgtgagcg aagacgaccc cgacgtgcaa     840
atctcctggt tcgtgaacaa cgtggaggtg cacacagccc agacccaaac ccacagagag     900
gactacaaca gcaccattag ggtggtcagc acactcccca tccaacacca ggactggatg     960
tccggcaagg agtttaagtg caaggtcaac aacaaggacc tgcccagccc catcgagagg    1020
accatctcca agattaaggg cctggtgagg gctcctcagg tgtatatcct ccccccccct    1080
gctgaacagc tgtccagaaa agacgtcagc ctgacctgcc tggtcgtcgg attcaatccc    1140
ggagacatct ccgtcgaatg gaccagcaac ggacacacag aggagaacta caaggacaca    1200
gcccctgtcc tggactccga cggctcctac ttcatctact ccaagctgaa tatgaagacc    1260
agcaagtggg agaagaccga ctccttcagc tgtaacgtga ggcacgaggg cctcaagaac    1320
tactatctga agaagacaat ctccaggagc cccggcaagt ga                       1362
```

<210> SEQ ID NO 20
<211> LENGTH: 214
<212> TYPE: PRT
<213> ORGANISM: Artificial Sequence
<220> FEATURE:
<223> OTHER INFORMATION: SNGmB1 light chain V region + Hu C

<400> SEQUENCE: 20

Glu Thr Thr Val Thr Gln Ser Pro Ala Ser Leu Ser Met Thr Ile Gly
1               5                   10                  15

Glu Lys Val Thr Ile Arg Cys Ile Thr Ser Thr Asp Ile Asp Asp Asp
            20                  25                  30

Met Asn Trp Tyr Arg Lys Lys Pro Gly Gln Pro Pro Lys Leu Leu Ile
        35                  40                  45

Ser Glu Gly Asn Thr Leu Arg Pro Gly Val Pro Ser Arg Phe Ser Ser
50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 21
<211> LENGTH: 645
<212> TYPE: DNA
<213> ORGANISM: Artificial Sequence
<220> FEATURE:
<223> OTHER INFORMATION: SNGmB1 light chain V region + Hu C

<400> SEQUENCE: 21
gagaccacag tgacccagag ccccgccagc ctcagcatga caatcggcga agaggtgacc      60
atcaggtgca tcacatccac cgacatcgac gacgacatga actggtacag gaagaagccc     120
ggccaacccc ccaaactcct catcagcgag ggcaacacac tcaggcctgg cgtcccctcc     180
agattctcca gcagcggcta cggcaccgac ttcgtcttca ccatcgagaa catgctgtcc     240
gaggacgtgg ccgactacta ctgcctgcag tccgataacc tgcccctgac attcggcgcc     300
ggcaccaagc tcgagctgaa aaggaccgtg gccgccccct ccgtgttcat ttttccccccc     360
agcgacgagc aactgaagag cggaaccgcc agcgtggtgt gcctgctcaa caacttctac     420
cccagggagg ccaaggtgca gtggaaggtg gacaacgccc tgcagagcgg caacagccag     480
gagagcgtca ccgagcagga cagcaaggac tccacctaca gcctgagctc cacactcacc     540
ctgtccaagg ccgactacga gaagcacaag gtgtacgcct gcgaggtgac ccaccaaggc     600
ctgtccagcc ccgtgaccaa gagcttcaac agggggcgagt gctga                   645

<210> SEQ ID NO 22
<211> LENGTH: 447
<212> TYPE: PRT
<213> ORGANISM: Artificial Sequence
<220> FEATURE:
<223> OTHER INFORMATION: SNGmB1 heavy chain V region + Hu IgG1 C

<400> SEQUENCE: 22

```
Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser His
            20                  25                  30

Asn Met His Trp Ile Lys Gln Thr Pro Arg Gln Gly Leu Glu Trp Ile
        35                  40                  45

Gly Ala Ile His Pro Val Asn Gly Asp Thr Ala Tyr Asn Gln Lys Phe
    50                  55                  60

Lys Gly Lys Ala Thr Leu Thr Val Asp Lys Ser Ser Thr Ala Tyr
65                  70                  75                  80

Leu Gln Leu Ser Ser Leu Thr Ser Glu Glu Ser Ala Val Tyr Phe Cys
                85                  90                  95

Ala Arg Glu Gly Tyr Gly Ser Val Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365
```

```
Val Lys Gly Phe Tyr Pro Ser Asp Ile Ala Val Glu Trp Glu Ser Asn
        370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
His Asn His Tyr Thr Gln Lys Ser Leu Ser Leu Ser Pro Gly Lys
            435                 440                 445

<210> SEQ ID NO 23
<211> LENGTH: 1344
<212> TYPE: DNA
<213> ORGANISM: Artificial Sequence
<220> FEATURE:
<223> OTHER INFORMATION: SNGmB1 heavy chain V region + Hu IgG1 C

<400> SEQUENCE: 23
caggcctacc tgcaacaaag cggcgctgag ctcgtcaggc tggagctagc gtgaagatg      60
tcctgtaagg ccagcggcta cacctttacc agccacaaca tgcactggat caagcagacc    120
cctaggcagg gactggaatg gatcggagcc attcaccccg tgaacggaga taccgcttat    180
aaccagaagt tcaagggcaa ggctaccctg accgtcgaca gtcctcctc cacagcctat     240
ctgcagctca gctccctgac cagcgaagag agcgccgtct acttttgcgc cagagaaggc    300
tacggcagcg tggattactg gggccaggga accaccctca ccgtgagctc ggccagcacc    360
aaggaccta gcgtgtttcc tctcgccccc tcctccaaaa gcaccagcgg aggaaccgct     420
gctctcggat gtctggtgaa ggactacttc cctgaacccg tcaccgtgag ctggaatagc    480
ggcgctctga caagcggagt ccatacattc cctgctgtgc tgcaaagcag cggactctat    540
tccctgtcca gcgtcgtcac agtgcccagc agcagcctgg gcacccagac ctacatctgt   600
aacgtcaacc acaagccctc caacaccaag gtggacaaga agtggagcc caaatcctgc    660
gacaagacac acacctgtcc ccctgtcct gctcccgaac tcctcggagg ccctagcgtc     720
ttcctctttc ctcccaaacc caaggacacc ctcatgatca gcagaacccc tgaagtcacc    780
tgtgtcgtcg tggatgtcag ccatgaggac cccgaggtga aattcaactg gtatgtcgat    840
ggcgtcgagg tgcacaacgc caaaaccaag cccagggagg aacagtacaa ctccacctac    900
agggtggtgt ccgtgctgac agtcctccac caggactggc tgaacggcaa ggagtacaag    960
tgcaaggtgt ccaacaaggc tctccctgcc cccattgaga gaccatcag caaggccaaa    1020
ggccaaccca gggagcccca ggtctataca ctgcctccct ccagggacga actcaccaag    1080
aaccaggtgt ccctgacctg cctggtcaag ggcttttatc ccagcgacat cgccgtcgag    1140
tgggagtcca acggacagcc cgagaataac tacaagacca cccctcctgt cctcgactcc    1200
gacggctcct tcttcctgta cagcaagctg accgtggaca aaagcaggtg gcagcaggga    1260
aacgtgttct cctgcagcgt gatgcacgaa gccctccaca accactacac ccagaaaagc    1320
ctgtccctga gccccggcaa atga                                           1344

<210> SEQ ID NO 24
<211> LENGTH: 214
<212> TYPE: PRT
<213> ORGANISM: Artificial Sequence
<220> FEATURE:
<223> OTHER INFORMATION: humanized SNGmB1 light chain V region V4, P44,
      L46, S49, S64 + Hu C
```

<400> SEQUENCE: 24

```
Glu Thr Thr Val Thr Gln Ser Pro Ala Phe Met Ser Ala Thr Pro Gly
1               5                   10                  15

Asp Lys Val Asn Ile Ser Cys Ile Thr Ser Thr Asp Ile Asp Asp Asp
            20                  25                  30

Met Asn Trp Tyr Gln Gln Lys Pro Gly Glu Ala Pro Ile Leu Ile Ile
        35                  40                  45

Ser Glu Gly Asn Thr Leu Arg Pro Gly Ile Pro Pro Arg Phe Ser Ser
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln Ser Asp Asn Leu Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 25
<211> LENGTH: 645
<212> TYPE: DNA
<213> ORGANISM: Artificial Sequence
<220> FEATURE:
<223> OTHER INFORMATION: humanized SNGmB1 light chain V region V4, P44, L46, S49, S64 + Hu C

<400> SEQUENCE: 25

```
gagaccaccg tgacccagag ccctgccttt atgagcgcca cccctggcga caaggtgaac      60
atcagctgca tcaccagcac cgacatcgac gacgacatga actggtacca gcagaagccc    120
ggagaggccc ccatcctcat catcagcgag ggcaacaccc tgaggcctgg cattccccc     180
agattcagca gcagcggcta cggcaccgac ttcaccctga ccatcaacaa catcgagagc    240
gaggacgccg cctactactt ctgcctgcag tccgacaacc tgcccctgac cttcggccag    300
ggcaccaagc tggagatcaa gaggaccgtg gccgccccct ccgtgttcat tttccccccc    360
agcgacgagc aactgaagag cggaaccgcc agcgtggtgt gcctgctcaa caacttctac    420
cccagggagg ccaaggtgca gtggaaggtg acaacgccc tgcagagcgg caacagccag    480
gagagcgtca ccgagcagga cagcaaggac tccacctaca gcctgagctc cacactcacc    540
ctgtccaagg ccgactacga gaagcacaag gtgtacgcct gcgaggtgac ccaccaaggc    600
ctgtccagcc ccgtgaccaa gagcttcaac agggcgagt gctga                      645
```

<210> SEQ ID NO 26
<211> LENGTH: 214
<212> TYPE: PRT
<213> ORGANISM: Artificial Sequence
<220> FEATURE:
<223> OTHER INFORMATION: humanized SNGmB1 light chain V region V4, L46, S49, S64 + Hu C

<400> SEQUENCE: 26

```
Glu Thr Thr Val Thr Gln Ser Pro Ala Phe Met Ser Ala Thr Pro Gly
1               5                   10                  15

Asp Lys Val Asn Ile Ser Cys Ile Thr Ser Thr Asp Ile Asp Asp Asp
            20                  25                  30

Met Asn Trp Tyr Gln Gln Lys Pro Gly Glu Ala Ala Ile Leu Ile Ile
        35                  40                  45

Ser Glu Gly Asn Thr Leu Arg Pro Gly Ile Pro Pro Arg Phe Ser Ser
50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln Ser Asp Asn Leu Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 27
<211> LENGTH: 645
<212> TYPE: DNA
<213> ORGANISM: Artificial Sequence
<220> FEATURE:
<223> OTHER INFORMATION: humanized SNGmB1 light chain V region V4, L46, S49, S64 + Hu C

<400> SEQUENCE: 27

```
gagaccaccg tgacccagag ccctgccttt atgagcgcca cccctggcga caaggtgaac      60
atcagctgca tcaccagcac cgacatcgac gacgacatga actggtacca gcagaagccc     120
ggagaggccg ccatcctcat catcagcgag ggcaacaccc tgaggcctgg cattccccgc     180
agattcagca gcagcggcta cggcaccgac ttcaccctga ccatcaacaa catcgagagc     240
gaggacgccg cctactactt ctgcctgcag tccgacaacc tgcccctgac cttcggccag     300
ggcaccaagc tggagatcaa gaggaccgtg gccgccccct ccgtgttcat tttcccccgc     360
agcgacgagc aactgaagag cggaaccgcc agcgtggtgt gcctgctcaa caacttctac     420
cccagggagg ccaaggtgca gtggaaggtg gacaacgccc tgcagagcgg caacagccag     480
```

```
gagagcgtca ccgagcagga cagcaaggac tccacctaca gcctgagctc cacactcacc    540
ctgtccaagg ccgactacga aaagcacaag gtgtacgcct gcgaggtgac ccaccaaggc    600
ctgtccagcc ccgtgaccaa gagcttcaac agggggcgagt gctga                   645
```

<210> SEQ ID NO 28
<211> LENGTH: 214
<212> TYPE: PRT
<213> ORGANISM: Artificial Sequence
<220> FEATURE:
<223> OTHER INFORMATION: humanized SNGmB1 light chain V region V4, P44,
      L46, S49 + Hu C

<400> SEQUENCE: 28

```
Glu Thr Thr Val Thr Gln Ser Pro Ala Phe Met Ser Ala Thr Pro Gly
1               5                   10                  15

Asp Lys Val Asn Ile Ser Cys Ile Thr Ser Thr Asp Ile Asp Asp Asp
            20                  25                  30

Met Asn Trp Tyr Gln Gln Lys Pro Gly Glu Ala Pro Ile Leu Ile Ile
        35                  40                  45

Ser Glu Gly Asn Thr Leu Arg Pro Gly Ile Pro Pro Arg Phe Ser Gly
50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln Ser Asp Asn Leu Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 29
<211> LENGTH: 645
<212> TYPE: DNA
<213> ORGANISM: Artificial Sequence
<220> FEATURE:
<223> OTHER INFORMATION: humanized SNGmB1 light chain V region V4, P44,
      L46, S49 + Hu C

<400> SEQUENCE: 29

```
gagaccaccg tgacccagag ccctgccttt atgagcgcca cccctggcga caaggtgaac    60
atcagctgca tcaccagcac cgacatcgac gacgacatga actggtacca gcagaagccc    120
ggagaggccc ccatcctcat catcagcgag ggcaacaccc tgaggcctgg cattcccccc    180
agattcagcg gcagcggcta cggcaccgac ttcaccctga ccatcaacaa catcgagagc    240
gaggacgccg cctactactt ctgcctgcag tccgacaacc tgcccctgac cttcggccag    300
```

```
ggcaccaagc tggagatcaa gaggaccgtg gccgcccct ccgtgttcat ttccccccc      360 agcgacgagc aactgaagag cggaaccgcc agcgtggtgt gcctgctcaa caacttctac    420
cccagggagg ccaaggtgca gtggaaggtg acaacgccc tgcagagcgg caacagccag     480
gagagcgtca ccgagcagga cagcaaggac tccacctaca gcctgagctc cacactcacc    540
ctgtccaagg ccgactacga gaagcacaag gtgtacgcct gcgaggtgac ccaccaaggc    600
ctgtccagcc ccgtgaccaa gagcttcaac agggcgagt gctga                    645
```

<210> SEQ ID NO 30
<211> LENGTH: 447
<212> TYPE: PRT
<213> ORGANISM: Artificial Sequence
<220> FEATURE:
<223> OTHER INFORMATION: humanized SNGmB1 heavy chain V region T28,
      L81 + Hu IgG1 C

<400> SEQUENCE: 30

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Asn Met His Trp Val Arg Gln Ala Pro Gly Gln Gly Leu Glu Trp Ile
        35                  40                  45

Gly Ala Ile His Pro Val Asn Gly Asp Thr Ala Tyr Asn Gln Lys Phe
    50                  55                  60

Lys Gly Lys Ala Thr Leu Thr Val Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Gly Tyr Gly Ser Val Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
```

```
                290                 295                 300
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 31
<211> LENGTH: 1344
<212> TYPE: DNA
<213> ORGANISM: Artificial Sequence
<220> FEATURE:
<223> OTHER INFORMATION: humanized SNGmB1 heavy chain V region T28,
      L81 + Hu IgG1 C

<400> SEQUENCE: 31
caggtgcagc tggtgcaaag cggcgccgag gtgaaaaagc tggcgccagc cgtcaaggtg      60
agctgcaagg ccagcggcta caccttcacc agccacaaca tgcactgggt gaggcaggct     120
cctggacagg gactggagtg gatcggcgcc atccaccctg taacggcga caccgcctac     180 aaccagaagt tcaagggcaa ggccaccctg accgtggaca gagcaccag caccgcctac     240 ctggagctga gcagcctgag gagcgaggac accgccgtgt actactgcgc cagagagggc     300
tacggcagcg tggactactg gggccaaggc accctggtga ccgtgagcag cgccagcacc     360
aaaggaccta cgtgttccc tctcgccccc tcctccaaaa gcaccagcgg aggaaccgct     420
gctctcggat gtctggtgaa ggactacttc cctgaacccg tcaccgtgag ctggaatagc     480
ggcgctctga caagcggagt ccatacattc cctgctgtgc tgcaaagcag cggactctat     540
tccctgtcca gcgtcgtcac agtgcccagc agcagcctgg gcacccagac ctacatctgt     600
aacgtcaacc acaagccctc caacaccaag gtggacaaga agtggagcc caaatcctgc     660 gacaagacac acacctgtcc ccctgtcct gctcccgaac tcctcggagg ccctagcgtc     720
ttcctctttc ctcccaaacc caaggacacc ctcatgatca gcagaacccc tgaagtcacc     780
tgtgtcgtcg tggatgtcag ccatgaggac cccgaggtga aattcaactg gtatgtcgat     840
ggcgtcgagg tgcacaacgc caaaaccaag cccagggagg aacagtacaa ctccacctac     900
agggtggtgt ccgtgctgac agtcctccac caggactggc tgaacggcaa ggagtacaag     960
tgcaaggtgt ccaacaaggc tctccctgcc ccattgaga agaccatcag caaggccaaa    1020
ggccaaccca gggagcccca ggtctataca ctgcctccct ccaggacga actcaccaag    1080 aaccaggtgt ccctgacctg cctggtcaag ggctttatc ccagcgacat cgccgtcgag    1140
tgggagtcca acggacagcc cgagaataac tacaagacca cccctcctgt cctcgactcc    1200
```
gacggctcct tcttcctgta cagcaagctg accgtggaca aaagcaggtg gcagcaggga    1260
aacgtgttct cctgcagcgt gatgcacgaa gccctccaca accactacac ccagaaaagc    1320
ctgtccctga gccccggcaa atga                                           1344

<210> SEQ ID NO 32
<211> LENGTH: 447
<212> TYPE: PRT
<213> ORGANISM: Artificial Sequence
<220> FEATURE:
<223> OTHER INFORMATION: humanized SNGmB1 heavy chain V region T28 + Hu
      IgG1 C

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Asn Met His Trp Val Arg Gln Ala Pro Gly Gln Gly Leu Glu Trp Ile
        35                  40                  45

Gly Ala Ile His Pro Val Asn Gly Asp Thr Ala Tyr Asn Gln Lys Phe
    50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Gly Ser Val Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile

```
                    325                 330                 335
Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 33
<211> LENGTH: 1344
<212> TYPE: DNA
<213> ORGANISM: Artificial Sequence
<220> FEATURE:
<223> OTHER INFORMATION: humanized SNGmB1 heavy chain V region T28 + Hu
      IgG1 C

<400> SEQUENCE: 33
caggtgcagc tggtgcaaag cggcgccgag gtgaaaaagc ctggcgccag cgtcaaggtg      60
agctgcaagg ccagcggcta caccttcacc agccacaaca tgcactgggt gaggcaggct     120
cctggacagg gactggagtg gatcggcgcc atccaccctg taacggcga caccgcctac     180 aaccagaagt tcaagggcaa ggccaccctg accgtggaca gagcaccag caccgcctac     240 atggagctga gcagcctgag gagcgaggac accgccgtgt actactgcgc cagagagggc     300
tacggcagcg tggactactg gggccaaggc accctggtga ccgtgagcag cgccagcacc     360
aaaggaccta gcgtgtttcc tctcgccccc tcctccaaaa gcaccagcgg aggaaccgct     420
gctctcggat gtctggtgaa ggactacttc cctgaacccg tcaccgtgag ctggaatagc     480
ggcgctctga agcggagt ccatacattc ctgctgtgc tgcaaagcag cggactctat      540
tccctgtcca gcgtcgtcac agtgcccagc agcagcctgg gcacccagac ctacatctgt     600
aacgtcaacc acaagccctc caacaccaag gtggacaaga agtggagcc caaatcctgc     660 gacaagacac acacctgtcc ccctgtcct gctcccgaac tcctcggagg ccctagcgtc      720
ttcctctttc ctcccaaacc caaggacacc ctcatgatca gcagaacccc tgaagtcacc     780
tgtgtcgtcg tggatgtcag ccatgaggac cccgaggtga aattcaactg gtatgtcgat     840
ggcgtcgagg tgcacaacgc caaaaccaag cccagggagg aacagtacaa ctccaccac     900 agggtggtgt ccgtgctgac agtcctccac caggactggc tgaacggcaa ggagtacaag     960
tgcaaggtgt ccaacaaggc tctccctgcc ccattgaga gaccatcag caaggccaaa     1020 ggccaaccca gggagcccca ggtctataca ctgcctccct ccagggacga actcaccaag     1080
aaccaggtgt ccctgacctg cctggtcaag ggcttttatc ccagcgacat cgccgtgag     1140 tgggagtcca acggacagcc cgagaataac tacaagacca ccccctcctgt cctcgactcc     1200
```

```
gacggctcct tcttcctgta cagcaagctg accgtggaca aaagcaggtg gcagcaggga    1260
aacgtgttct cctgcagcgt gatgcacgaa gccctccaca accactacac ccagaaaagc    1320
ctgtccctga gccccggcaa atga                                           1344
```